(12) United States Patent　　　(10) Patent No.: US 12,648,712 B2
　　Barlow et al.　　　　　　　　　(45) Date of Patent:　　Jun. 9, 2026

(54) EYE MASK SYSTEM

(71) Applicant: RESMED PTY LTD, Bella Vista (AU)

(72) Inventors: Adam Francis Barlow, Sydney (AU); Justin John Formica, Sydney (AU); Sung Hoon Mun, Sydney (AU); Hugh Francis Stewart Thomas, Sydney (AU); Liam Holley, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 621 days.

(21) Appl. No.: 18/014,000

(22) PCT Filed: Jun. 30, 2021

(86) PCT No.: PCT/AU2021/050690
　　§ 371 (c)(1),
　　(2) Date: Dec. 30, 2022

(87) PCT Pub. No.: WO2022/000030
　　PCT Pub. Date: Jan. 16, 2022

(65) Prior Publication Data
　　US 2023/0337937 A1　　Oct. 26, 2023

(30) Foreign Application Priority Data

Jun. 30, 2020　(AU) ................................ 2020902195
Jun. 30, 2020　(AU) ................................ 2020902196

(51) Int. Cl.
　　*A61M 16/06*　　　(2006.01)
　　*A61B 5/00*　　　　(2006.01)
　　*A61B 5/08*　　　　(2006.01)
(52) U.S. Cl.
　　CPC .......... *A61B 5/0826* (2013.01); *A61B 5/4818* (2013.01); *A61B 5/6803* (2013.01); *A61B 5/6821* (2013.01); *A61M 16/0666* (2013.01)

(58) Field of Classification Search
　　CPC ....... A61B 5/4809; A61C 1/081; A61C 19/08; A61C 2203/00; A61F 5/56; A61F 9/04;
　　　　　　　(Continued)

(56) References Cited

U.S. PATENT DOCUMENTS 4,782,832 A　　11/1988　Trimble et al.
4,944,310 A　　7/1990　Sullivan
　　　　　　　　(Continued)

FOREIGN PATENT DOCUMENTS

CN　　102698349 A　　10/2012
CN　　105126222 A　　12/2015
　　　　　　（Continued）

OTHER PUBLICATIONS

International Preliminary Report on Patentability mailed Aug. 22, 2023 in International Application No. PCT/AU2021/050690, 13 pages.
（Continued）

*Primary Examiner* — Annette Dixon
(74) *Attorney, Agent, or Firm* — Nixon & Vanderhye P.C.

(57) ABSTRACT

An eye mask system for providing respiratory pressure therapy (RPT) for treatment of sleep disordered breathing, comprising: an eye mask configured to cover the user's eyes in use; one or more transducers configured to influence the user's sleep and/or detect characteristics of the user or the user's sleep. The eye mask system may comprise: a connection port to receive a pressurised flow of air or a flow generator; the eye mask system may comprise a plenum chamber, a seal-forming structure to form a seal with a region of the user's face and a vent to allow flow of gases exhaled by the user to ambient. The eye mask system may operate in a non-treatment mode in which RPT is not provided to the user, and a treatment mode in which RPT is provided to the user.

24 Claims, 31 Drawing Sheets

(58) Field of Classification Search

CPC .... A61M 16/01; A61M 16/024; A61M 16/06; A61M 16/0666; A61M 16/202; A61M 16/209; A61M 2021/0022; A61M 2021/005; A61M 2021/0083; A61M 21/00; A61M 21/02; A61M 2202/0241; A61M 2202/0283; A61M 2205/3303; A61M 2205/3375; A61M 2205/3569; A61M 2205/3592; A61M 2205/505; A61M 2205/507; A61M 2205/59; A61M 2230/005; A61M 2230/04; A61M 2230/10; A61M 2230/63; G02C 11/10; G02C 7/101; G06F 3/002; G06F 3/011; G06T 11/60

See application file for complete search history.

(56) References Cited

U.S. PATENT DOCUMENTS

| | | | |
|---|---|---|---|
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 10,646,676 | B1 | 5/2020 | Matich |
| 2009/0044808 | A1 | 2/2009 | Guney et al. |
| 2009/0050156 | A1 | 2/2009 | Ng et al. |
| 2009/0260630 | A1 | 10/2009 | Saldivar et al. |
| 2010/0000534 | A1 | 1/2010 | Kooij et al. |
| 2013/0000642 | A1 | 1/2013 | Fearnot et al. |
| 2013/0056010 | A1 | 3/2013 | Walker et al. |
| 2013/0247906 | A1 | 9/2013 | Kwok et al. |
| 2013/0303837 | A1 | 11/2013 | Berka et al. |
| 2016/0354250 | A1 | 12/2016 | Paulson |
| 2017/0361045 | A1 | 12/2017 | Fu et al. |
| 2018/0125700 | A1* | 5/2018 | Ray ..................... A61M 16/024 |
| 2018/0239416 | A1* | 8/2018 | Laskin .................... G06F 3/011 |
| 2019/0217031 | A1 | 7/2019 | Kuck et al. |
| 2019/0282777 | A1 | 9/2019 | Kwok et al. |

FOREIGN PATENT DOCUMENTS

| | | | |
|---|---|---|---|
| CN | 106163599 | A | 11/2016 |
| CN | 109414557 | A | 3/2019 |
| CN | 210330583 | U | 4/2020 |
| JP | 2009-544372 | A | 12/2009 |
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2008/011683 | A1 | 1/2008 |
| WO | WO 2009/052560 | A1 | 4/2009 |
| WO | WO 2010/135785 | A1 | 12/2010 |
| WO | WO 2011/112807 | A1 | 9/2011 |
| WO | WO 2012/113027 | A1 | 8/2012 |
| WO | WO 2012/171072 | A1 | 12/2012 |
| WO | WO 2013/020167 | A1 | 2/2013 |
| WO | WO 2015/131145 | A1 | 9/2015 |
| WO | WO 2017/185140 | A1 | 11/2017 |
| WO | WO 2018/018074 | A1 | 2/2018 |
| WO | WO 2018/071436 | A1 | 4/2018 |
| WO | WO 2021/189114 | A1 | 9/2021 |

OTHER PUBLICATIONS

"*Respiratory Physiology*", by John B. West, Lippincott Williams & Wilkins, 9th edition published 2012 (8 pages).

International Search Report mailed Oct. 5, 2021 in International Application No. PCT/AU2021/050690, 8 pages.

Written Opinion of the International Searching Authority mailed Oct. 5, 2021 in International Application No. PCT/AU2021/050690, 16 pages.

International Preliminary Report on Patentability mailed Jun. 28, 2022 in International Application No. PCT/AU2021/050690, 53 pages.

Written Opinion of the International Preliminary Examining Authority mailed in International Application No. PCT/AU2021/050690 (undated), 12 pages.

Extended European Search Report mailed May 29, 2024 in European Application No. 21831496.1, 10 pages.

Notice of Reasons for Refusal mailed Apr. 1, 2025 in Japanese Application No. 2023-500063, with English Translation, 13 pages.

Communication Pursuant to Article 94(3) EPC mailed Jun. 23, 2025 in European Application No. 21 831 49.1, 7 pages.

First Office Action mailed Jul. 31, 2025 in Chinese Application No. 202180059167.3, with English translation, 22 pages.

* cited by examiner

Nasal cavity

Nasal bone

Lateral nasal
cartilage

Greater alar
cartilage

Nostril

Lip superior

Lip inferior

Hard palate

Soft palate

Oropharynx

Tongue

Epiglottis

Larynx

Vocal folds

Esophagus

Trachea

Frontal
sinus

Nasal bone

Septum
cartilage

Medial
crus of
greater alar
cartilage

Anterior
nasal spine

Frontal
process of
maxilla

Lesser alar
cartilage

Fibrofatty
tissue

Epidermis

Adipose tissue

Nasal bone

Lateral
cartilage

Septum
cartilage

Greater
alar
cartilage

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

EYE MASK SYSTEM

1 CROSS-REFERENCE TO RELATED APPLICATIONS

This application is the U.S. national phase of International Application No. PCT/AU2021/050690 filed Jun. 30, 2021 which designated the U.S. and claims priority to AU 2020902195 filed Jun. 30, 2020 and AU 2020902196 filed Jun. 30, 2020, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH₂O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4j ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motordriven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One aspect of the present technology is an eye mask system configured to be worn on a user's head during sleep, the eye mask system comprising:

an eye mask configured to cover the user's eyes in use;

one or more transducers configured to influence the user's sleep and/or detect characteristics of the user's sleep and/or detect characteristics of the user during sleep; and a positioning and stabilising structure comprising at least one strap configured apply a force to hold the eye mask in an in use position covering the user's eyes during sleep.

In examples: (a) the one or more transducers may comprise one or more sensors configured to detect characteristics of the user's sleep and/or of the user during sleep; (b) the one or more sensors may comprise an EEG sensor; (c) the eye mask system may comprise an ECG sensor; (d) the eye mask system may comprise a heart rate sensor; (e) the eye mask system may comprise an oxygen saturation sensor; (f) the eye mask system may comprise a blood pressure sensor; (g) the eye mask system may comprise an accelerometer; (h) the eye mask system may comprise a temperature sensor; (i) the eye mask system may comprise a body temperature sensor and/or an ambient temperature sensor; and/or (j) the eye mask system may comprise a microphone.

In further examples: (a) one or more sensors may be provided to the eye mask; (b) one or more sensors may be provided to a peripheral component; (c) the eye mask system may be configured to analyse the output of one or more of the sensors and take an action based on the analysis; (d) the eye mask system may be configured to identify sleep characteristics, identify a problem, predict an outcome and/or provide a recommendation based on the analysis; (e) the eye mask system may comprise an artificial intelligence or machine learning module configured to analyse the output of one or more of the sensors; (f) the eye mask system may be configured to detect and/or diagnose a disorder; (g) the eye mask system may be configured to detect sleep disordered breathing; and/or (h) the eye mask system may be configured to detect one or more of an apnea, hypopnea or hyperpnea.

In further examples: (a) the eye mask system may be configured to identify that a user is sleeping; (b) the eye mask system may be configured to identify sleep stages; (c) the eye mask system may be configured to identify REM sleep and non-REM sleep; (d) the eye mask system may be configured to identify light sleep and deep sleep; (f) the eye mask system may be configured to wake the user during light sleep; (g) the eye mask system may be configured to change a sleep state of the user; and/or (h) the eye mask system may be configured to change the sleep state of the user from deep sleep to light sleep without waking the user.

In further examples: (a) the one or more transducers may comprise one or more output transducers configured to influence the user's sleep; (b) the one or more output transducers may comprise one or more output transducers configured to assist the user in falling asleep and/or improve quality of sleep; (c) the eye mask system may be configured to operate one of the output transducers to achieve one or more of longer sleep, deeper sleep, longer deep sleep and longer REM sleep; (d) the one or more output transducers may comprise a sound transducer; (e) the sound transducer may comprise earbuds or over-ear headphones; (f) the sound transducer may comprise bone conduction transducers; (g) the eye mask system may be configured to provide a noise-cancelling effect with the sound transducer; (h) the one or more output transducers may comprise a display; (i) the one or more output transducers may comprise a temperature transducer; (j) the temperature transducer may comprise a heating element; (k) the temperature transducer may comprise a thermoelectric cooler; and/or (l) the one or more output transducers may comprise a scent transducer.

In further examples: (a) the eye mask system is configured to optimise a user's sleep; (b) the eye mask system is configured to assist the user to: fall asleep, stay asleep for longer, achieve a deeper sleep, maintain deep sleep for longer, wake up, wake up at an optimal time and/or wake up gently; (c) the eye mask system is configured to determine a change which, if made, could improve the user's sleep; (d) the eye mask system is configured to receive an input from a sensor, determine and output and operate a transducer; (e) the eye mask system is configured to assist the user to breathe in a manner conducive to relaxation or sleeping; (f) the eye mask system is configured to provide cues to the user to breath; and/or (g) the cues may be provided via a display or via a sound transducer.

In further examples, the eye mask system further comprises any one or more of: (a) a connection port configured to fluidly connect to and receive a pressurised flow of air from an air circuit; (b) a flow generator configured to generate the pressurised flow of air at said therapeutic pressure; (c) a plenum chamber pressurisable to a therapeutic pressure, said plenum chamber sized and structured to receive the flow of air at the therapeutic pressure from the connection port for breathing by a patient; (d) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and (e) a vent to allow a continuous flow of gases exhaled by the patient from an interior of the plenum chamber to ambient, said vent structure being sized and shaped to maintain the therapeutic pressure in the plenum chamber in use.

In further examples: (a) the eye mask system may comprise a cushion module comprising the seal-forming structure and at least partially forming the plenum chamber; and (b) the cushion module may be removably attachable to the eye mask.

In further examples: (a) the eye mask may comprise one or more cushion portions positioned on a user-contacting side of the eye mask; (b) the one or more cushion portions may be formed from any one or more of: textile; fabric; foam; and silicone; (c) the one or more cushion portions may comprise a first cushion portion and a second cushion portion, wherein the first cushion portion has a greater thickness, and/or a greater user-contacting surface, than the second cushion portion, and wherein the first cushion portion is positioned in a portion of the eye mask that exerts a greater force on the user's face in use than the second cushion portion; and (d) the one or more cushion portions may comprise a first cushion portion and a second cushion portion, wherein the first cushion portion has a greater thickness, and/or a greater user-contacting surface, than the second cushion portion, and the first cushion portion is positioned in a portion of the eye mask that contacts a part of the user's face in use that is more sensitive than a part of the user's face contacted in use by the second cushion portion.

Another aspect of one form of the present technology is an eye mask system for treatment of sleep disordered breathing, the eye mask system comprising:

an eye mask configured to cover the user's eyes in use;

one or more transducers configured to influence the user's sleep and/or detect characteristics of the user's sleep and/or detect characteristics of the user during sleep;

wherein the eye mask system further comprises one of:

a connection port configured to fluidly connect to and receive a pressurised flow of air at a therapeutic pressure for breathing by the user from an air circuit; or a flow generator configured to generate the pressurised flow of air at said therapeutic pressure, wherein the eye mask system further comprises:

a plenum chamber pressurisable to a therapeutic pressure, said plenum chamber sized and structured to receive the flow of air at the therapeutic pressure from the connection port for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a vent to allow a continuous flow of gases exhaled by the patient from an interior of the plenum chamber to ambient, said vent structure being sized and shaped to maintain the therapeutic pressure in the plenum chamber in use.

In examples: (a) the eye mask system comprises a cushion module comprising the seal-forming structure and at least partially forming the plenum chamber; (b) the cushion module is removably attachable to the eye mask; (c) the cushion module is able to move relative to the eye mask; (d) the cushion module is able to be moved relative to the eye mask; (e) the cushion module is at least partially decoupled from the eye mask; (f) the cushion module is able to change position with respect to the eye mask; (g) the eye mask system comprises an actuator to move the cushion module; (h) the cushion module is able to translate with respect to the eye mask along an anterior-posterior axis; (i) the cushion module is able to translate with respect to the eye mask along a left-right axis; (j) the cushion module is able to translate with respect to the eye mask along a superior-inferior axis; (k) the cushion module is able to change orientation with respect to the eye mask; (l) the cushion module is able to rotate with respect to the eye mask about a left-right axis; (m) the cushion module is able to rotate with respect to the eye mask about an anterior-posterior axis; (n) the cushion module is able to rotate with respect to the eye mask about a superior-inferior axis; (o) the cushion module is movable between a non-contact position and a sealing position.

In further examples: (a) the eye mask comprises the connection port, the connection port being located at a central and anterior location on the eye mask; (b) the connection port is located at a superior location on the patient's head, and the eye mask system comprises a pair of headgear tubes fluidly connecting the connection port to the eye mask; (c) the seal-forming structure is configured to seal to about an inferior periphery of the patient's nose; (d) the seal-forming structure comprises a pair of nasal pillows; (e) the seal-forming structure comprises a nasal cushion configured to seal around the patient's nose including to a surface of the patient's nose superior to the patient's nose tip; (f) the seal-forming structure comprises a full-face cushion configured to seal around the patient's nose and mouth including to a surface of the patient's nose superior to the patient's nose tip.

In further examples: (a) the eye mask system is configured to detect that the user is awake and operate in a sleep-assist mode; (b) the eye mask system is configured to detect that the user is asleep and operate in a sleep mode; (c) the eye mask system is configured to begin respiratory pressure therapy upon a change from the sleep-assist mode to the sleep mode; (d) the eye mask system is configured to move a cushion module from a non-contact position into a sealing position upon a change from a sleep-assist mode to the sleep mode.

Another aspect of one form of the present technology is an eye mask system for treatment of sleep disordered breathing, the eye mask system comprising:

an eye mask configured to cover the user's eyes in use;

one or more transducers configured to influence the user's sleep and/or detect characteristics of the user's sleep and/or detect characteristics of the user during sleep;

a flow generator configured to provide a pressurised flow of air;

a plenum chamber pressurisable to a therapeutic pressure, said plenum chamber sized and structured to receive the flow of air at the therapeutic pressure from the flow generator for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a vent to allow a continuous flow of gases exhaled by the patient from an interior of the plenum chamber to ambient, said vent structure being sized and shaped to maintain the therapeutic pressure in the plenum chamber in use.

In examples: (a) the eye mask system comprises a cushion module comprising the seal-forming structure and at least partially forming the plenum chamber; (b) the cushion module is removably attachable to the eye mask; (c) the cushion module is able to move relative to the eye mask; (d) the cushion module is able to be moved relative to the eye mask; (e) the cushion module is at least partially decoupled from the eye mask; (f) the cushion module is able to change position with respect to the eye mask; (g) the eye mask system comprises an actuator to move the cushion module; (h) the cushion module is able to translate with respect to the eye mask along an anterior-posterior axis; (i) the cushion module is able to translate with respect to the eye mask along a left-right axis; (j) the cushion module is able to translate with respect to the eye mask along a superior-inferior axis; (k) the cushion module is able to change orientation with respect to the eye mask; (l) the cushion module is able to rotate with respect to the eye mask about a left-right axis; (m) the cushion module is able to rotate with respect to the eye mask about an anterior-posterior axis; (n) the cushion module is able to rotate with respect to the eye mask about a superior-inferior axis; (o) the cushion module is movable between a non-contact position and a sealing position.

In further examples: (a) the seal-forming structure is configured to seal to about an inferior periphery of the patient's nose; (b) the seal-forming structure comprises a pair of nasal pillows; (c) the seal-forming structure comprises a nasal cushion configured to seal around the patient's nose including to a surface of the patient's nose superior to the patient's nose tip; (d) the seal-forming structure comprises a full-face cushion configured to seal around the patient's nose and mouth including to a surface of the patient's nose superior to the patient's nose tip.

In further examples: (a) the eye mask system is configured to detect that the user is awake and operate in a sleep-assist mode; (b) the eye mask system is configured to detect that the user is asleep and operate in a sleep mode; (c) the eye mask system is configured to begin respiratory pressure therapy upon a change from the sleep-assist mode to the sleep mode; (d) the eye mask system is configured to move a cushion module from a non-contact position into a sealing position upon a change from a sleep-assist mode to the sleep mode.

One aspect of the present technology is an eye mask system configured to be worn on a user's head, the eye mask system comprising:

an eye mask configured to cover the user's eyes in use;

one or more transducers configured to interface with the user and/or the ambient environment; and a positioning and stabilising structure comprising at least one strap configured apply a force to hold the eye mask in an in-use position covering the user's eyes.

In examples: (a) the at least one strap is configured to hold the eye mask in an in-use position covering the user's eyes during sleep; and/or (b) the one or more transducers are configured to influence the user's sleep and/or detect characteristics of the user's sleep and/or detect characteristics of the user during sleep.

In examples: (a) the one or more transducers may comprise one or more sensors; (b) the one or more sensors may comprise an EEG sensor; (c) the eye mask system may comprise an ECG sensor; (d) the eye mask system may comprise a heart rate sensor; (e) the eye mask system may comprise an oxygen saturation sensor; (f) the eye mask system may comprise a blood pressure sensor; (g) the eye mask system may comprise an accelerometer; (h) the eye mask system may comprise a temperature sensor; (i) the eye mask system may comprise a body temperature sensor and/or an ambient temperature sensor; and/or (j) the eye mask system may comprise a microphone.

In further examples: (a) one or more sensors may be provided to the eye mask; (b) one or more sensors may be provided to a peripheral component; (c) the eye mask system may be configured to analyse the output of one or more of the sensors and take an action based on the analysis; (d) the eye mask system may comprise an artificial intelligence or machine learning module configured to analyse the output of one or more of the sensors.

In further examples: (a) the one or more transducers may comprise one or more output transducers; (b) the one or more output transducers may comprise a sound transducer; (c) the sound transducer may comprise earbuds or over-ear headphones; (d) the sound transducer may comprise bone conduction transducers; (e) the eye mask system may be configured to provide a noise-cancelling effect with the sound transducer; (f) the eye mask system may comprise a display; (g) the eye mask system may comprise a temperature transducer; (h) the temperature transducer may comprise a heating element; (i) the temperature transducer may comprise a thermoelectric cooler; and/or (j) the eye mask system may comprise a scent transducer.

In further examples, the eye mask system comprises:

a plenum chamber pressurisable to a therapeutic pressure, said plenum chamber sized and structured to receive the flow of air at the therapeutic pressure from the connection port for breathing by a patient;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a vent to allow a continuous flow of gases exhaled by the patient from an interior of the plenum chamber to ambient, said vent structure being sized and shaped to maintain the therapeutic pressure in the plenum chamber in use.

In further examples: (a) the eye mask system is configured to operate in a setup mode in which the eye mask system is configured to assist the user to setup and/or begin using the eye mask system as a patient interface; (b) the eye mask system is configured to present a tutorial to the user to assist the user with setup; (c) the eye mask system is configured to assist the user to fit the eye mask system correctly for use as a patient interface for respiratory pressure treatment of sleep disordered breathing; and/or (d) the eye mask system is configured to provide instructions regarding troubleshooting.

In further examples: (a) the eye mask system is configured to monitor one or more signals received from one or more sensors during setup and provide feedback to the user regarding setup based on the one or more signals; (b) the eye mask system comprises a strap tension sensor; and/or (c) the eye mask system is configured to measure tension in a backstrap of the eye mask system with the strap tension sensor and provide feedback to the user based on the tension.

In further examples: (a) the eye mask system is configured to detect a leak during use of the eye mask system for respiratory pressure therapy; (b) the eye mask system is configured to alert the user to the existence of the leak; (c) the eye mask system is configured to determine a location of a leak; (d) the eye mask system is configured to provide an indication of the location of the leak to the user; and/or (e) the eye mask system is configured to provide instructions regarding reducing or eliminating the leak based on the location of the leak.

In further examples: (a) the eye mask system is configured to prompt the user to assist the user to breathe in a manner conducive to relaxation; (b) the eye mask system is configured to provide cues to the user to breathe; (c) the cues may be provided via a display or via a sound transducer; (d) the eye mask system is configured to monitor the patient's adherence to the breathing cues using one or more sensors; (e) the eye mask system is configured to provide positive airway pressure via the plenum chamber and seal-forming structure while providing the cues; (f) the eye mask system is configured to increase positive airway pressure to a therapy pressure from a lower pressure than the therapy pressure.

In further examples: (a) the eye mask may comprise one or more cushion portions positioned on a user-contacting side of the eye mask; (b) the one or more cushion portions may be formed from any one or more of: textile; fabric; foam; and silicone; (c) the one or more cushion portions may comprise a first cushion portion and a second cushion portion, wherein the first cushion portion has a greater thickness, and/or a greater user-contacting surface, than the second cushion portion, and wherein the first cushion portion is positioned in a portion of the eye mask that exerts a greater force on the user's face in use than the second cushion portion; and (d) the one or more cushion portions may comprise a first cushion portion and a second cushion portion, wherein the first cushion portion has a greater thickness, and/or a greater user-contacting surface, than the second cushion portion, and the first cushion portion is positioned in a portion of the eye mask that contacts a part of the user's face in use that is more sensitive than a part of the user's face contacted in use by the second cushion portion.

Another aspect of one form of the present technology is an eye mask system for providing respiratory pressure therapy to a user for treatment of sleep disordered breathing, the eye mask system comprising:

an eye mask configured to cover the user's eyes in use;
one or more transducers configured to influence the user's sleep and/or detect characteristics of the user's sleep and/or detect characteristics of the user during sleep;
wherein the eye mask system further comprises one of:
   a connection port configured to fluidly connect to and receive a pressurised flow of air at a therapeutic pressure for breathing by a patient from an air circuit; or
   a flow generator configured to generate the pressurised flow of air at said therapeutic pressure,
wherein the eye mask system further comprises:
   a plenum chamber pressurisable to a therapeutic pressure, said plenum chamber sized and structured to receive the flow of air at said therapeutic pressure,
   a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and
   a vent to allow a continuous flow of gases exhaled by the patient from an interior of the plenum chamber to ambient, said vent structure being sized and shaped to maintain the therapeutic pressure in the plenum chamber in use,
wherein the eye mask system is configured to operate in at least two modes: a non-treatment mode in which respiratory pressure therapy is not provided to the user, and a treatment mode in which respiratory pressure therapy is provided to the user for treatment of sleep disordered breathing.

In examples: (a) the one or more transducers may comprise one or more sensors configured to detect characteristics of the user's sleep and/or of the user during sleep; (b) the one or more sensors may comprise an EEG sensor; (c) the eye mask system may comprise an ECG sensor; (d) the eye mask system may comprise a heart rate sensor; (e) the eye mask system may comprise an oxygen saturation sensor; (f) the eye mask system may comprise a blood pressure sensor; (g) the eye mask system may comprise an accelerometer; (h) the eye mask system may comprise a temperature sensor; (i) the eye mask system may comprise a body temperature sensor and/or an ambient temperature sensor; and/or (j) the eye mask system may comprise a microphone.

In further examples: (a) one or more sensors may be provided to the eye mask; (b) one or more sensors may be provided to a peripheral component; (c) the eye mask system may be configured to analyse the output of one or more of the sensors; (d) the eye mask system is configured to take an action based on the analysis; (e) the eye mask system may be configured to identify sleep characteristics, identify a problem, predict an outcome and/or provide a recommendation based on the analysis; (f) the eye mask system may comprise an artificial intelligence or machine learning module configured to analyse the output of one or more of the sensors; (g) the eye mask system may be configured to detect and/or diagnose a disorder; (h) the eye mask system may be configured to detect sleep disordered breathing; (i) the eye mask may be configured to detect sleep disordered breathing in at least the non-treatment mode; (j) the eye mask system may be configured to detect one or more of an apnea, hypopnea, hyperpnea, snoring or gasping in at least the non-treatment mode; and/or (k) the eye mask system is configured to detect sleep disordered breathing in the non-treatment mode and switch from the non-treatment mode to the treatment mode upon detection of sleep disordered breathing.

In further examples: (a) the one or more transducers may comprise one or more output transducers configured to influence the user's sleep; (b) the one or more output transducers may comprise one or more output transducers configured to assist the user in falling asleep and/or improve quality of sleep; (c) the eye mask system may be configured to operate one of the output transducers to achieve one or more of longer sleep, deeper sleep, longer deep sleep and longer REM sleep; (d) the one or more output transducers may comprise a sound transducer; (e) the sound transducer may comprise earbuds or over-ear headphones; (f) the sound transducer may comprise bone conduction transducers; (g) the eye mask system may be configured to provide a noise-cancelling effect with the sound transducer; (h) the one or more output transducers may comprise a display; (i) the one or more output transducers may comprise a temperature transducer; (j) the temperature transducer may comprise a heating element; (k) the temperature transducer may comprise a thermoelectric cooler; and/or (l) the one or more output transducers may comprise a scent transducer.

In further examples: (a) the eye mask system is configured to optimise a user's sleep; (b) the eye mask system is configured to assist the user to: fall asleep, stay asleep for longer, achieve a deeper sleep, maintain deep sleep for longer, wake up, wake up at an optimal time and/or wake up gently; (c) the eye mask system is configured to determine a change which, if made, could improve the user's sleep; (d) the eye mask system is configured to receive an input from a sensor, determine and output and operate a transducer; (e) the eye mask system is configured to assist the user to breathe in a manner conducive to relaxation or sleeping; (f) the eye mask system is configured to provide cues to the user to breath; and/or (g) the cues may be provided via a display or via a sound transducer.

In examples: (a) the eye mask system comprises a cushion module comprising the seal-forming structure and at least partially forming the plenum chamber; (b) the cushion module is removably attachable to the eye mask; (c) the cushion module is able to move relative to the eye mask; (d) the cushion module is able to be moved relative to the eye mask; (e) the cushion module is at least partially decoupled from the eye mask; (f) the cushion module is able to change position with respect to the eye mask; (g) the eye mask system comprises an actuator to move the cushion module;

(h) the cushion module is able to translate with respect to the eye mask along an anterior-posterior axis; (i) the cushion module is able to translate with respect to the eye mask along a left-right axis; (j) the cushion module is able to translate with respect to the eye mask along a superior-inferior axis; (k) the cushion module is able to change orientation with respect to the eye mask; (l) the cushion module is able to rotate with respect to the eye mask about a left-right axis; (m) the cushion module is able to rotate with respect to the eye mask about an anterior-posterior axis; (n) the cushion module is able to rotate with respect to the eye mask about a superior-inferior axis; (o) the seal-forming structure is moveable between a non-contact position in which the seal-forming structure does not contact the user and a sealing position in which the seal-forming structure is able to form a seal to the user's face; (p) the cushion module is movable between a non-contact position in which the seal-forming structure does not contact the user and a sealing position in which the seal-forming structure is able to form a seal to the user's face.

In further examples: (a) the eye mask comprises the connection port, the connection port being located at a central and anterior location on the eye mask; (b) the connection port is located at a superior location on the patient's head, and the eye mask system comprises a pair of headgear tubes fluidly connecting the connection port to the eye mask; (c) the seal-forming structure is configured to seal to about an inferior periphery of the patient's nose; (d) the seal-forming structure comprises a pair of nasal pillows; (e) the seal-forming structure comprises a nasal cushion configured to seal around the patient's nose including to a surface of the patient's nose superior to the patient's nose tip; (f) the seal-forming structure comprises a full-face cushion configured to seal around the patient's nose and mouth including to a surface of the patient's nose superior to the patient's nose tip.

In further examples: (a) the eye mask system is configured to detect that the user is awake and operate in the non-treatment mode; (b) the eye mask system is configured to detect that the user is asleep and operate in the treatment mode; (c) the eye mask system is configured to begin respiratory pressure therapy upon a change from the non-treatment mode to the treatment mode; (d) the eye mask system is configured to move the seal-forming structure from a non-contact position into a sealing position upon a change from the non-treatment mode to the treatment mode.

In further examples: (a) the eye mask system is configured to prompt the user to assist the user to breathe in a manner conducive to relaxation; (b) the eye mask system is configured to provide cues to the user to breathe; (c) the cues may be provided via a display or via a sound transducer; (d) the eye mask system is configured to monitor the patient's adherence to the breathing cues using one or more sensors; (e) the eye mask system is configured to provide positive airway pressure via the plenum chamber and seal-forming structure while providing the cues; (f) the eye mask system is configured to increase positive airway pressure to a therapy pressure from a lower pressure than the therapy pressure.

Another aspect of one form of the present technology is an eye mask system for providing respiratory pressure therapy to a user for treatment of sleep disordered breathing, the eye mask system comprising:

an eye mask configured to cover the user's eyes in use;

one or more transducers configured to influence the user's sleep and/or detect characteristics of the user's sleep and/or detect characteristics of the user during sleep;

wherein the eye mask system further comprises one of:

a connection port configured to fluidly connect to and receive a pressurised flow of air at a therapeutic pressure for breathing by a patient from an air circuit; or a flow generator configured to generate the pressurised flow of air at said therapeutic pressure, wherein the eye mask system further comprises:

a plenum chamber pressurisable to a therapeutic pressure, said plenum chamber sized and structured to receive the flow of air at said therapeutic pressure, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a vent to allow a continuous flow of gases exhaled by the patient from an interior of the plenum chamber to ambient, said vent structure being sized and shaped to maintain the therapeutic pressure in the plenum chamber in use, wherein the eye mask system is configured to assist the user to fall asleep and/or remain asleep during respiratory pressure therapy.

In examples: (a) the one or more transducers may comprise one or more sensors configured to detect characteristics of the ambient environment, of the user's sleep and/or of the user during sleep; (b) the one or more sensors may comprise an EEG sensor; (c) the eye mask system may comprise an ECG sensor; (d) the eye mask system may comprise a heart rate sensor; (e) the eye mask system may comprise an oxygen saturation sensor; (f) the eye mask system may comprise a blood pressure sensor; (g) the eye mask system may comprise an accelerometer; (h) the eye mask system may comprise a temperature sensor; (i) the eye mask system may comprise a body temperature sensor and/or an ambient temperature sensor; and/or (j) the eye mask system may comprise a microphone.

In further examples: (a) one or more sensors may be provided to the eye mask; (b) one or more sensors may be provided to a peripheral component; (c) the eye mask system may be configured to analyse the output of one or more of the sensors and take an action based on the analysis; (d) the eye mask system may be configured to identify sleep characteristics, identify a problem, predict an outcome and/or provide a recommendation based on the analysis; (e) the eye mask system may comprise an artificial intelligence or machine learning module configured to analyse the output of one or more of the sensors; (f) the eye mask system may be configured to detect and/or diagnose a disorder; (g) the eye mask system may be configured to detect sleep disordered breathing; and/or (h) the eye mask system may be configured to detect one or more of an apnea, hypopnea or hyperpnea.

In further examples: (a) the eye mask system may be configured to identify that a user is sleeping; (b) the eye mask system may be configured to identify sleep stages; (c) the eye mask system may be configured to identify REM sleep and non-REM sleep; (d) the eye mask system may be configured to identify light sleep and deep sleep; (f) the eye mask system may be configured to wake the user during light sleep; (g) the eye mask system may be configured to change a sleep state of the user; and/or (h) the eye mask system may be configured to change the sleep state of the user from deep sleep to light sleep without waking the user.

In further examples: (a) the one or more transducers may comprise one or more output transducers configured to influence the user's sleep; (b) the one or more output transducers may comprise one or more output transducers configured to assist the user in falling asleep and/or improve quality of sleep; (c) the eye mask system may be configured to operate one of the output transducers to achieve one or more of longer sleep, deeper sleep, longer deep sleep and longer REM sleep; (d) the one or more output transducers may comprise a sound transducer; (e) the sound transducer may comprise earbuds or over-ear headphones; (f) the sound transducer may comprise bone conduction transducers; (g) the eye mask system may be configured to provide a noise-cancelling effect with the sound transducer; (h) the one or more output transducers may comprise a display; (i) the one or more output transducers may comprise a temperature transducer; (j) the temperature transducer may comprise a heating element; (k) the temperature transducer may comprise a thermoelectric cooler; and/or (l) the one or more output transducers may comprise a scent transducer.

In further examples: (a) the eye mask system is configured to optimise a user's sleep; (b) the eye mask system is configured to assist the user to: fall asleep, stay asleep for longer, achieve a deeper sleep, maintain deep sleep for longer, wake up, wake up at an optimal time and/or wake up gently; (c) the eye mask system is configured to determine a change which, if made, could improve the user's sleep; (d) the eye mask system is configured to receive an input from a sensor, determine and output and operate a transducer; (e) the eye mask system is configured to assist the user to breathe in a manner conducive to relaxation or sleeping; (f) the eye mask system is configured to provide cues to the user to breath; and/or (g) the cues may be provided via a display or via a sound transducer.

In further examples: (a) the eye mask system is configured to detect that the user is awake and operate in a sleep-assist mode; (b) the eye mask system is configured to detect that the user is asleep and operate in a sleep mode; (c) the eye mask system is configured to begin respiratory pressure therapy upon a change from the sleep-assist mode to the sleep mode; (d) the eye mask system is configured to move a cushion module from a non-contact position into a sealing position upon a change from a sleep-assist mode to the sleep mode.

In further examples: (a) the one or more transducers comprise one or more sensors configured to detect characteristics of the ambient environment, of the user's sleep and/or of the user; (b) the eye mask system is configured to determine a change which, if made, could assist the user to fall asleep and/or remain asleep; (c) the eye mask system is configured to adjust the therapeutic pressure of the flow of air based on an output of one or more of the sensors; (d) the eye mask system is configured to detect that the user is waking up and reduce the therapeutic pressure; (e) the eye mask system is configured to reduce therapeutic pressure upon detection of ambient noise above a predetermined threshold; (f) the eye mask system comprises a microphone and a sound transducer; (g) the eye mask system is configured to provide a noise cancelling effect using the sound transducer upon detection of ambient noise above a predetermined threshold; (h) the eye mask system is configured to provide the noise cancelling effect using the sound transducer upon detection that the user is waking up; (i) the one or more transducers comprise one or more output transducers configured to influence the user's sleep; and/or (j) the one or more output transducers are configured to assist the user in falling asleep, assist the user in remaining asleep and/or improve quality of sleep.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

4.2 Respiratory System and Facial Anatomy

Figure 1:
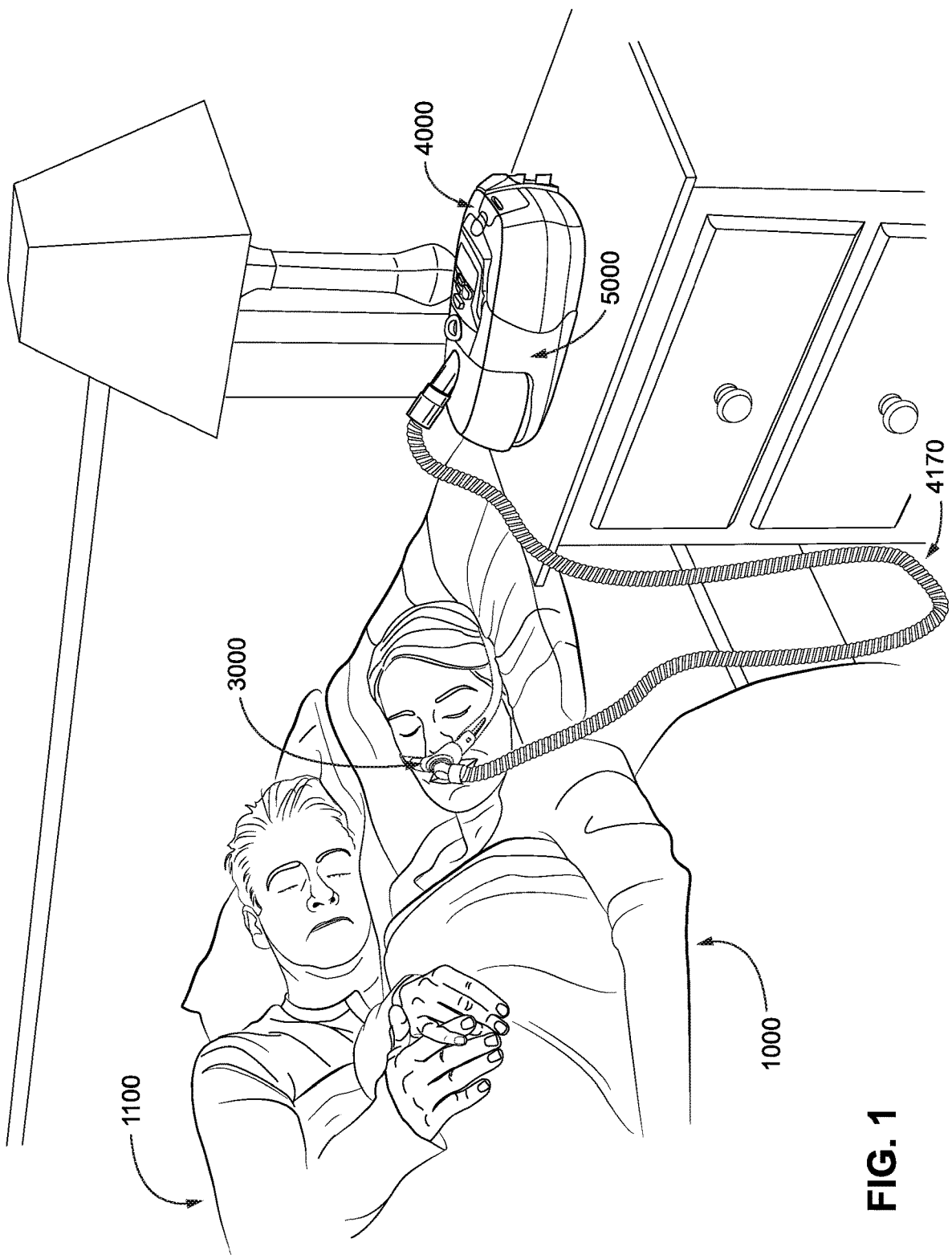
Figure 2A:
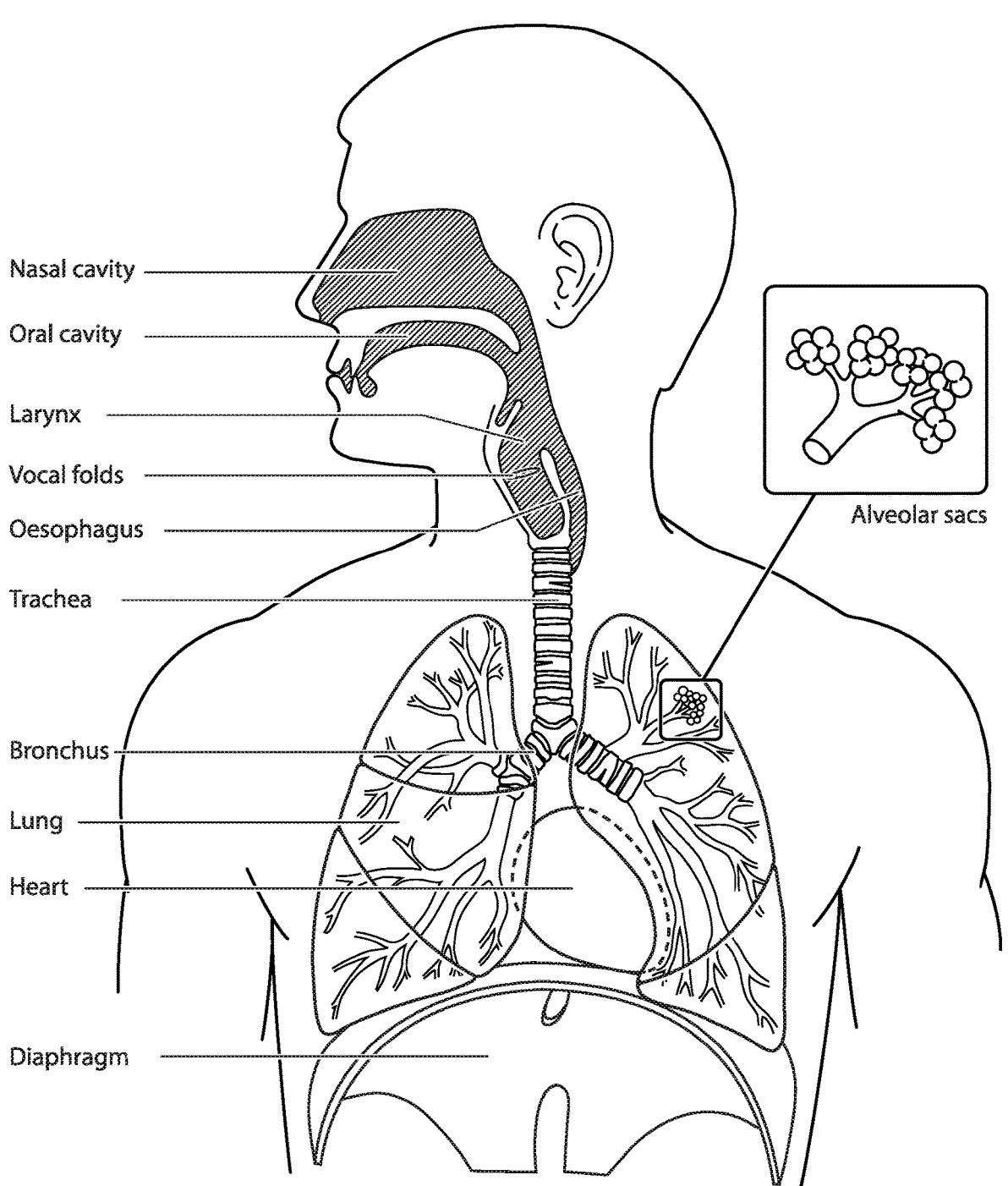
FIG. 2A shows an overview of a human respiratory system including the nasal and oral cavities, the larynx, vocal folds, oesophagus, trachea, bronchus, lung, alveolar sacs, heart and diaphragm.
Figure 2B:
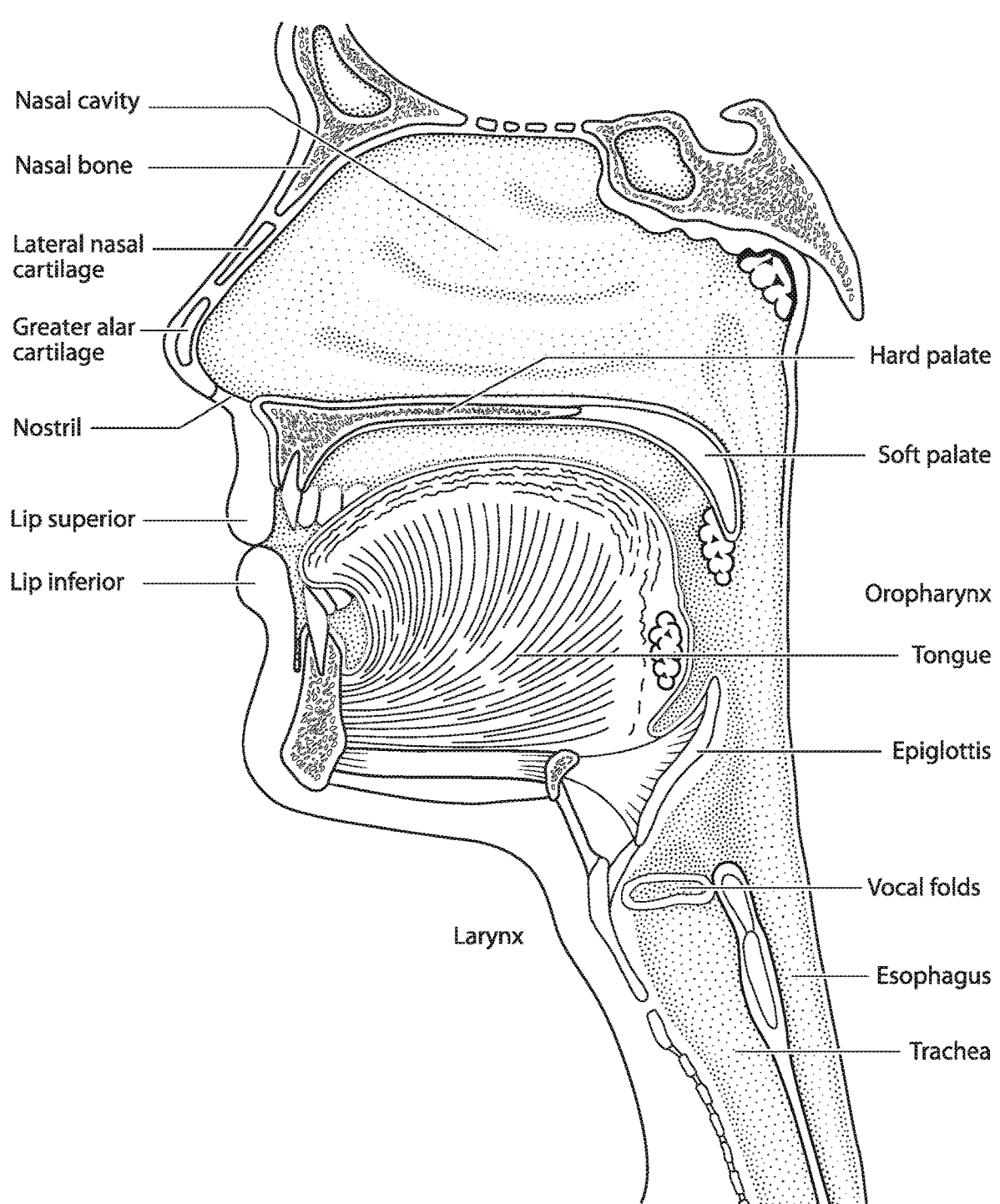
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
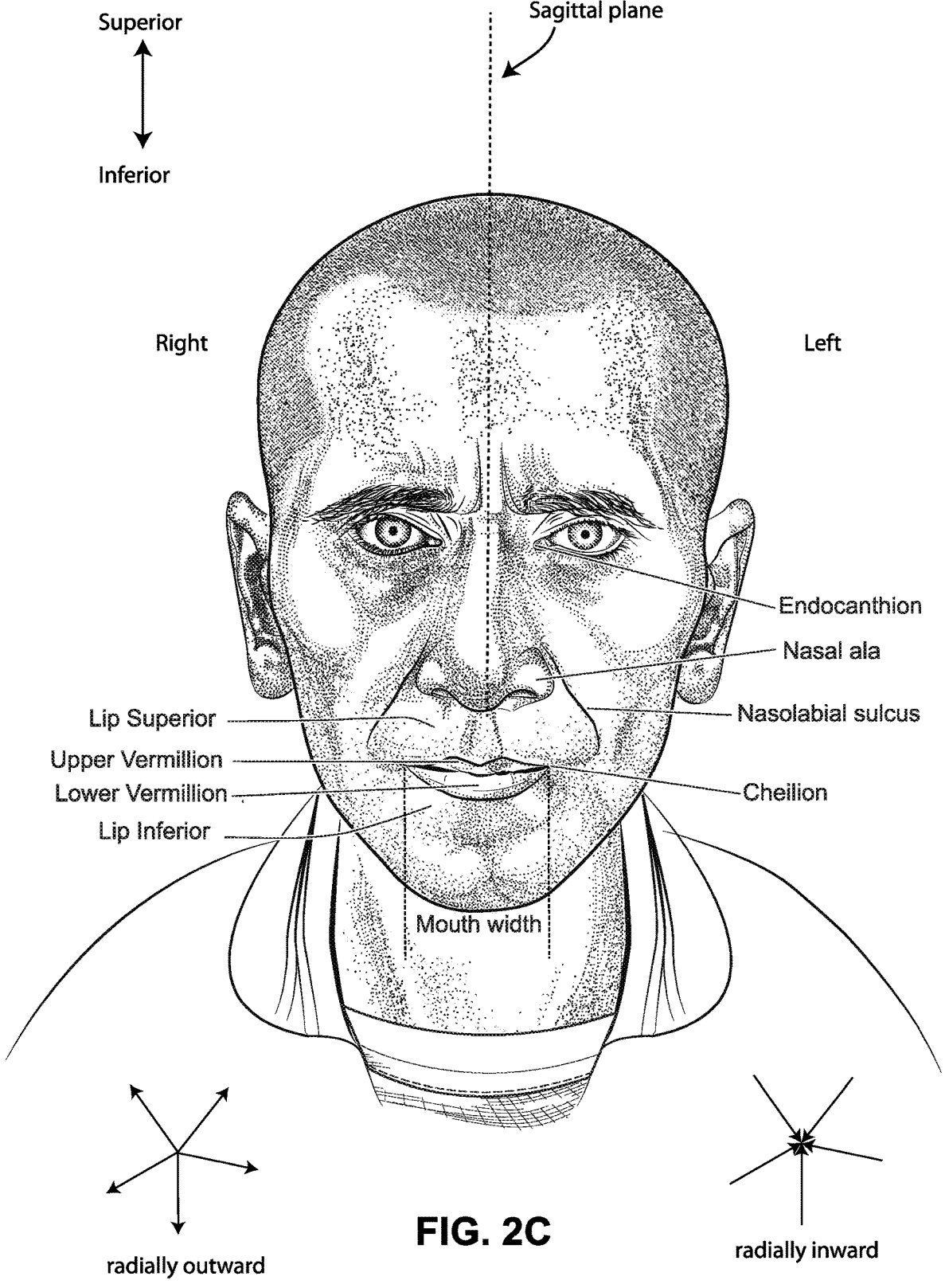
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
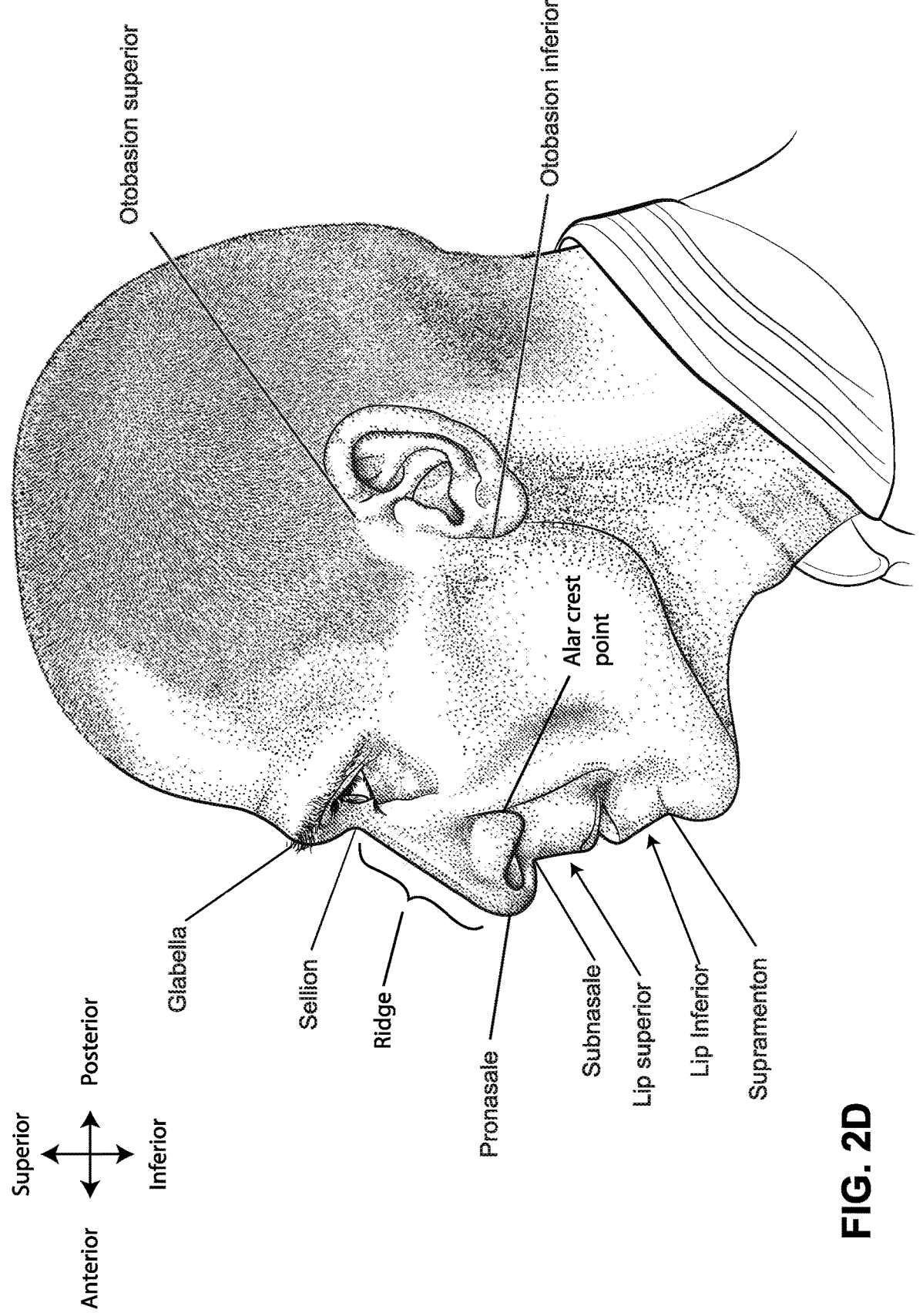
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
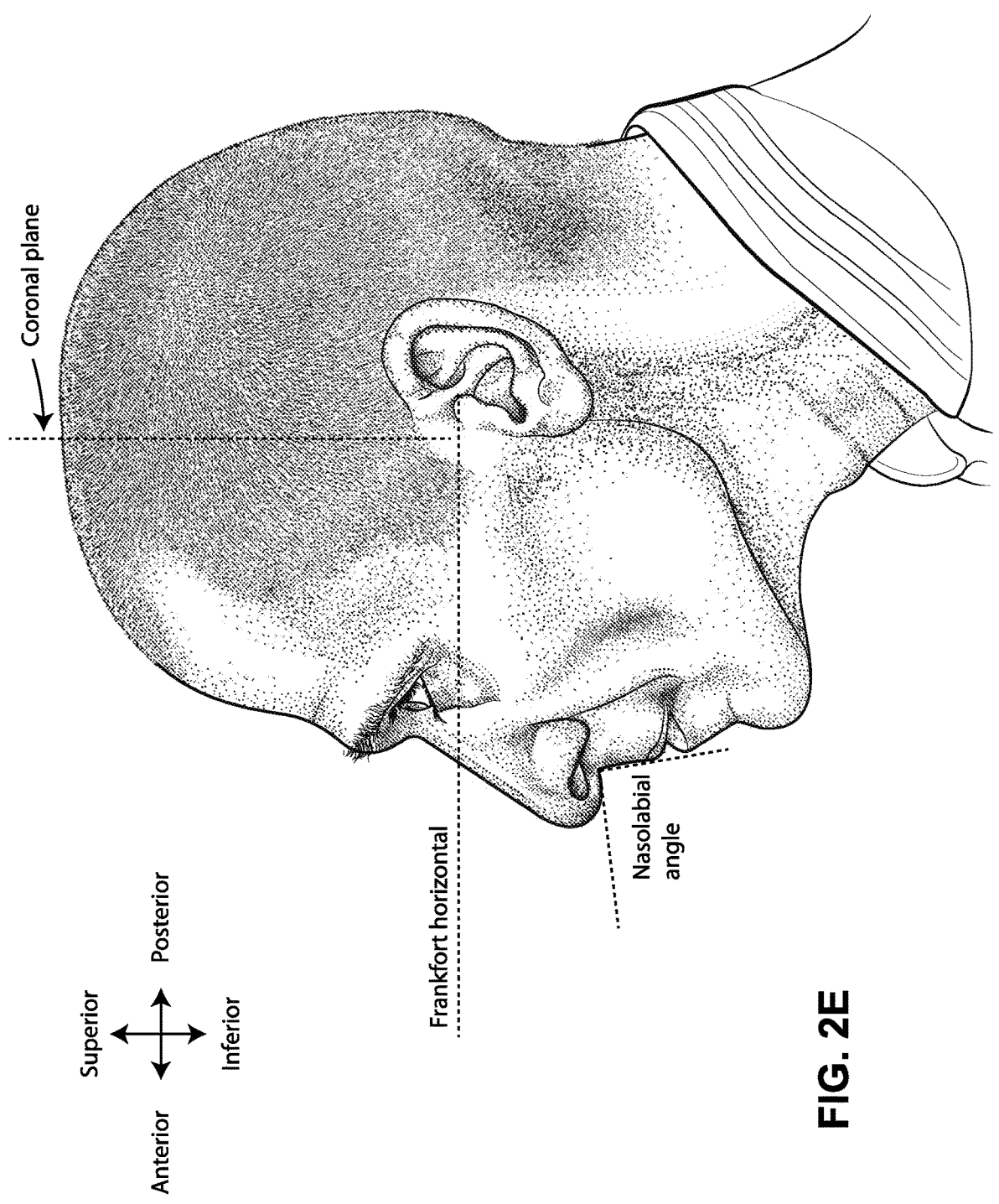

FIG. 2E is a further side view of a head. The approximate locations of the Frankfort horizontal and nasolabial angle are indicated. The coronal plane is also indicated.

Figure 2F:
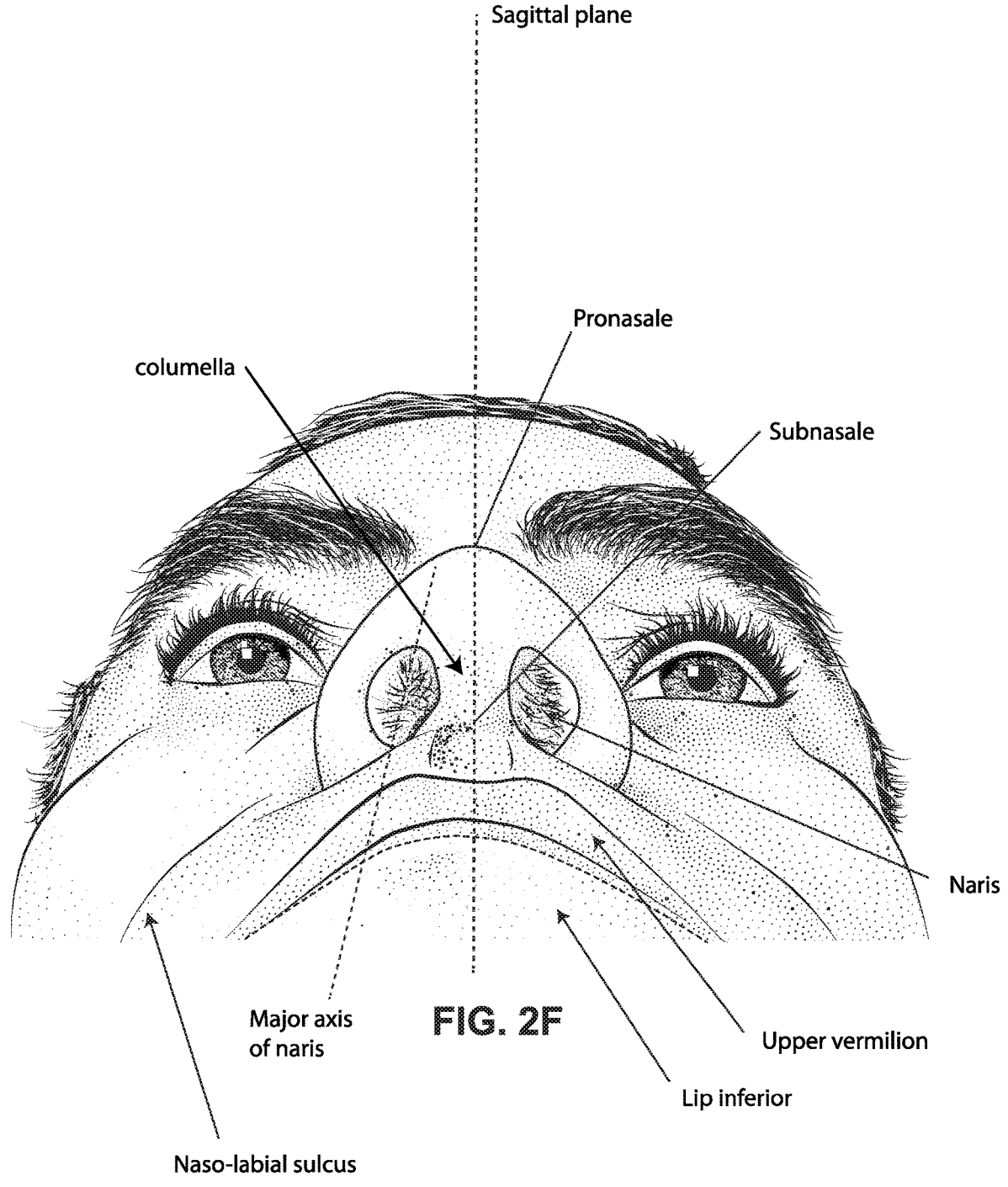

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
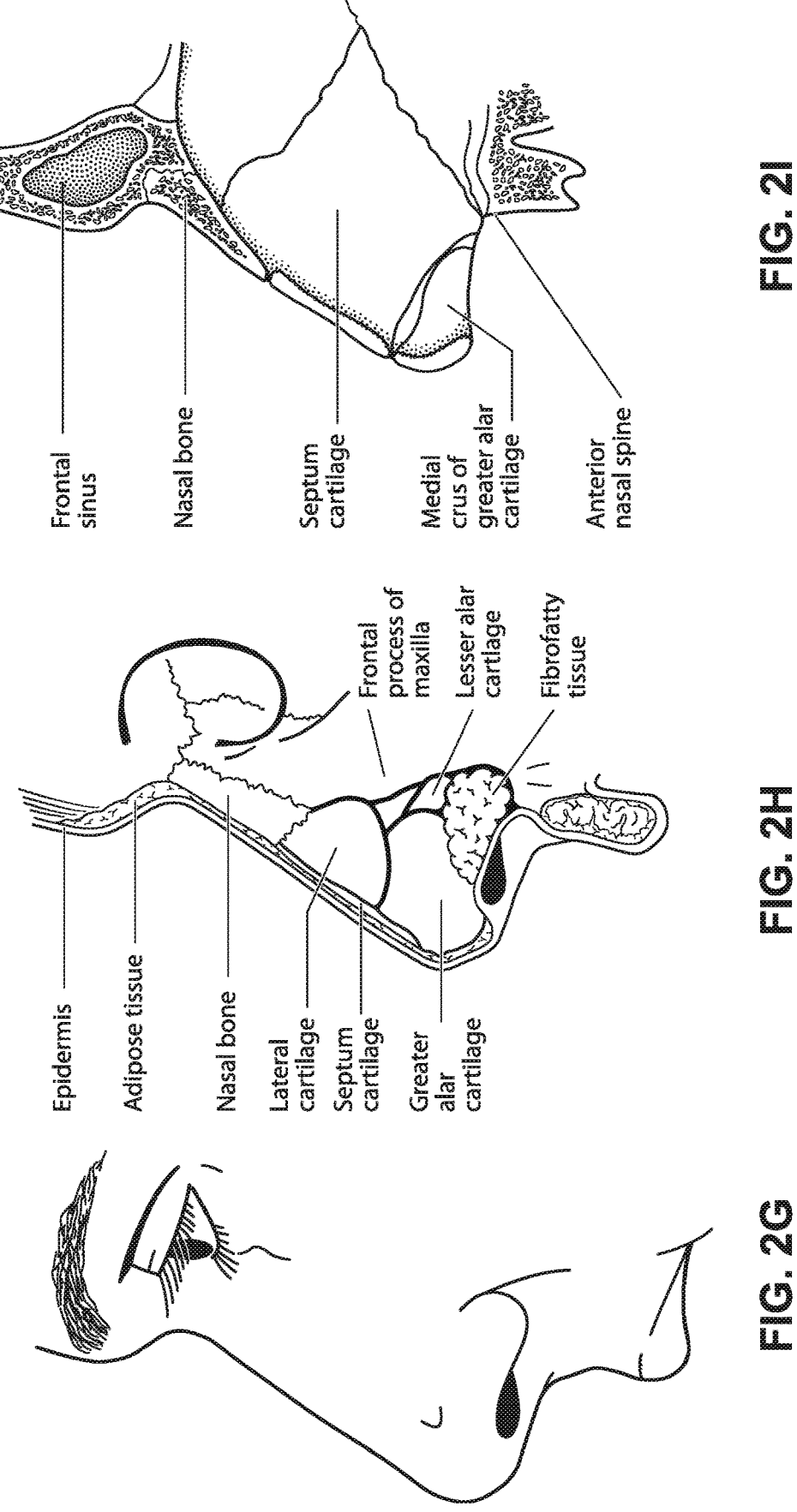

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
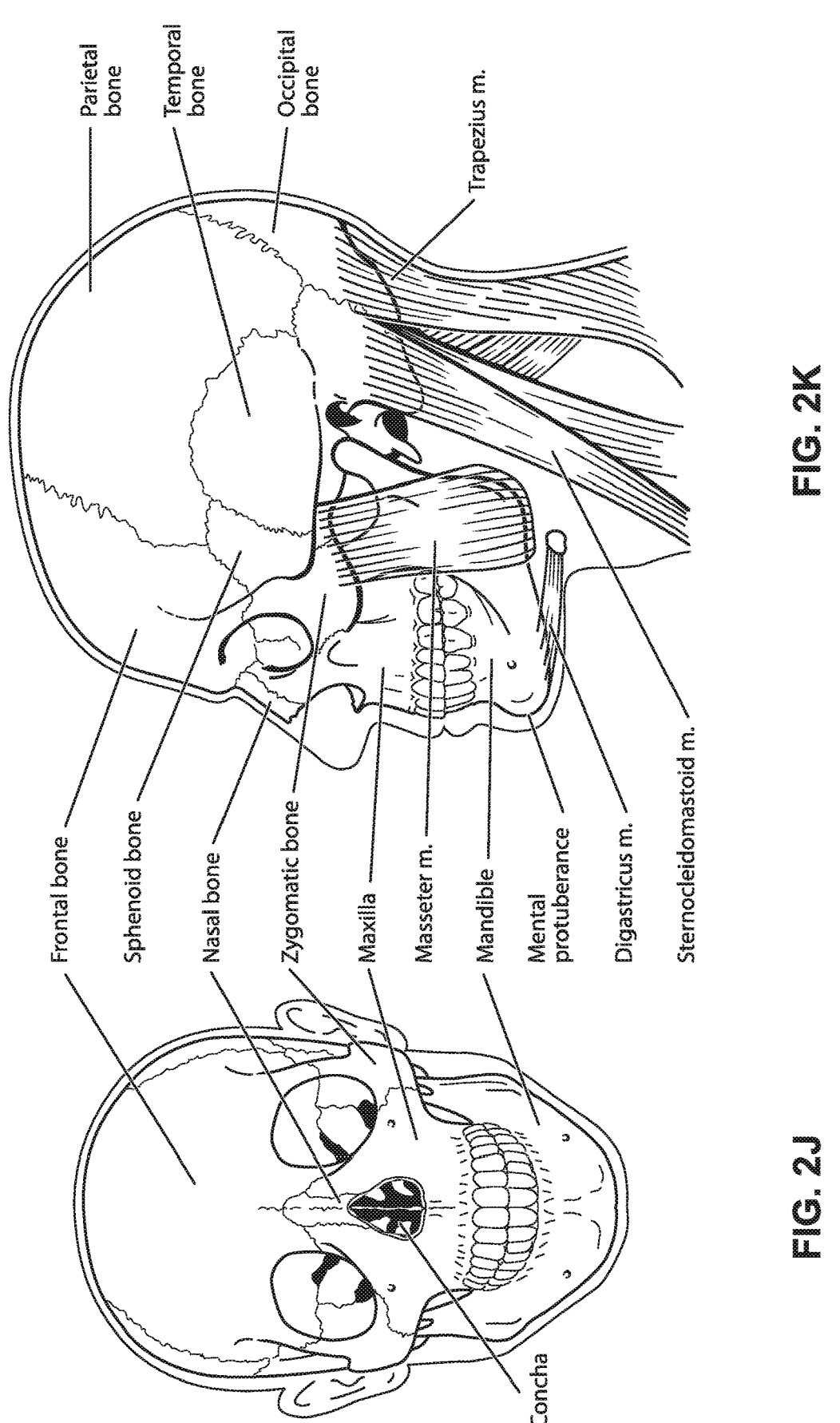

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
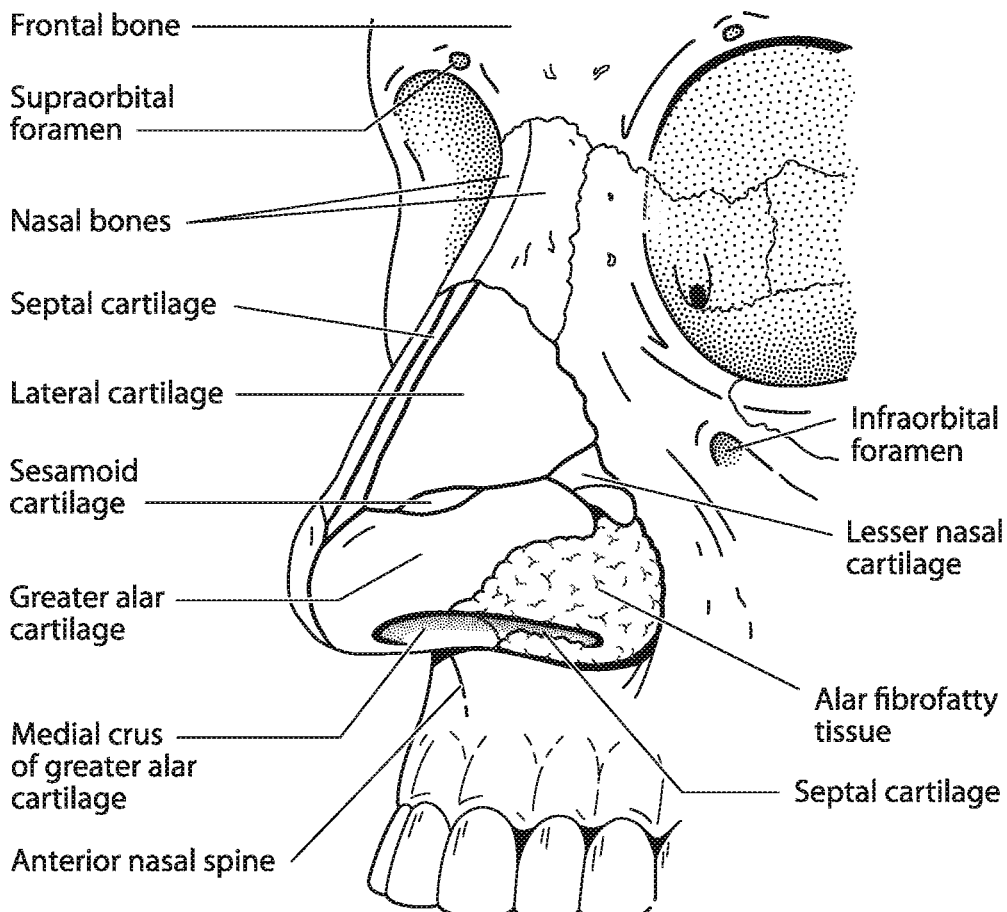

FIG. 2L shows an anterolateral view of a nose.

4.3 Patient Interface

Figure 3A:
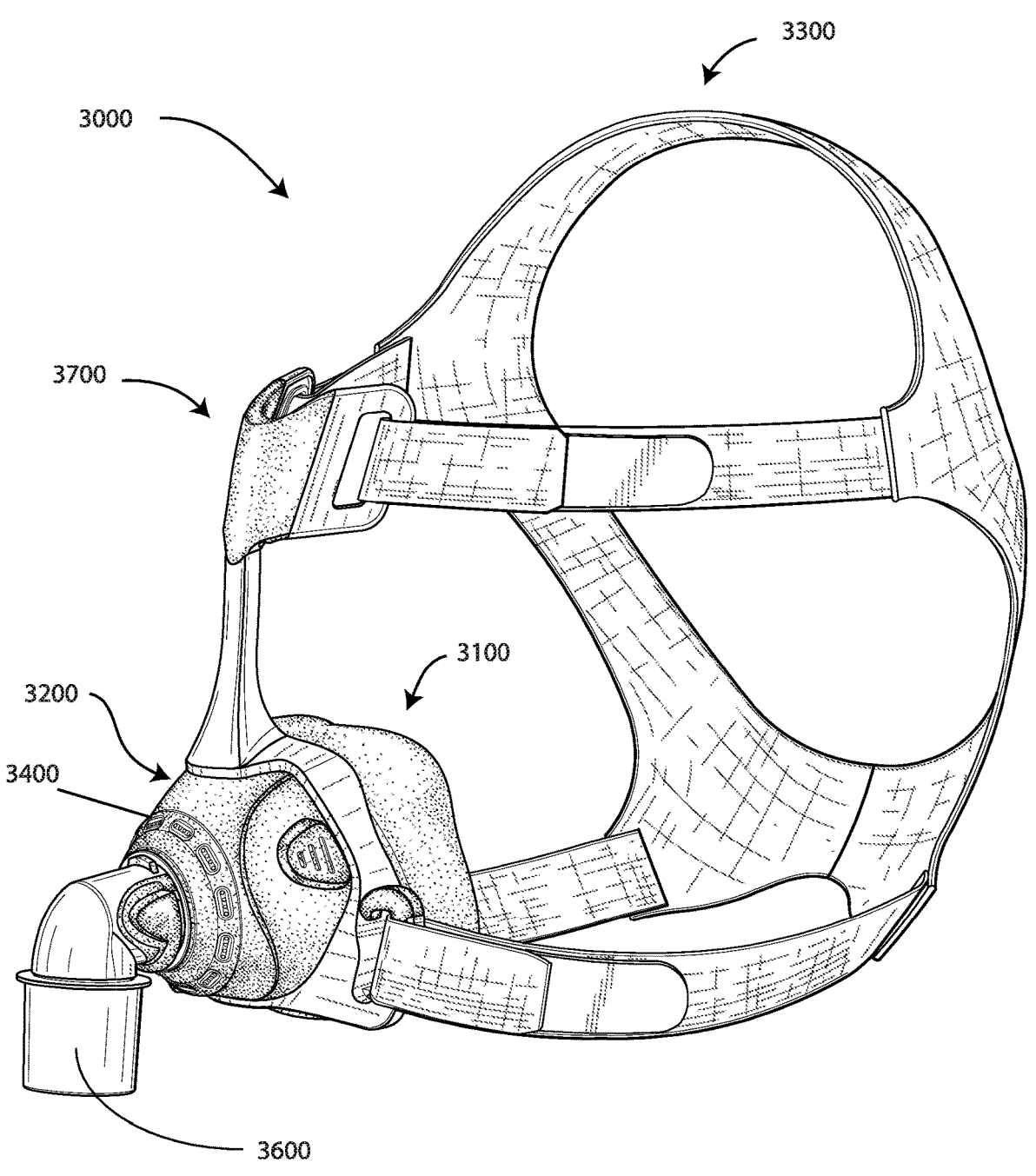

FIG. 3A shows a patient interface in the form of a nasal mask in accordance with one form of the present technology.

4.4 RPT Device

Figure 4A:
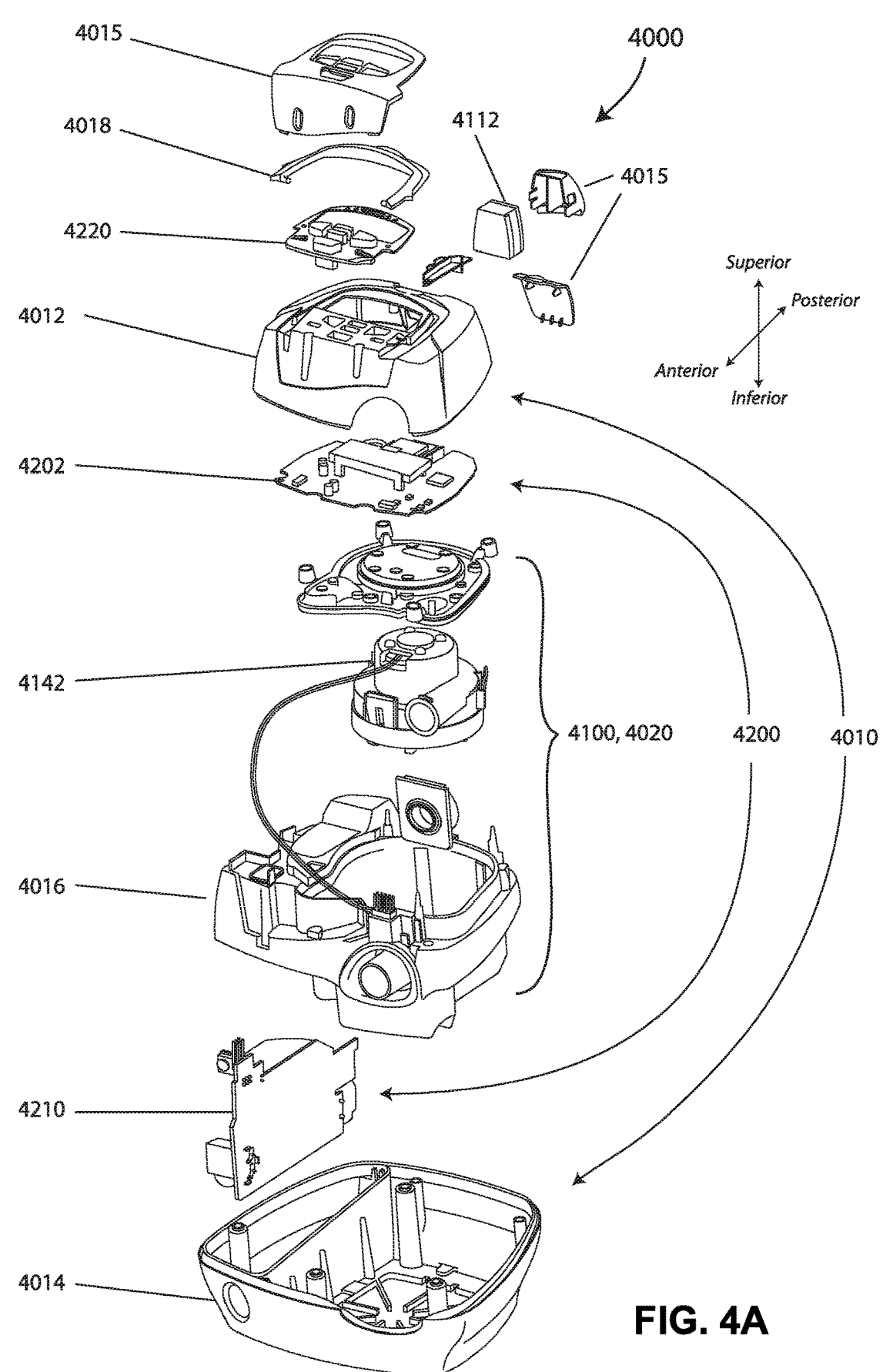

FIG. 4A shows an RPT device in accordance with one form of the present technology.

Figure 4B:
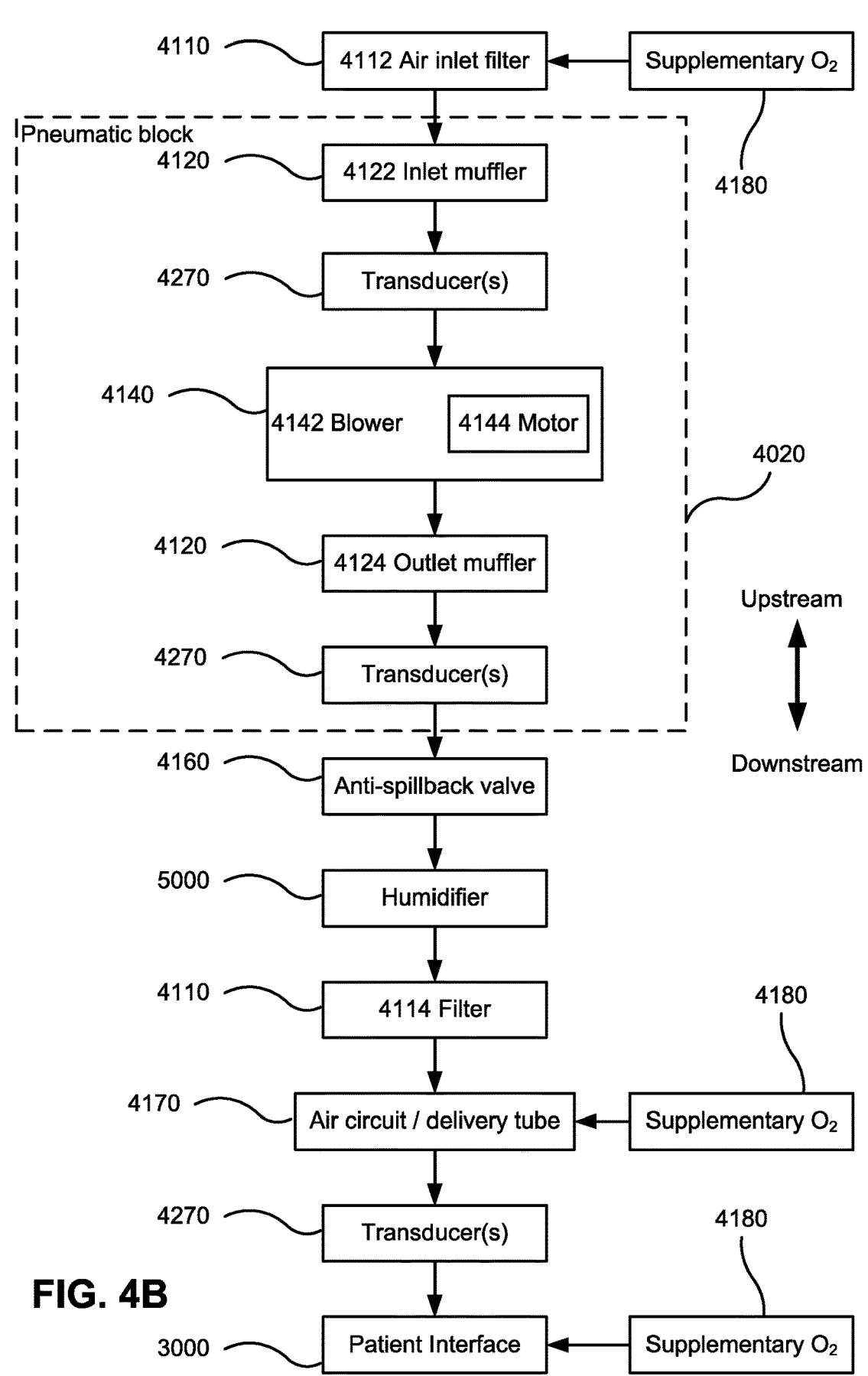

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
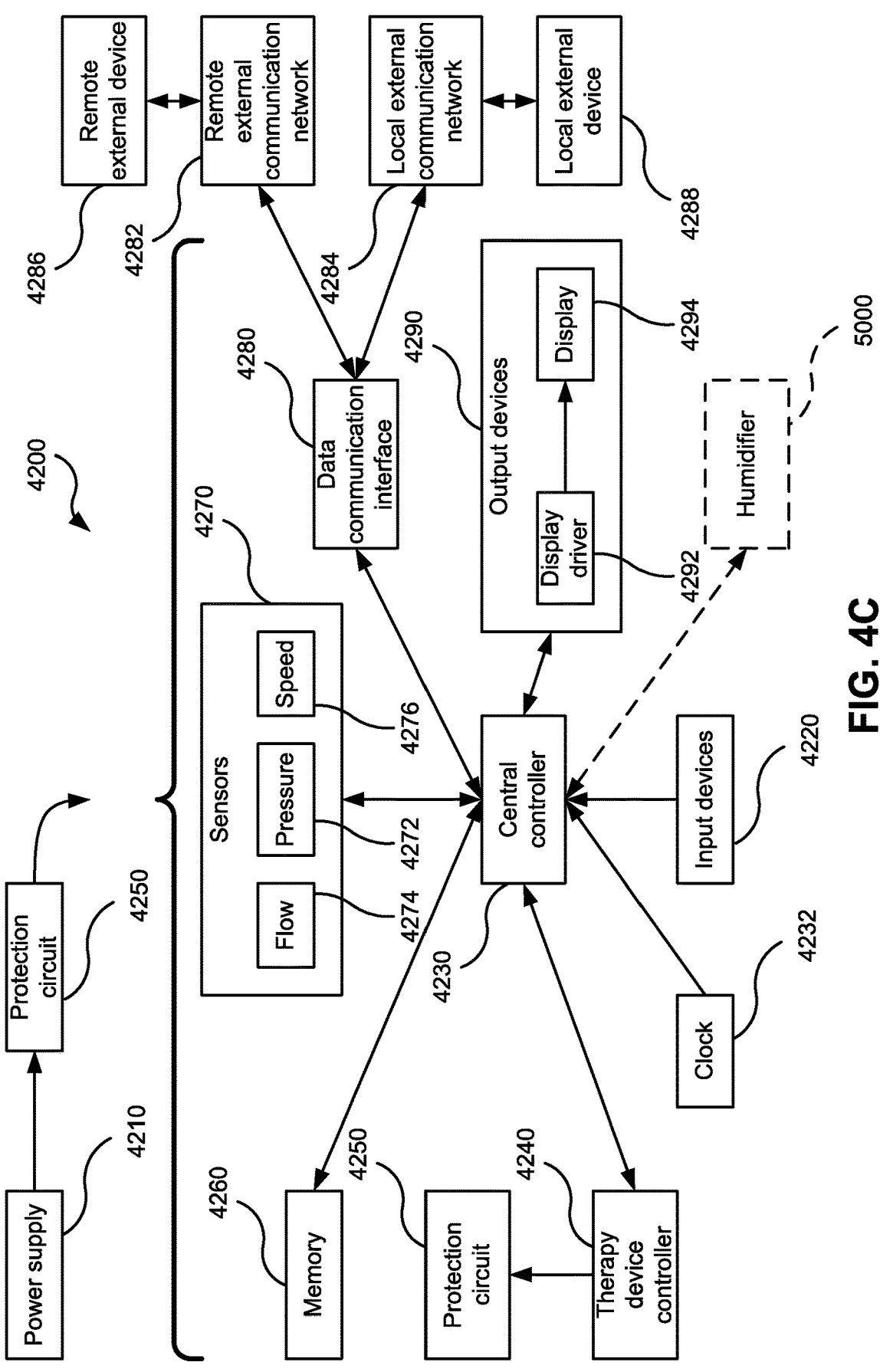

FIG. 4C is a schematic diagram of the electrical components of an RPT device in accordance with one form of the present technology.

Figure 4D:
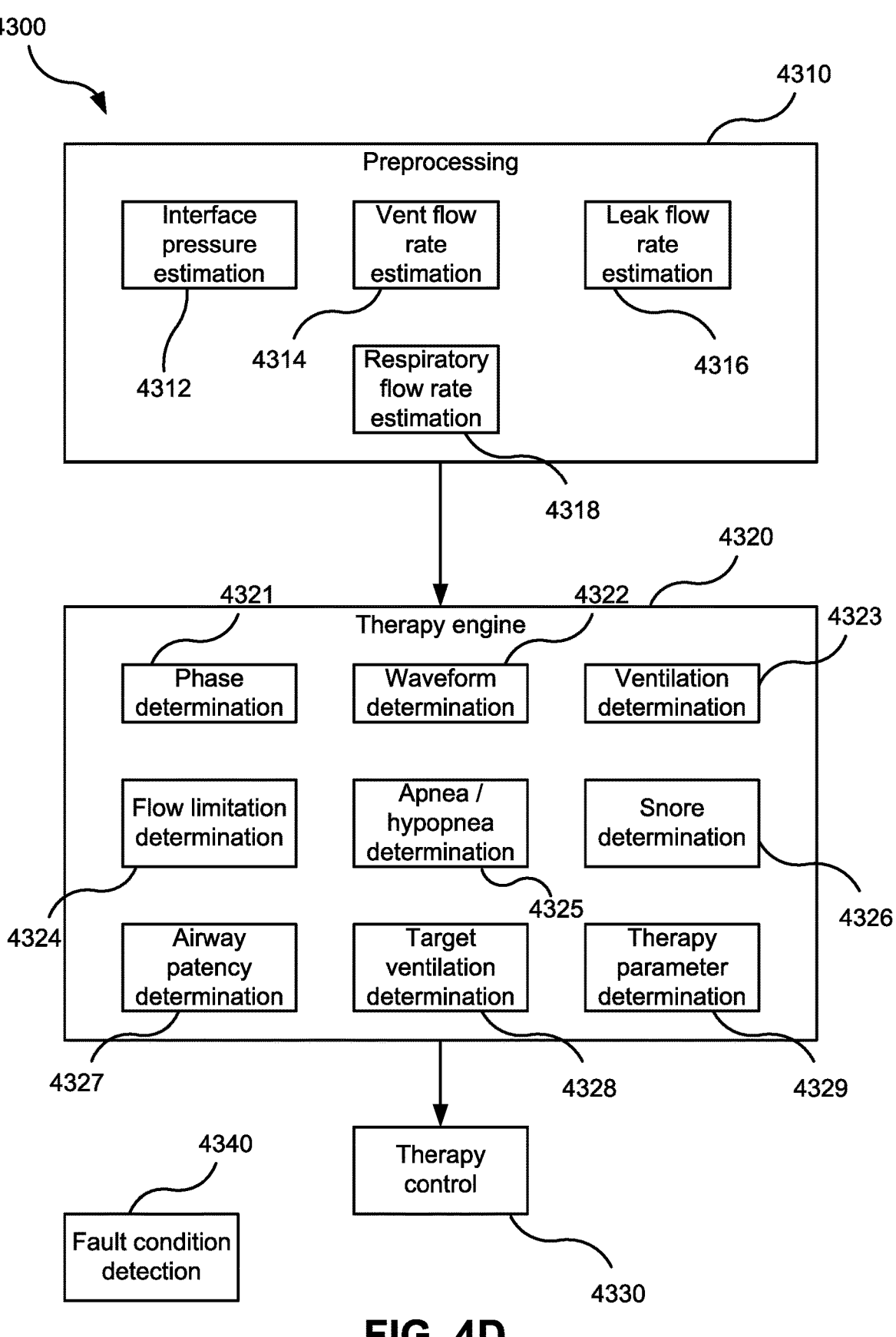

FIG. 4D is a schematic diagram of the algorithms implemented in an RPT device in accordance with one form of the present technology.

Figure 4E:
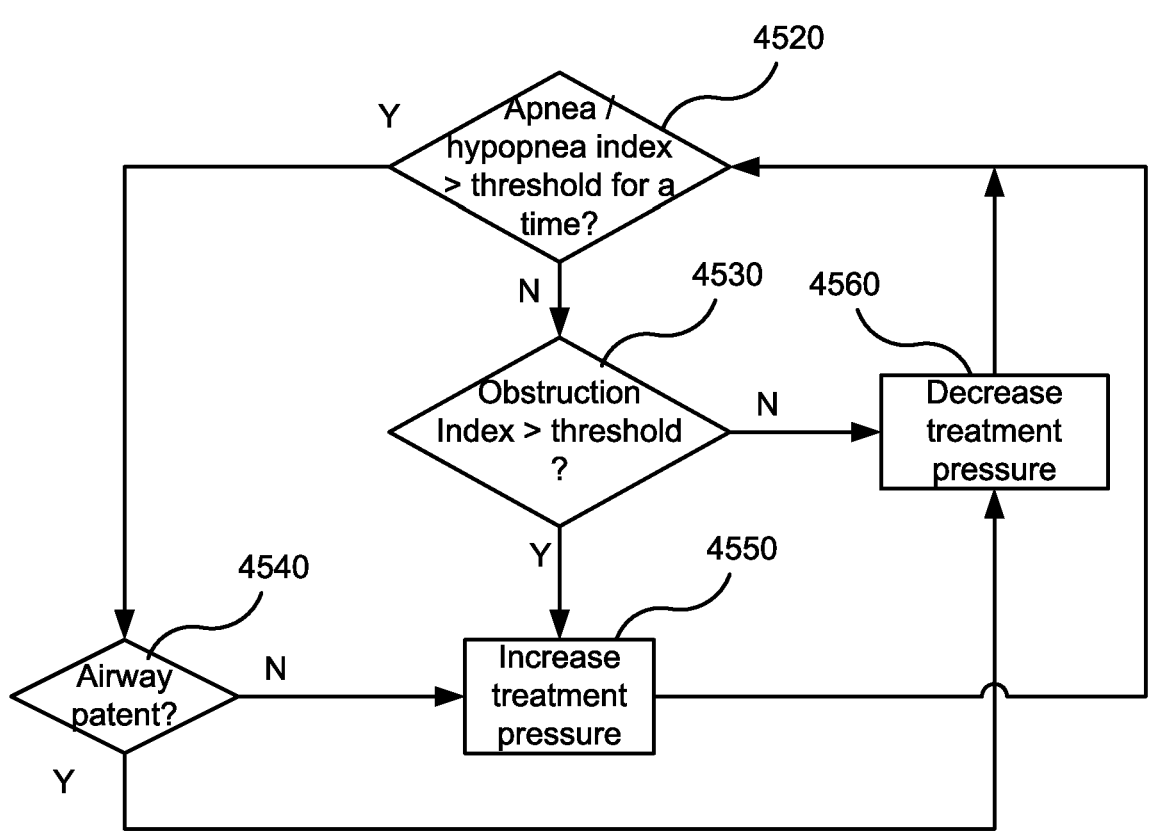

FIG. 4E is a flow chart illustrating a method carried out by the therapy engine module of FIG. 4D in accordance with one form of the present technology.

4.5 Humidifier

Figure 5A:
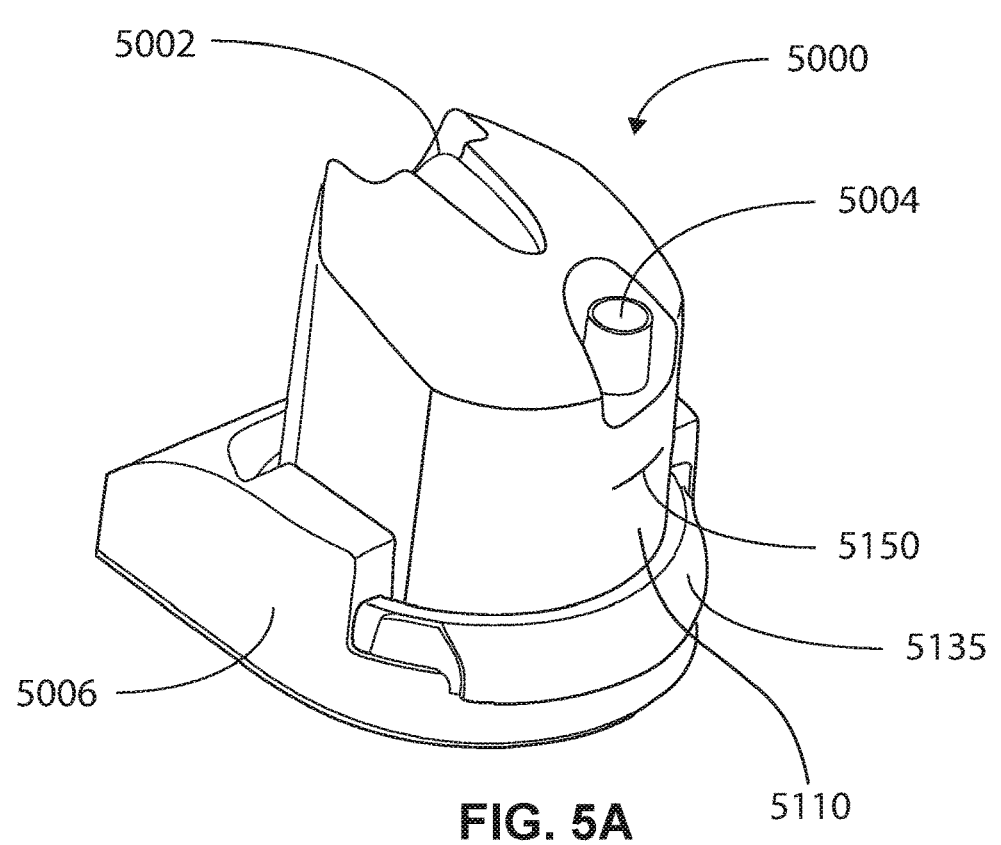

FIG. 5A shows an isometric view of a humidifier in accordance with one form of the present technology.

Figure 5B:
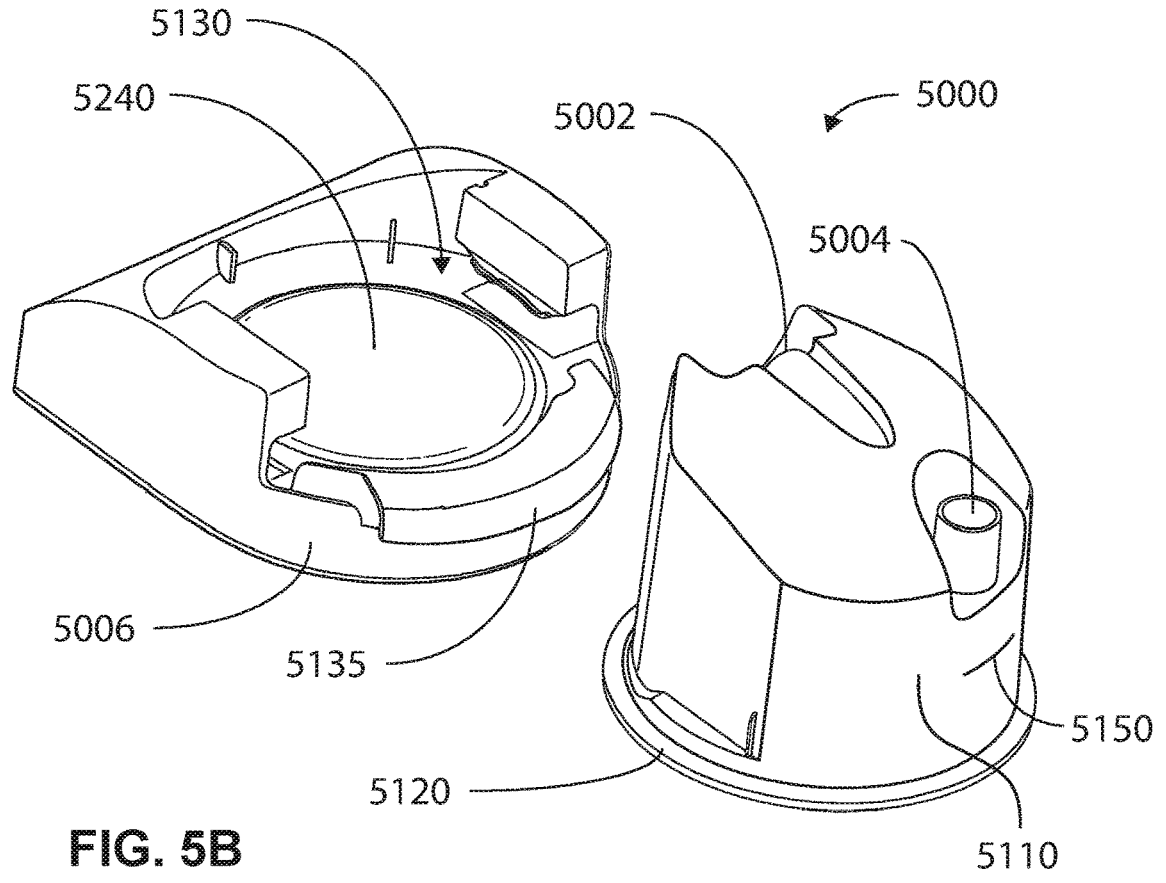

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
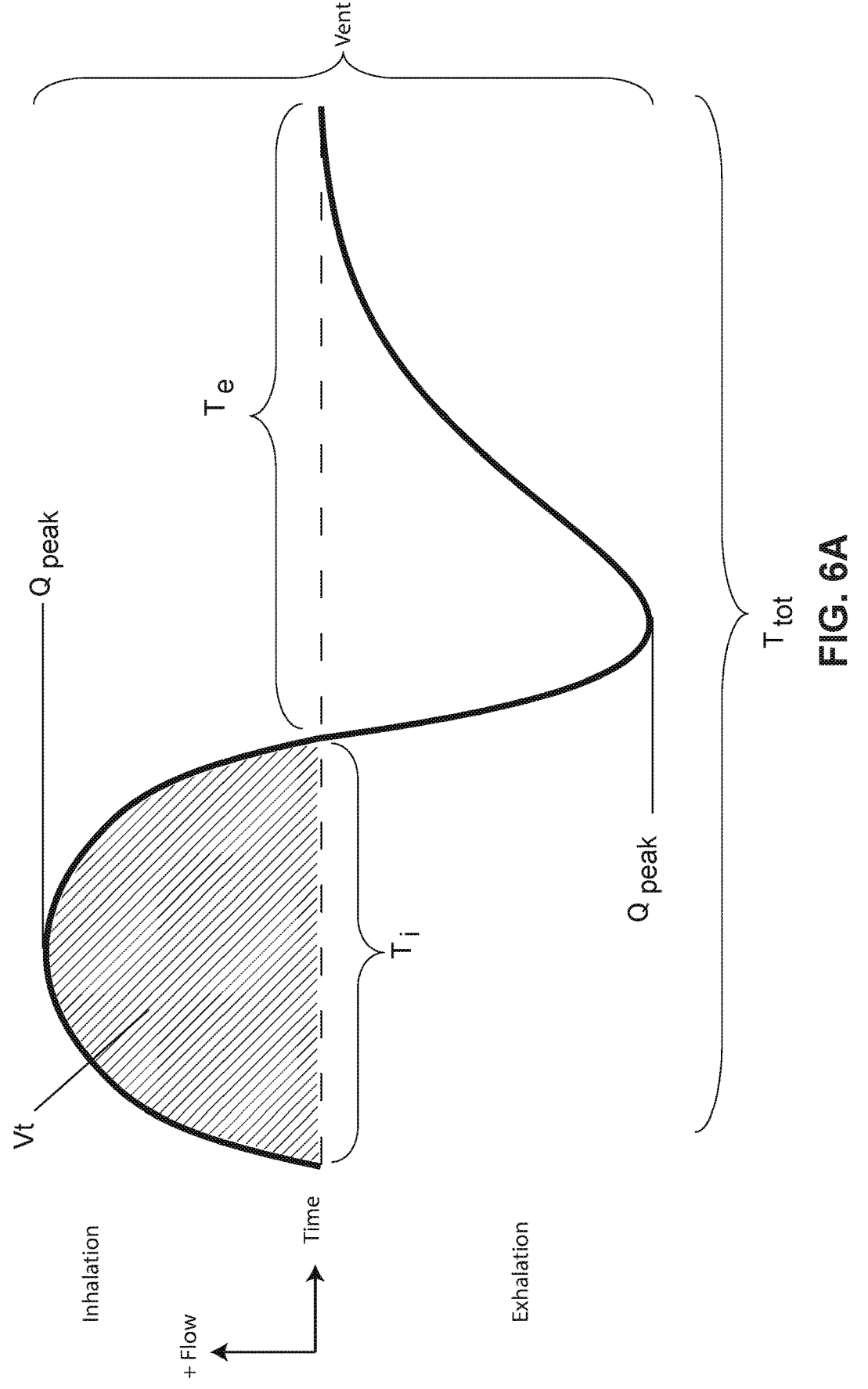

FIG. 6A shows a model typical breath waveform of a person while sleeping.

4.7 Eye Mask System

Figure 7:
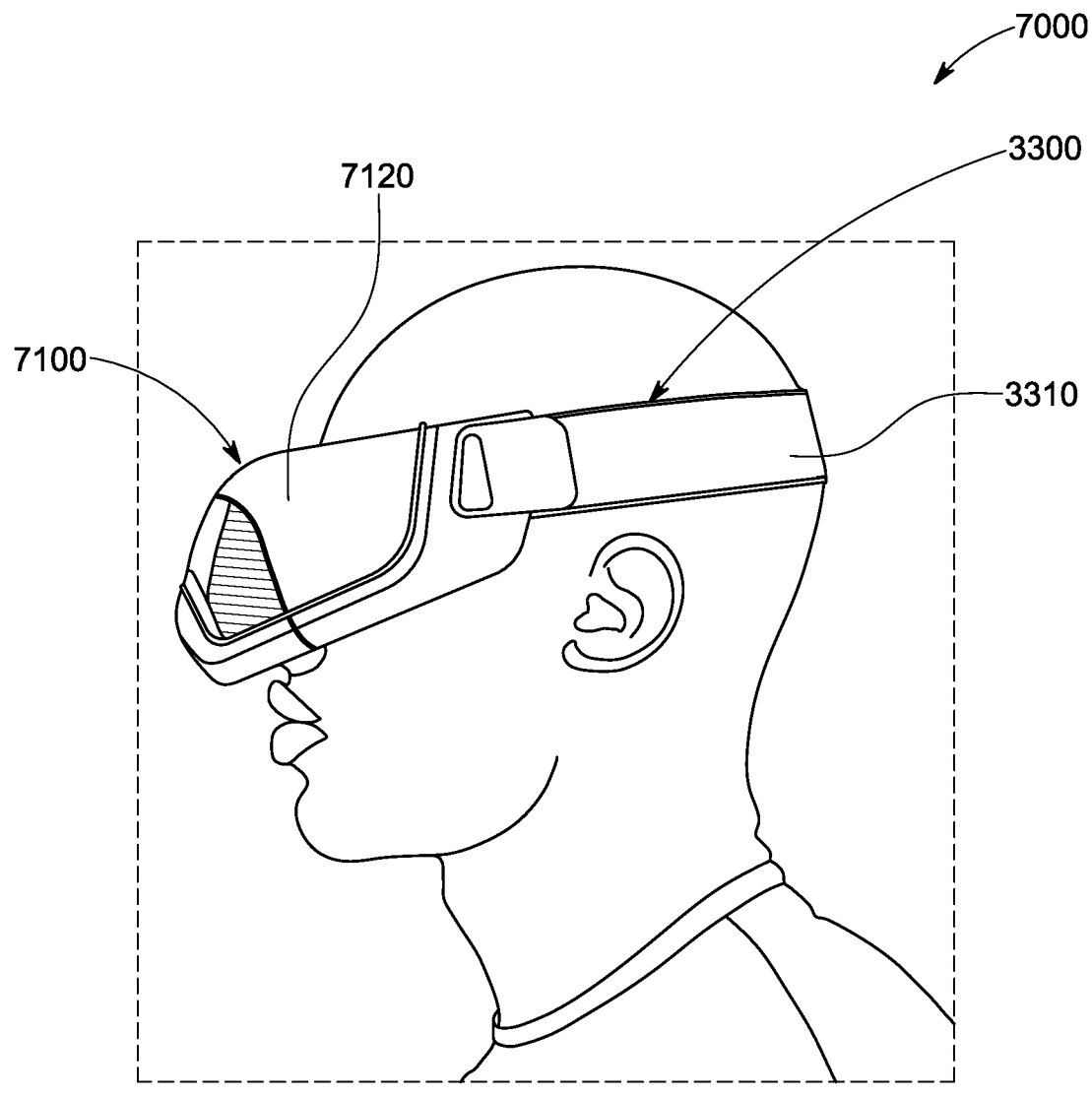

FIG. 7 shows a side view illustration of an eye mask system 7000 according to an example of the present technology worn by a patient.

Figure 8:
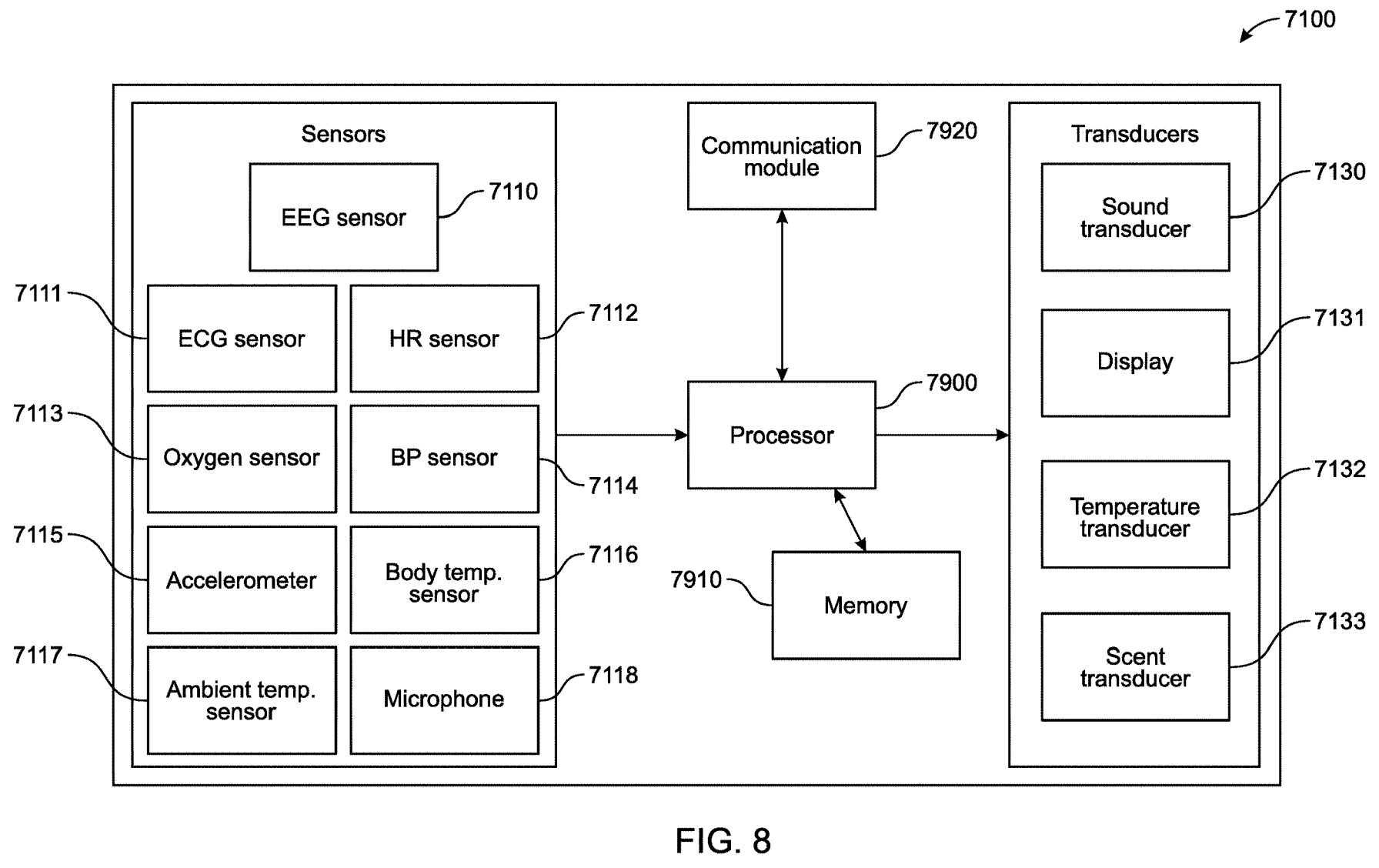

FIG. 8 shows a block diagram representing components of the eye mask 7100 of the eye mask system 7000 of FIG. 7.

Figure 9:
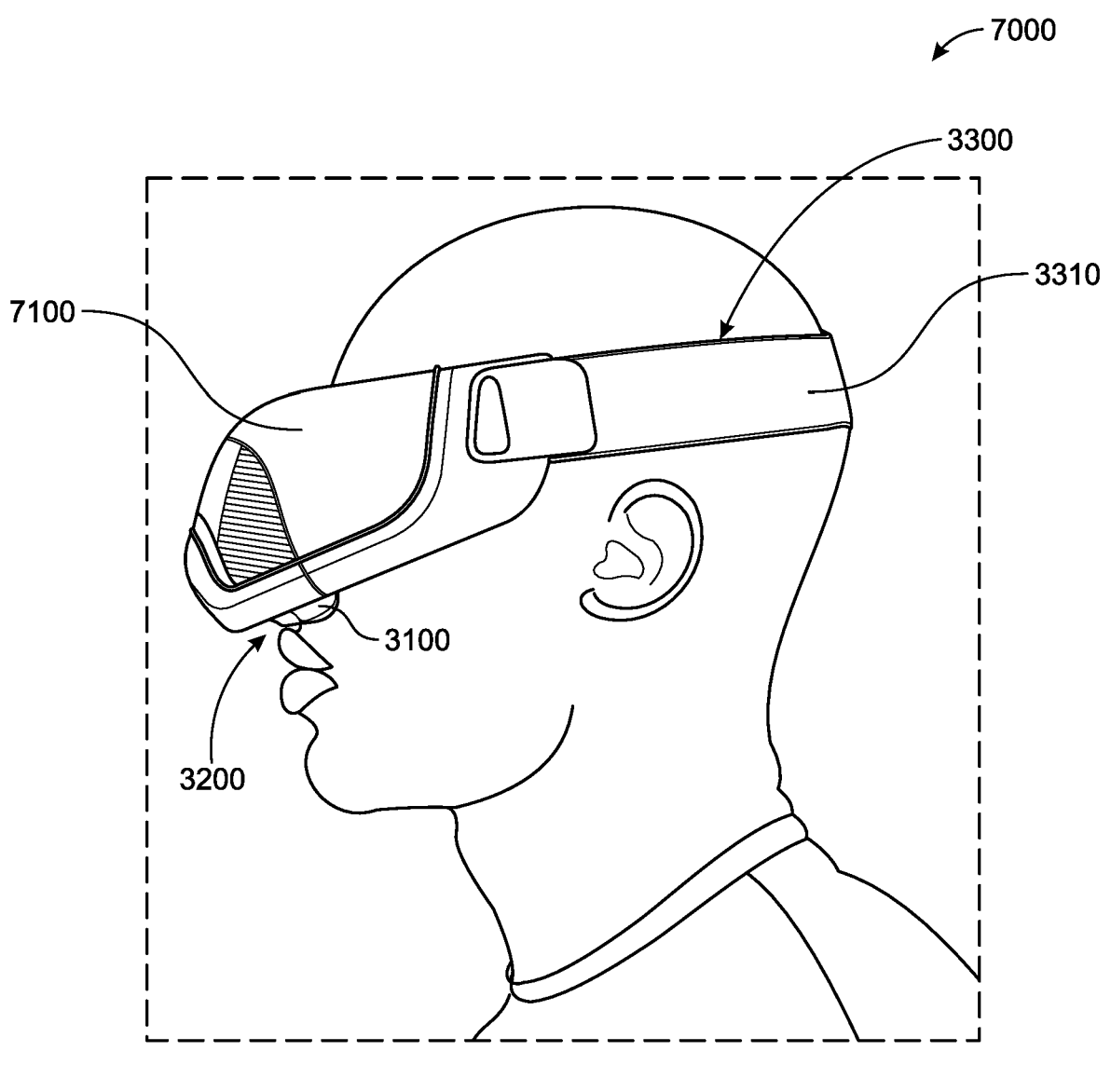

FIG. 9 shows a side view illustration of an eye mask system 7000 according to another example of the present technology worn by a patient and having a seal-forming structure 3100.

Figure 10:
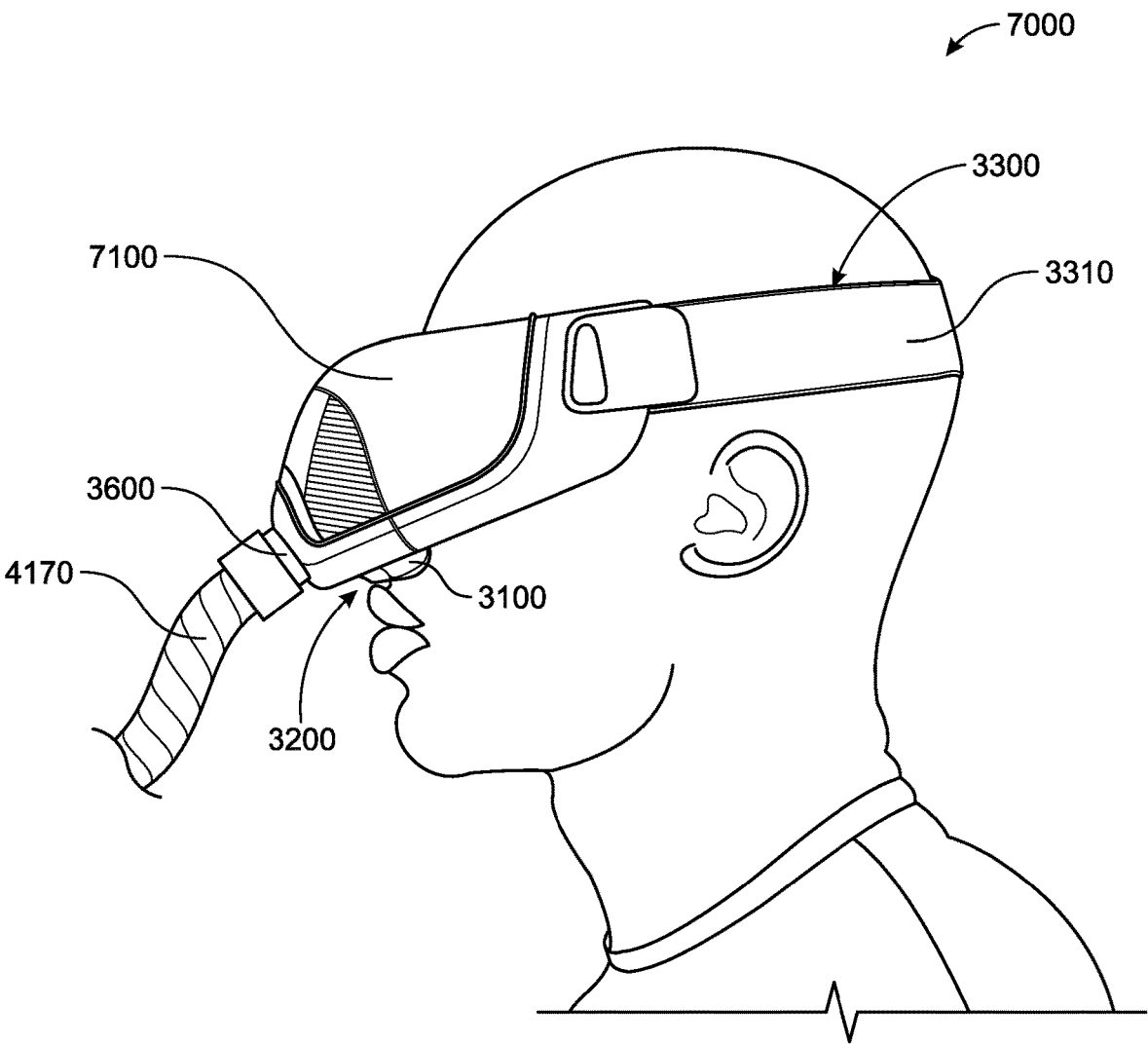

FIG. 10 shows a side view illustration of an eye mask system 7000 according to another example of the present technology worn by a patient and connected to an air circuit 4170.

Figure 11:
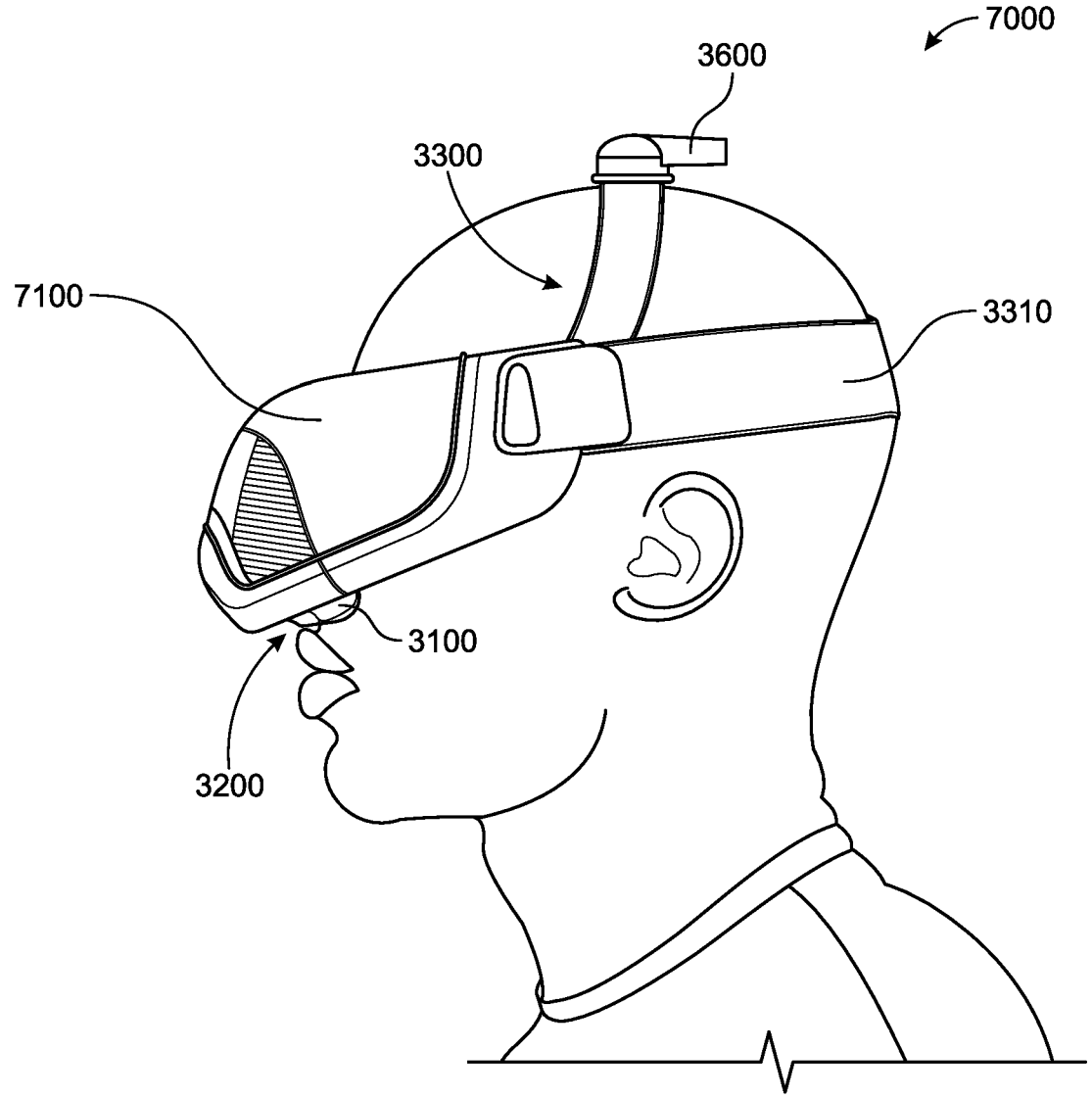

FIG. 11 shows a side view illustration of an eye mask system 7000 according to another example of the present technology worn by a patient and having a connection port 3600 located at a superior portion of the patient's head.

Figure 12:
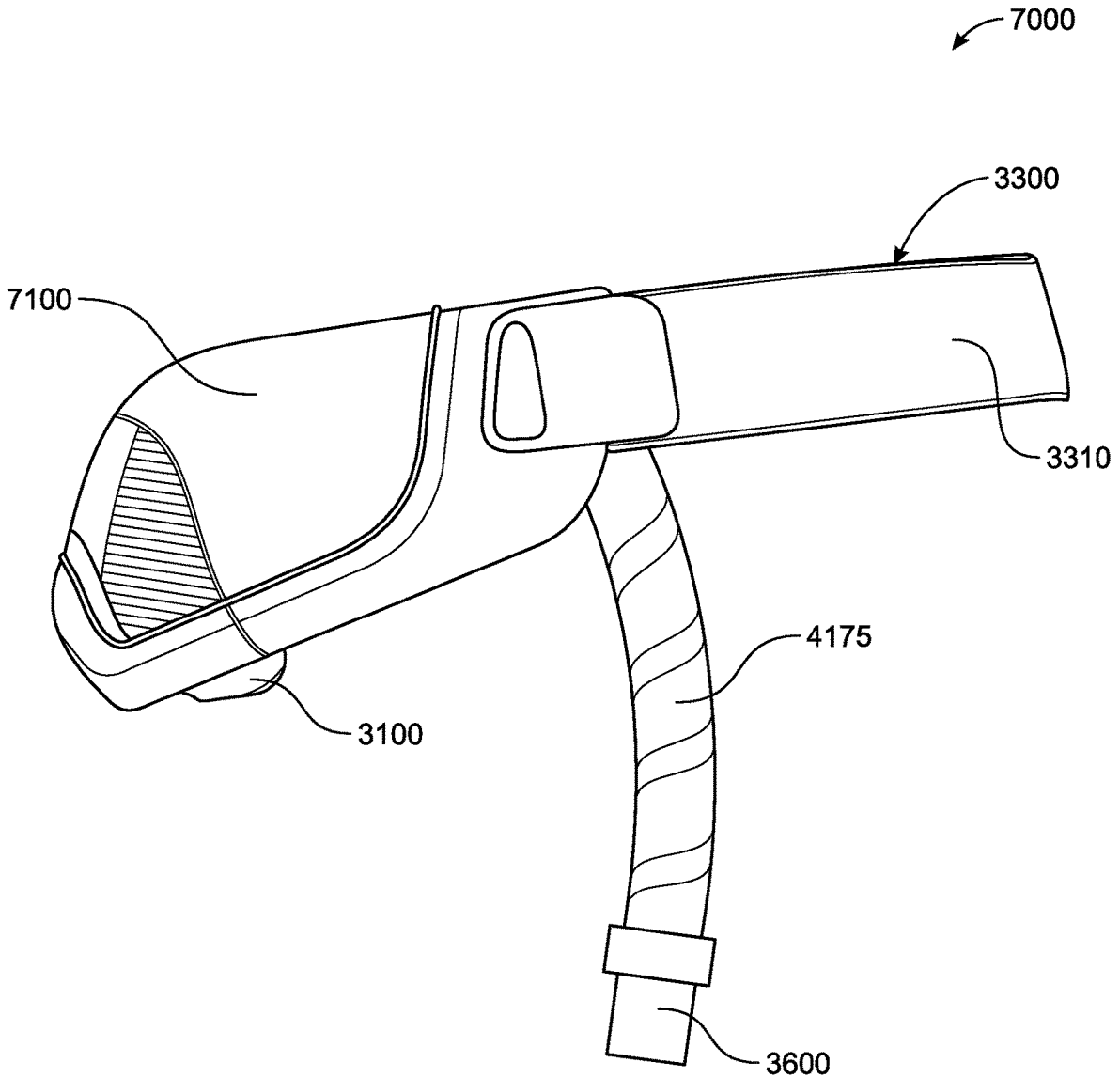

FIG. 12 shows a side view illustration of an eye mask system 7000 according to another example of the present technology and having a short tube 4175.

Figure 13:
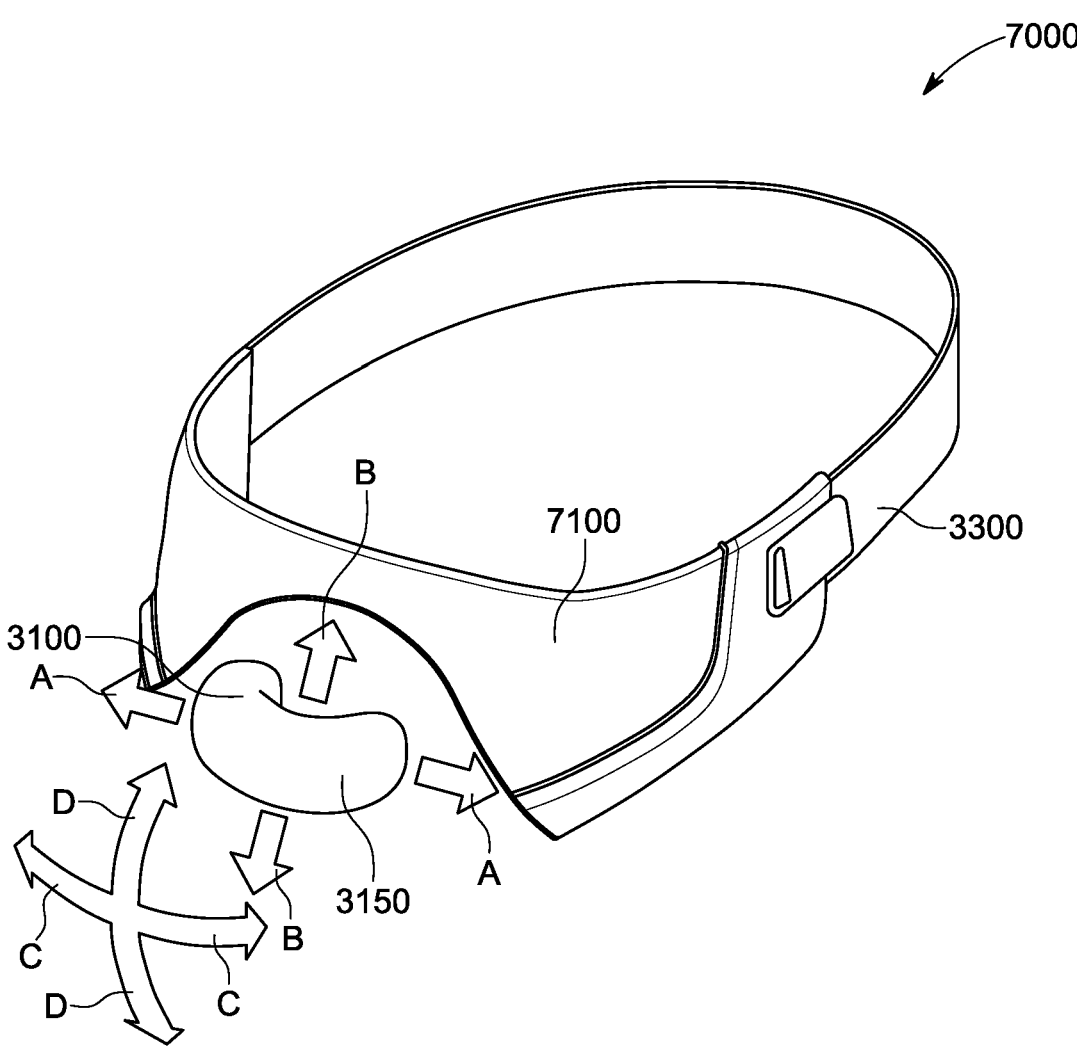

FIG. 13 shows a perspective cutaway view illustration of an eye mask system 7000 having a cushion module 3150.

Figure 14:
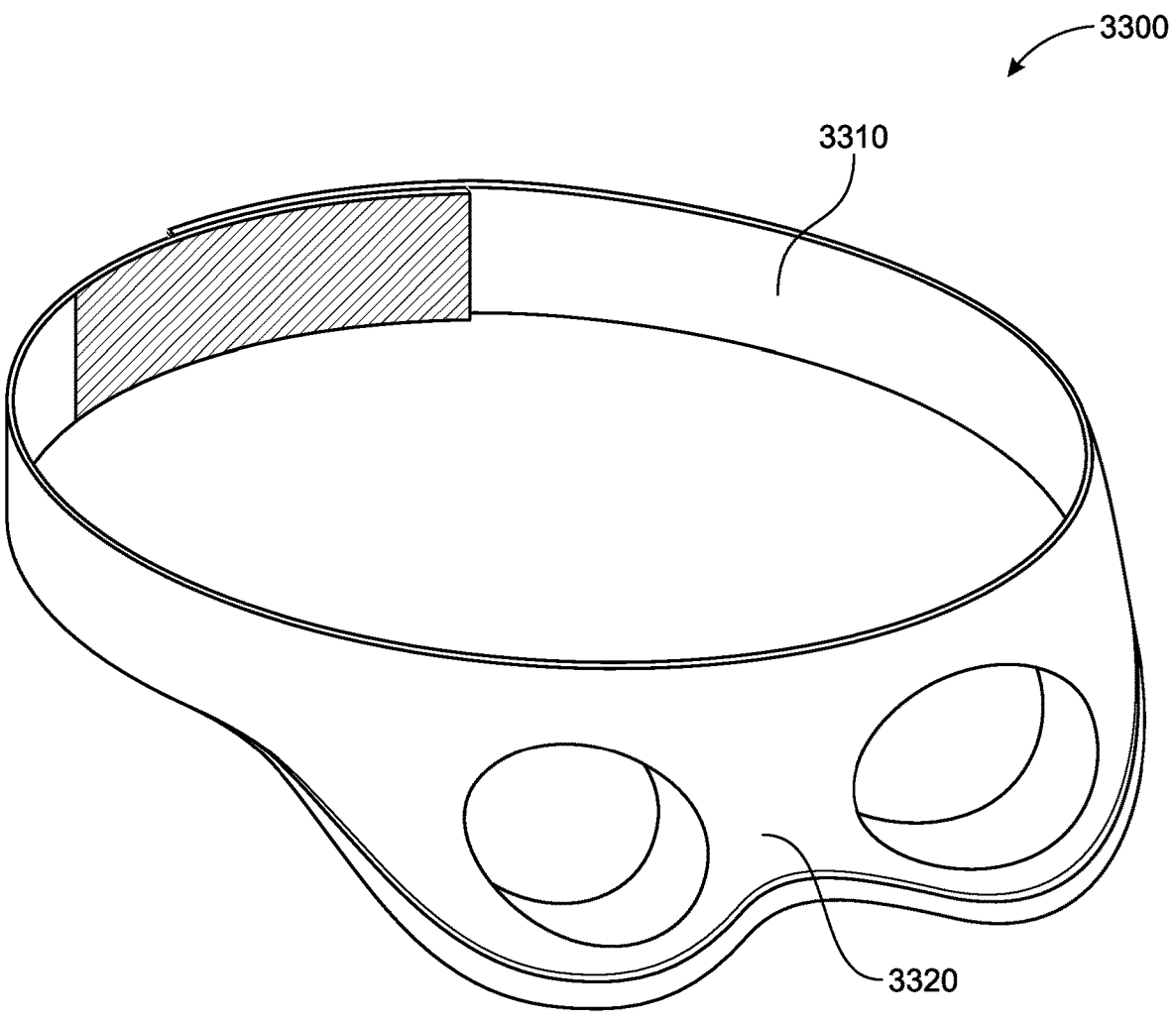

FIG. 14 shows a perspective view illustration of components of a positioning and stabilising structure 3300 for an eye mask system 7000.

Figure 15:
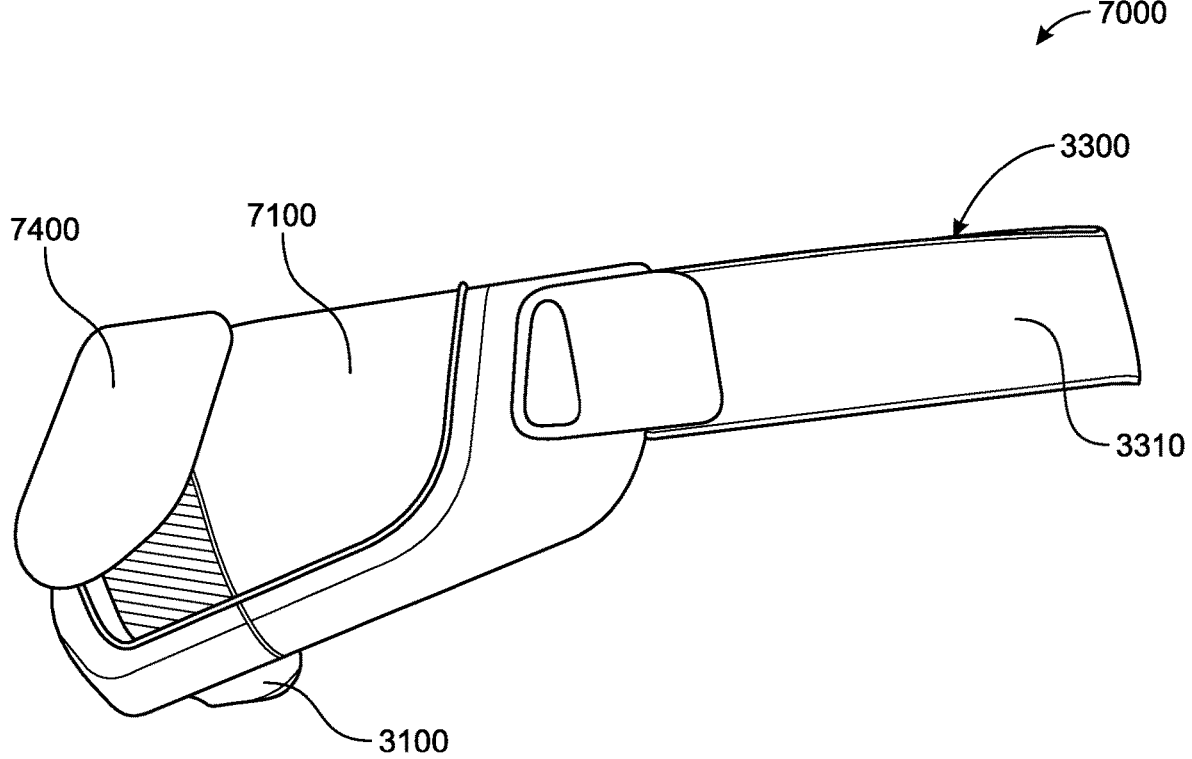

FIG. 15 shows a side view illustration of an eye mask system 7000 according to another example of the present technology worn by a patient and having a flow generator 7400.

Figure 16:
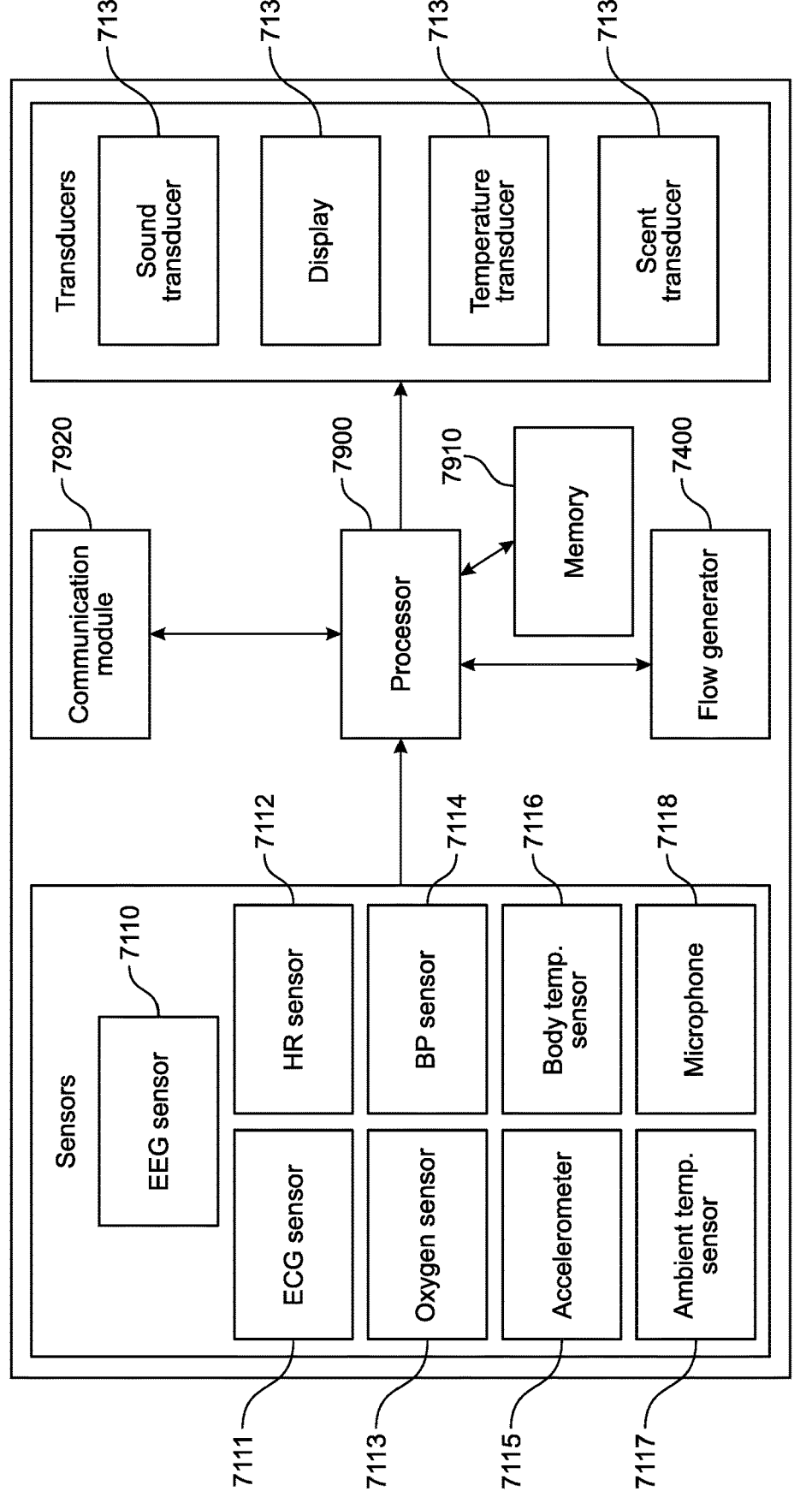

FIG. 16 shows a block diagram representing components of the eye mask system 7000 of FIG. 15.

Figure 17:
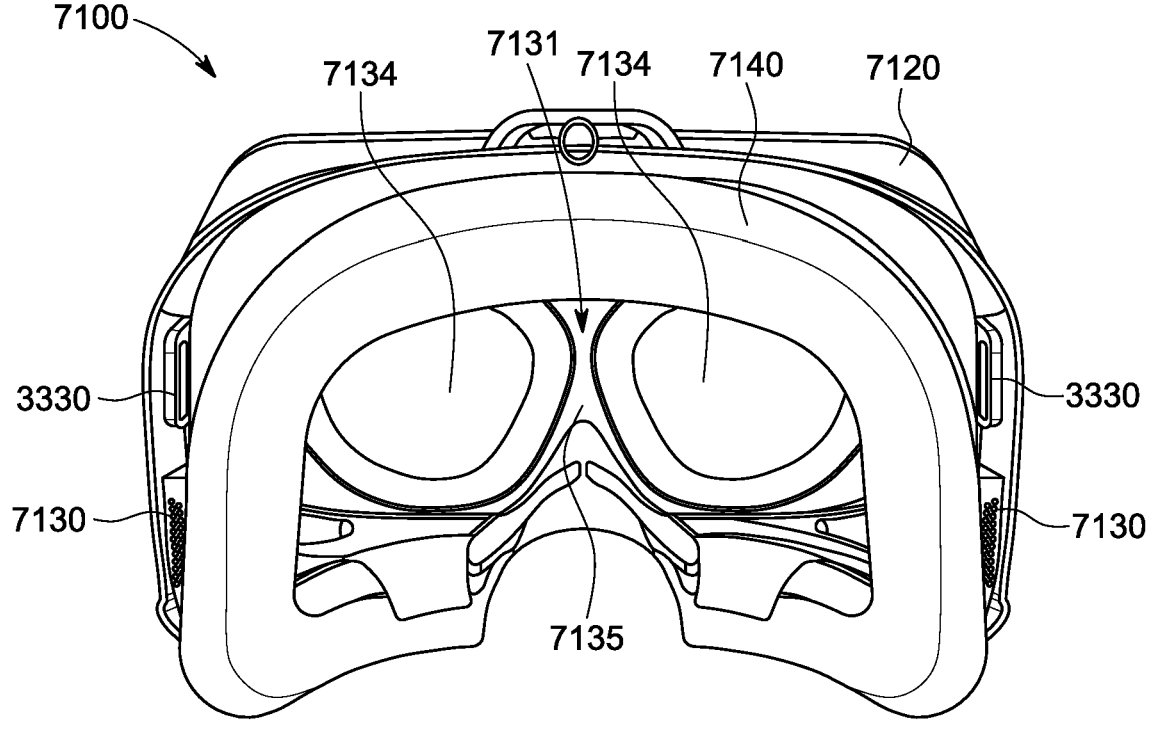

FIG. 17 shows a posterior view of an eye mask 7100 according to another example of the present technology.

Figure 18:
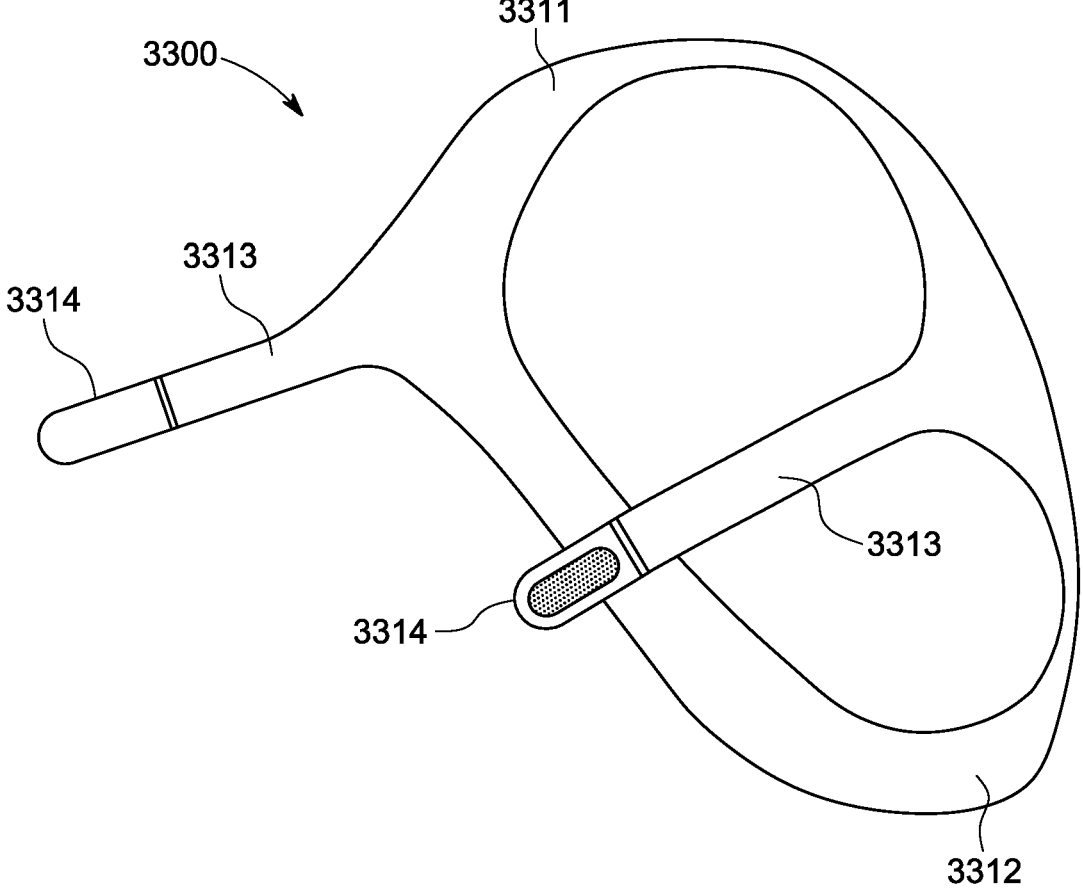

FIG. 18 shows a positioning and stabilising structure 3300 for an eye mask system 7000 according to another example of the present technology.

Figure 19:
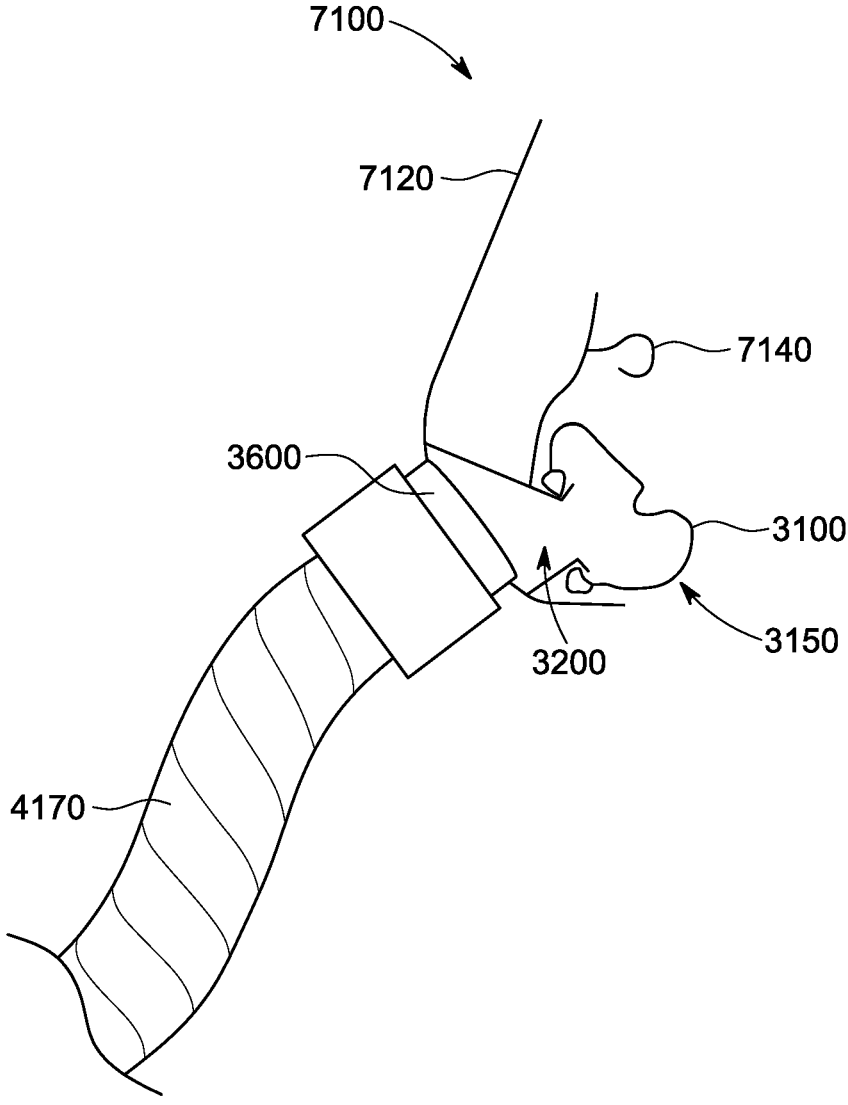

FIG. 19 shows a schematic view of an anterior portion of an eye mask 7100 according to another example of the present technology.

5 DETAILED DESCRIPTION OF EXAMPLES
OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH₂O with respect to ambient.

The patient interface 3000 in accordance with one form of the present technology is constructed and arranged to be able to provide a supply of air at a positive pressure of at least 10 cmH₂O with respect to ambient.

The patient interface 3000 in accordance with one form of the present technology is constructed and arranged to be able to provide a supply of air at a positive pressure of at least 20 cmH₂O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document. The RPT device 4000 may in some examples be incorporated into another device, such as an eye mask 7100 as will be described.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

In the example shown in FIG. 4A, the RPT device 4000 has an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272, flow rate sensors 4274 and/or motor speed sensors 4276.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

FIG. 15 shows an example of an eye mask system 7000 (to be described in more detail below) having a flow generator 7400. Unless context clearly requires otherwise, any of the features described in this specification in relation to the RPT device 4000 described with reference to FIGS. 4A-4C are to be understood to be applicable to the flow generator 7400. As will be described, the flow generator 7400 in some examples is configured to provide a pressurised flow of air for respiratory therapy and in other examples is configured to provide a flow of air for purposes other than therapy.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The blower 4142 may be contained in a blower housing 4100. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866, 944; 8,638,014; 8,636,479; and PCT Patent Application Publication No. WO 2013/020167.

The flow generator 7400 described below may comprise a pressure generator 4140 as described herein although, as will be described, may not necessarily be configured for providing respiratory pressure therapy. Where the pressure generator 4140 or any component or function of the RPT device 4000 is described with reference to therapy, the disclosure is to be understood as relevant to the flow generator 7400, whether the flow of air is for therapeutic purposes (e.g. respiratory pressure therapy for treatment of sleep disordered breathing) or non-therapeutic purposes (e.g. heating, cooling, sensory effects and the like).

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144. In examples where there is no humidifier in the system, for example in the eye mask system 7000 described with reference to FIGS. 15-16, the flow generator 7400 may not comprise an anti-spill back valve.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions express-ing the one or more methodologies described herein, such as the one or more algorithms 4300.

5.4.2.5 Data Communication Systems

In one form of the present technology, a data communi-cation interface 4280 is provided, and is connected to the central controller 4230. Data communication interface 4280 may be connectable to a remote external communication network 4282 and/or a local external communication net-work 4284. The remote external communication network 4282 may be connectable to a remote external device 4286. The local external communication network 4284 may be connectable to a local external device 4288.

In one form, data communication interface 4280 is part of the central controller 4230. In another form, data commu-nication interface 4280 is separate from the central control-ler 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal com-puter, mobile phone, tablet or remote control.

5.4.2.6 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.6.1 Display Driver

A display driver 4292 receives as an input the characters, symbols, or images intended for display on the display 4294, and converts them to commands that cause the display 4294 to display those characters, symbols, or images.

5.4.2.6.2 Display

A display 4294 is configured to visually display charac-ters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.2.6.3 Clock

The RPT device 4000 may include a clock 4232 that is connected to the central controller 4230.

5.4.3 RPT Device Algorithms

As mentioned above, in some forms of the present tech-nology, the central controller 4230 may be configured to implement one or more algorithms 4300 expressed as com-puter programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermedi-ate algorithm outputs necessary for the portion of the algorithms 4300 to be executed at the external device may be communicated to the external device via the local exter-nal communication network 4284 or the remote external communication network 4282. In such forms, the portion of the algorithms 4300 to be executed at the external device may be expressed as computer programs stored in a non-transitory computer readable storage medium accessible to the controller of the external device. Such programs con-figure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.4.3.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 estimates the pressure drop ΔP through the air circuit 4170. The dependence of the pressure drop ΔP on the total flow rate Qt may be modelled for the particular air circuit 4170 by a pressure drop characteristic ΔP(Q). The interface pressure estimation algorithm, 4312 then provides as an output an estimated pressure, Pm, in the patient interface 3000. The pressure, Pm, in the patient interface 3000 may be estimated as the device pressure Pd minus the air circuit pressure drop ΔP.

5.4.3.1.2 Vent Flow Rate Estimation

In one form of the present technology, a vent flow rate estimation algorithm 4314 receives as an input an estimated pressure, Pm, in the patient interface 3000 from the interface pressure estimation algorithm 4312 and estimates a vent flow rate of air, Qv, from a vent 3400 in a patient interface 3000. The dependence of the vent flow rate Qv on the interface pressure Pm for the particular vent 3400 in use may be modelled by a vent characteristic Qv(Pm).

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination algorithm 4326, airway patency determination algorithm 4327, target ventilation determination algorithm 4328, and therapy parameter determination algorithm 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.

8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase $\Phi$ is first discretely estimated from the respiratory flow rate Qr as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template $\Pi(\Phi)$ is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template $\Pi(\Phi)$ from a library of waveform templates, dependent on a setting of the RPT device. Each waveform template $\Pi(\Phi)$ in the library may be provided as a lookup table of values H against phase values $\Phi$. In other forms, the waveform determination algorithm 4322 computes a waveform template $\Pi(\Phi)$ "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation ($\Phi$=0 revolutions) or exhalation ($\Phi$=0.5 revolutions), the waveform determination algorithm 4322 computes a waveform template $\Pi$ "on the fly" as a function of both discrete phase $\Phi$ and time t measured since the most recent trigger instant. In one such form, the waveform determination algorithm 4322 computes the waveform template $\Pi(\Phi, t)$ in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template $\Pi(\Phi, t)$. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)

Transducer fault detection

Failure to detect the presence of a component

Operating parameters outside recommended ranges (e.g. pressure, flow rate, temperature, $PaO_2$)

Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm

Sending a message to an external device

Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a central controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components 5.6.2.1 Water Reservoir

According to one arrangement, the humidifier 5000 may comprise a humidifier reservoir 5110 configured to hold, or retain, a volume of liquid (e.g. water) to be evaporated for humidification of the flow of air. The humidifier reservoir 5110 may be configured to hold a predetermined maximum volume of water in order to provide adequate humidification for at least the duration of a respiratory therapy session, such as one evening of sleep. Typically, the humidifier reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the humidifier reservoir 5110 is configured to add humidity to a flow of air from the RPT device 4000 as the flow of air travels therethrough. In one form, the humidifier reservoir 5110 may be configured to encourage the flow of air to travel in a tortuous path through the humidifier reservoir 5110 while in contact with the volume of water therein.

According to one form, the humidifier reservoir 5110 may be removable from the humidifier 5000, for example in a lateral direction as shown in FIG. 5A and FIG. 5B.

The humidifier reservoir 5110 may also be configured to discourage egress of liquid therefrom, such as when the humidifier reservoir 5110 is displaced and/or rotated from its normal, working orientation, such as through any apertures and/or in between its sub-components. As the flow of air to be humidified by the humidifier 5000 is typically pressurised, the humidifier reservoir 5110 may also be configured to prevent losses in pneumatic pressure through leak and/or flow impedance.

5.6.2.2 Conductive Portion

According to one arrangement, the humidifier reservoir 5110 comprises a conductive portion 5120 configured to allow efficient transfer of heat from the heating element 5240 to the volume of liquid in the humidifier reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the humidifier reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system.

5.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ).

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment JP, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$–Pmin, so that the decrease in $P_0$ to the minimum treatment pressure Pmin in the absence of any detected events is exponential. In one implementation, the constant of proportionality is set such that the time constant r of the exponential decrease of $P_0$ is 60 minutes, and the minimum treatment pressure Pmin is 4 $cmH_2O$. In other implementations, the time constant r could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 $cmH_2O$. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G \int (\text{Vent} - Vtgt)dt \qquad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure P$_0$. As with the base pressure P$_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure P$_0$ in constant CPAP therapy.

Alternatively, the therapy parameter determination algorithm 4329 may repeatedly compute the base pressure P$_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.9 Eye Mask System

Some forms of the present technology comprise an eye mask system 7000. An eye mask system 7000 according to examples of the present technology may also be identified as a sleep mask or a headset. Depending on particular configurations it may also be identified as a VR headset, AR headset or patient interface. Eye mask systems 7000 in accordance with aspects of the present technology may comprise some or all of the following functional aspects: an eye mask 7100, a seal-forming structure 3100, a plenum chamber 3200 and a positioning and stabilising structure 3300, a connection port 3600, and/or a flow generator 7400. In some forms a functional aspect may be provided by one or more physical components. In some forms, one physical component may provide one or more functional aspects.

The eye mask system 7000 may be used by a user. A user may be a person with an ailment/disorder (e.g. patient) or a person without an ailment/disorder.

FIG. 7 shows an eye mask system 7000 worn by a user. As illustrated, the eye mask system 7000 comprises an eye mask 7100 and a positioning and stabilising structure 3300. The eye mask 7100 may be held in an in-use position by the positioning and stabilising structure 3300.

In some forms, the eye mask system 7000 may be considered a "smart" eye mask. That is, the eye mask system 7000 may comprise features considered to be "smart" features, such as the ability to interact with the user, and may operate partly or fully autonomously to provide certain functions. The eye mask system 7000 may comprise one or more transducers configured to interface with the user and/or the ambient environment. A transducer is a device that converts energy from one form to another. In the present specification the term "transducer" is used to mean a device that converts energy between a signal, usually in the form of an electrical signal, and another form of energy (either converting from or to the signal), unless the context clearly indicates otherwise. The transducer interfaces with the user and/or the ambient environment through such energy conversions. The one or more transducers may interface by sensing or receiving information about the user and/or the ambient environment, for example. Additionally, or alternatively, the one or more transducers may interact by providing input to the user and/or the ambient environment, for example one or more physical stimuli.

In some examples the eye mask system 7000 may be used to facilitate sleep by helping the user fall asleep. In some forms the eye mask system 7000 may promote improved sleep or higher quality sleep for the user through the use of transducers, for example sensors and output transducers. In some forms the eye mask system 7000 is configured to provide sensory feedback to the user. In other forms the eye mask system 7000 may monitor the user's sleep and provide feedback to the user in the form of sleep data, a summary of the user's sleep data over a period of time, a summary of the user's sleep behaviour over a period of time, and/or suggestions on how to improve sleep. In some forms the eye mask system 7000 may diagnose sleep apnea and/or assist in its treatment, for example with the components and methods described with reference to FIGS. 4D and 4E.

In some forms the eye mask system 7000 may be used while the user is awake. The eye mask system 7000 may have features or functions which are used while the user is awake and while the user is not trying to sleep. The eye mask system 7000 may be configured to promote relaxation. The eye mask system 7000 may be configured for entertainment, productivity, education, communication, training or the like. In some forms the eye mask system 7000 may be configured to provide assistance to a user during setup and/or fitting of the eye mask system 7000 for respiratory pressure therapy.

FIG. 8 shows a block diagram of the eye mask system 7000 shown in FIG. 7. As shown, the eye mask system 7000 includes a number of sensors and output transducers, which will be described below. Additionally, the eye mask system 7000 comprises a processor 7900, memory 7910 and a communication module 7920. In various examples of the technology, the processor 7900 may perform any of the functions described above in relation to the central controller 4230 of the RPT device 4000. Likewise, in various examples, the memory 7910 and the communication module 7920 may respectively operate in any one of the ways that the memory 4260 and data communication interface 4280 may operate.

Actions described herein as being steps performed by the eye mask system 7000 (such as actions, determinations, identifications, comparisons, optimisations, operations, among others) are to be understood to be steps performed in full or part by a processor 7900 of the eye mask system 7000. The processor 7900 may interface with memory 7910, for example to store and access data, execute stored instructions and the like. The processor 7900 and memory 7910 may also interface with the communication module 7920 to send and receive data to other devices, such as a remote server, a respiratory pressure therapy device 4000, a wristband worn by the patient, sensors, output transducers, among other options. While in the FIG. 8 block diagram the sensors are all illustrated as being in direct communication with the processor 7900, some or all of them may interface with the processor 7900 via the communication module 7920.

The processor 7900, memory 7910 and communication module 7920 may each comprise multiple components. For example, the processor 7900 may comprise multiple processors together providing the processing functions of the eye mask system 7000. Likewise, the memory 7910 may comprise multiple forms of memory (e.g. volatile and non-volatile memory) and the communication module 7920 may comprise multiple communication components (e.g. WiFi, Bluetooth, NFC and the like).

In some forms the processor 7900 may be located remote from the eye mask 7100 and may communicate with the eye mask 7100 via communication module 7920. In other forms, the processor 7900 comprises one or more processors 7900 incorporated into the eye mask 7100 and one or more other processors 7900 located remote from the eye mask 7100 and configured to communicate with the eye mask 7100 via communication module 7920.

In some examples, the eye mask system 7000 is powered in use by a battery, for example housed in the eye mask 7100 or housed in a separate housing supported by the positioning and stabilising structure 3300. In other examples, the eye mask system 7000 may comprise a power lead configured to plug into a separate power source, such as an auxiliary battery or a wall socket.

In certain forms of the technology, eye mask system 7000 comprises, or is configured to communicate with, one or more external devices, for example remote external device 4286 and/or local external device 4288 as described above. External devices may be in the vicinity of the user (e.g. the user's phone or an RPT device 4000 accessible via Bluetooth, the internet or the like) or may be remote from the user (e.g. computing devices, a server or the like accessible over the internet). Communication with external devices may occur through communication module 7920. The eye mask system 7000 may be configured to receive inputs from, or send outputs to, or otherwise communicate with, such external devices in order to achieve any one or more of the functions described herein. For example, external devices may be used to enable a user to interact with, for example configure, the eye mask system 7000. External devices may also be used to output data, reports, analysis results or any other information product of the eye mask system 7000.

It is to be understood that where the eye mask system 7000 or components thereof are described as being able to take an action or provide a function, it is to be understood that the eye mask system 7000 or components thereof, as the case may be, may be configured to take the action or provide the function, and may be programmed to take the action or provide the function. Disclosure of an action or function of the eye mask system 7000 is to be understood to be disclosure of an eye mask system 7000 configured (e.g. programmed) to perform the action or provide the function. Furthermore, where an action or function of the eye mask system 7000 is disclosed, it is to be understood that the eye mask system 7000 may be configured to perform a method comprising the action or function as a method step.

5.9.1 Eye Mask

In forms of the present technology the eye mask 7100 is a component, or assembly of components, that covers the eyes of the user. In different forms, the eye mask 7100 may completely cover one or both eyes of the user, or the eye mask 7100 may partially cover one or both eyes of the user. In certain forms the eye mask 7100 is opaque so that the no light can pass through the eye mask 7100 and reach the user's eyes. In other forms some or all of the eye mask 7100 is translucent so that it allows some light to pass through the eye mask 7100 and reach the user's eyes. In some forms the eye mask 7100 has an opaque mask part and a translucent mask part. It will be understood that the different forms of covering and opacity of the mask described here may be used in any of the forms of the technology described herein, unless the context clearly required otherwise. The eye mask 7100 may form part of an eye mask system 7000 comprising the eye mask 7100 and other components, such as a positioning and stabilising structure 3300 for the eye mask 7100.

The eye mask 7100 may cover the user's eyes to assist in sleep by reducing or eliminating ambient light perceivable by the patient's eyes. The eye mask 7100 may have an appearance similar to an eye mask or a VR/AR headset. With such an appearance the eye mask system 7000 may appear familiar to users, more like an item or clothing or an electronic accessory than a medical device used for treating a disorder. A more familiar/friendly appearance may avoid or reduce any tendency for the user to feel alienated when using the eye mask system 7000.

In some forms of the present technology, the eye mask 7100 may also comprise a display 7131 for displaying visual content to the user, e.g. in the manner of a virtual reality (VR) or augmented reality (AR) mask. The display 7131 will be described in more detail below. More generally, the eye mask system 7000 may comprise one or more transducers, such as sensors or output transducers, as will be described. The eye mask 7100 may comprise the one or more transducers and/or one or more other components.

5.9.1.1 Housing

The eye mask 7100 may comprise a housing to provide a support structure for components of the eye mask 7100, such as the display 7131 and any other components which may be inside or otherwise part of the eye mask 7100, such as transducers, processor 7900, memory 7910, communication module 7920 and/or flow generator 7400. The housing 7120 may additionally protect the display 7131 and/or other components of the eye mask 7100. The housing 7120 may be constructed from a material suitable to provide protection from impact forces. In some examples the housing 7120 may be constructed from a biocompatible material.

The housing 7120 may be constructed from hard, rigid or semi-rigid material, such as plastic. In certain forms the rigid or semi-rigid material may be at least partially covered with a soft and/or flexible material (e.g., a textile, silicone, etc.). This may improve biocompatibility and/or user comfort during contact between the user and the housing 7120, for example when the user touches the housing 7120 or grabs it with their hands.

The housing 7120 in accordance with other forms of the present technology may be constructed from a soft, flexible, resilient material, such as silicone rubber.

In some forms, the housing 7120 may have a substantially rectangular or substantially elliptical profile. The housing 7120 may have a three-dimensional shape with the substantially rectangular or substantially elliptical profile.

In the example shown in FIG. 7, the housing 7120 has an overall shape that includes a curve from a lateral direction towards a posterior direction on each lateral side of the housing 7120. This shape may approximate the curvature of a person's face, enabling the housing 7120 to "hug" the person's face such that it has a low profile. A low-profile eye mask 7100 may advantageously be easier to relax or sleep with. In some forms, an anterior-facing side of the housing 7120 has substantially the same shape as a posterior-facing side of the housing 7120.

In some forms the display 7131 is permanently integrated into the eye mask 7100, such as in the example shown in FIG. 17. The display 7131 may be a component usable only as a part of the eye mask system 7000. In some forms, the housing 7120 may enclose the display 7131, which may protect the display 7131 and/or limit user interference (e.g., moving and/or breaking) with the display 7131 or components thereof.

In certain forms, the display 7131 may be substantially sealed within the housing 7120, in order to limit the collection of dirt or other debris on the surface of the display 7131, which could negatively affect the user's ability to view an image output by the display 7131. The user may not be required to break the seal and access the display 7131, since the display 7131 is not removable from the housing 7120.

In other forms, the display 7131 is removably integrated into the housing 7120 such that it may also be a device usable independently of the eye mask system 7000. For example, the display 7131 may be provided on a smart phone or other portable electronic device.

The housing 7120 may also comprise any one or more of the features of a housing for head-mounted display device as described in International (PCT) Patent Application No. PCT/AU2021/050277, the entire contents of which are incorporated herein for reference.

5.9.1.2 Interfacing Structure

The eye mask 7100 comprises portions that contact the user in use, for example portions that contact the user's face. It is desirable to make the eye mask 7100 comfortable for a user to wear. A comfortable eye mask encourages the user to use the eye mask for longer periods compared to if the eye mask is less comfortable to wear. It is also desirable for the eye mask 7100 to reduce the amount of marking on the face of a user caused by wearing the eye mask 7100. A comfortable eye mask 7100 may also facilitate relaxation and may make it easy for the user to fall asleep.

The eye mask 7100 may comprise an interfacing structure 7140, as shown in FIG. 17. The eye mask 7100 of the eye mask systems 7000 shown in FIGS. 7, 9-12 and 15 may comprise the interfacing structure 7140 shown in FIG. 17 or an interfacing structure 7140 having an alternative configuration. The interfacing structure 7140 may be provided to a posterior side of the eye mask 7100 (e.g. to a posterior side of the housing 7120) and may be configured to engage the user's face in use. In certain forms of the technology the interfacing structure 7140 may comprises one or more cushion portions positioned on a user-contacting side of the eye mask 7100, for example on one or more posterior surfaces of the eye mask 7100.

In some forms, the interfacing structure 7140 in accordance with the present technology may be constructed from a biocompatible material. In some forms, the interfacing structure 7140 in accordance with the present technology may be constructed from a soft, flexible, and/or resilient material. In certain forms, the interfacing structure 7140 may comprise any one or more of the following materials: textile, fabric, foam and/or silicone.

The interfacing structure 7140 may contact sensitive regions of the user's face, which may be locations susceptible to discomfort. The interfacing structure 7140 may be configured to provide a cushioning effect at these sensitive regions, which may advantageously limit or avoid user discomfort while wearing the eye mask system 7000. These sensitive regions may include the user's forehead, and may include the region of the user's head that is proximate to the frontal bone, like the Epicranius and/or the glabella. This region may be sensitive because there is limited natural cushioning from muscle and/or fat between the user's skin and the bone. Similarly, the ridge of the user's nose may also include little to no natural cushioning. The interfacing structure 7140 may be configured to provide a cushioning effect in these regions. In some examples, the interfacing structure 7140 is configured to be more compliant in one region than in another region.

In some forms, the interfacing structure 7140 may comprise a single element. In some embodiments the interfacing structure 7140 may be designed for mass manufacture. For example, the interfacing structure 7140 may be designed to comfortably fit a wide range of different face shapes and sizes.

In some forms, the interfacing structure 7140 may include different elements that overlay different regions of the user's face. The different portions of the interfacing structure 7140 may be constructed from different materials, and provide the user with different textures and/or cushioning at different regions.

In certain forms, the interfacing structure 7140 may comprise a first cushion portion and a second cushion portion, wherein the first cushion portion has a greater thickness, and/or a greater user-contacting surface, than the second cushion portion, and wherein the first cushion portion is positioned in a portion of the eye mask 7100 that exerts a greater force on the user's face in use than the second cushion portion. Additionally, or alternatively, the first cushion portion may be positioned in a portion of the eye mask 7100 that contacts a part of the user's face in use that is more sensitive than a part of the user's face contacted in use by the second cushion portion, for example a nose-contacting portion.

In some forms, the interfacing structure 7140 is coupled to a surface of the eye mask 7100. In some examples the interfacing structure 7140 may comprise a compliant portion configured to engage the user's face and a clip portion being stiffer than the compliant portion and configured to secure the interfacing structure 7140 to the housing 7120 of the eye mask 7100.

In some forms, the interfacing structure 7140 may extend at least partially around the housing 7120, and may form a viewing opening. The viewing opening may at least partially receive the user's face in use. Specifically, the user's eyes may be received within the viewing opening formed by the interfacing structure 7140.

Alternatively, or additionally, the interfacing structure 7140 may comprise any one or more of the features of an interfacing structure as described in International Patent Application No. PCT/AU2021/050277.

5.9.1.2.1 Light Shield

Some forms of the eye mask system 7000 may include a light shield that may be constructed from an opaque material and may be configured to block ambient light from reaching the user's eyes. The light shield may be part of the interfacing structure 7140 or may be a separate element. In some examples the interfacing structure 7140 may form a light shield by shielding the user's eyes from ambient light, in addition to providing a comfortable contacting portion for contact between the eye mask 7100 and the user's face. In some examples a light shield may be formed from multiple components together blocking ambient light.

In certain forms, the light shield can obstruct ambient light from reaching an eye region, which may be formed within regions of the Epicranius, the user's sphenoid, across the outer cheek region between the sphenoid to the left or right zygomatic arch, over the zygomatic arch, across the inner cheek region from the zygomatic arches towards the alar crests, and on the users' nasal ridge inferior to the sellion to enclose a portion of the users' face therebetween.

In one form, the light shield may not contact the user's face around its entire perimeter. For example, the light shield may be spaced from the user's nasal ridge. The width of this spacing may be substantially small, so as to substantially limit the ingress of ambient light. However, the user's nasal ridge may be sensitive and easily irritated. Thus, avoiding direct contact with the user's nasal ridge may improve user comfort while wearing the eye mask system 7000.

5.9.1.2.2 Seal Forming Structure

In some forms, the interfacing structure 7140 forms as a seal-forming structure and may comprise a target seal-forming region. The target seal-forming region is a region on the seal-forming structure where sealing may occur. The region where sealing actually occurs—the actual sealing surface—may change within a given session, from day to day, and from user to user, depending on a range of factors including but not limited to, where the eye mask 7100 is placed on the face, tension in the positioning and stabilizing structure 3300, and/or the shape of a user's face.

In one form the target seal-forming region is located on an outside surface of the interfacing structure 7140. In certain forms, the entire perimeter of the interfacing structure 7140 may be configured to seal against the user's skin and block ambient light from reaching an eye region. The eye region may be formed within regions of the Epicranius, the user's sphenoid, across the outer cheek region between the sphenoid to the left or right zygomatic arch, over the zygomatic arch, across the inner cheek region from the zygomatic arches towards the alar crests, and on the users' nasal ridge inferior to the sellion to enclose a portion of the users' face therebetween.

In certain forms, this may seal around the user's eyes. The seal created by the seal-forming structure or interfacing structure 7140 may create a light seal, in order to limit ambient light from reaching the user's eyes.

When providing a seal-forming structure, the interfacing structure 7140 may contact sensitive areas on the user's face, like the user's nasal ridge. This contact may entirely prevent the ingress of ambient light. Sealing around the entire perimeter of the housing 7120 may improve performance of the eye mask system 7000. Additionally, biocompatible materials may be selected so that direct contact with the user's nasal ridge does not significantly reduce user comfort while wearing the eye mask system 7000.

In certain forms of the present technology, an eye mask system 7000 comprises a plurality of interfacing structures 7140, each being configured to fit to a different user's head size and/or shape range. For example, the eye mask system 7000 may comprise one form of interfacing structure 7140 suitable for a large sized head, but not a small sized head and another suitable for a small sized head, but not a large sized head. The different interfacing structures 7140 may be removable and replaceable so that different users with different sized heads may use the same eye mask system 7000.

5.9.1.2.3 Material Biocompatibility

Biocompatible materials are considered to be materials that undergo a full evaluation of their biological responses, relevant to their safety in use, according to ISO 10993-1 standard. The evaluation considers the nature and duration of anticipated contact with human tissues when in-use. In some forms of the present technology, the materials utilised in the positioning and stabilizing structure and interfacing structure may undergo at least some of the following biocompatibility tests:

Cytotoxicity—Elution Test (MeM Extract): ANSI/AAMI/ ISO 10993-5

Skin Sensitisation: ISO 10993-10

Irritation: ISO 10993-10

Genotoxicity—Bacterial Mutagenicity Test: ISO 10993-3

Implantation: ISO 10993-6

5.9.1.3 Sensors

In some forms of the present technology the eye mask system 7000 may comprise one or more transducers comprising, or in the form of, one or more sensors. A sensor may be understood to be a transducer that receives input energy, for example in a physical form (such as light, sound, temperature, motion, etc), and produces electrical energy, for example an electrical signal. Each sensor may comprise a plurality of components forming the sensor, for example in an assembly. In some examples the sensor or a component of the sensor may be physically separated from other components of the eye mask system 7000. That is, one or more sensors may be provided to the eye mask 7100. Alternatively, or additionally, one or more sensors may be provided to peripheral components such as a wristband. For example, an eye mask system 7000 may comprise an eye mask 7100 worn on a user's head and a sensor located elsewhere on the user's body, for example on the user's wrist, chest or finger. In some examples, one or more sensors may be physically separated from the user's body, for example located on a bedside table.

The one or more sensors may be configured to detect characteristics of the ambient environment, of the user's sleep and/or of the user (for example while awake or while asleep).

5.9.1.3.1 Electroencephalography (EEG)

In some examples of the present technology the eye mask system 7000 comprises an EEG sensor 7110.

The EEG sensor 7110 may comprise one or more sensor elements (e.g. forming one or more channels). In some examples the EEG sensor 7110 may comprise a plurality of sensor elements and may comprise an assembly. In some examples, the eye mask system 7000 may comprise a cap configured to be worn on the user's head, the cap including a plurality of sensor elements together forming an EEG sensor 7110. In some examples, the cap may be removably attached to other parts of the eye mask system 7000. The cap may form at least part of the positioning and stabilising structure 3300, for example.

In some examples the eye mask system 7000 may comprise a positioning and stabilising structure 3300 comprising an EEG sensor 7110. The EEG sensor 7110 may comprise a plurality of sensor elements positioned on the positioning and stabilising structure 3300. The sensor elements may be provided to one or more strap portions of the positioning and stabilising structure 3300, for example located on or embedded in strap portions of the positioning and stabilising structure 3300.

It is to be understood that the number of sensor elements forming the EEG sensor 7110 may vary between examples of the present technology.

5.9.1.3.2 Electrocardiogram (ECG)

In some examples of the present technology the eye mask system 7000 comprises an ECG sensor 7111.

The ECG sensor 7111 may comprise one or more sensor elements forming the ECG sensor 7111. The ECG sensor 7111 may comprise a plurality of sensor elements and may comprise an assembly. In some examples the eye mask system 7000 may comprise a plurality of electrodes configured to be attached to the user's body. The ECG sensor 7111 may comprise the electrodes or may be configured to receive signals from electrodes. The ECG sensor 7111 may generate an ECG signal or may generate signals from leads attached to the electrodes and transmit those signals to another component or processor which generates an ECG signal.

5.9.1.3.3 Pulse/HR

In some examples of the present technology the eye mask system 7000 comprises a heart rate sensor 7112 configured to detect the user's heart rate.

In some examples, the heart rate sensor 7112 may comprise an optical heart rate monitor assembly, for example comprising an LED and sensor element in contact with the user's skin configured to detect a pulse. The heart rate sensor 7112 may be in contact with the patient's forehead in use. The eye mask 7100 may comprise the heart rate sensor 7112. In another example, the eye mask system 7000 may comprise one or more ear buds comprising heart rate sensors 7112. In other examples, the heart rate sensor 7112 may comprise an electrical heart rate monitor assembly comprising a chest band worn around the user's chest.

In some examples the eye mask system 7000 may comprise a sensor element or assembly that provides both the ECG sensor 7111 and the heart rate sensor 7112.

5.9.1.3.4 Oxygen

In some examples of the present technology, the eye mask system 7000 comprises an oxygen saturation sensor 7113 configured to detect the user's blood oxygen saturation or generate a signal from which the user's blood oxygen saturation can be determined.

In some examples, the oxygen saturation sensor 7113 may comprise a photoplethysmogram (PPG) sensor such as a pulse oximeter. The oxygen saturation sensor 7113 may comprise a forehead pulse oximeter configured to detect the user's blood oxygen saturation. In some examples the eye mask 7100 comprises a forehead pulse oximeter. In other examples the oxygen saturation sensor 7113 may comprise a fingertip pulse oximeter or any other type of pulse oximeter such as an earlobe or toe pulse oximeter.

In some examples the eye mask system 7000 may comprise a sensor element or assembly that provides both the heart rate sensor 7112 and the oxygen saturation sensor 7113.

5.9.1.3.5 Blood Pressure (BP)

In some examples of the present technology the eye mask system 7000 comprises a blood pressure sensor 7114. The blood pressure sensor 7114 may generate a signal indicative of the patient's blood pressure, e.g. from which the patient's blood pressure can be determined or inferred.

In some examples, the blood pressure sensor 7114 comprises a cuffless blood pressure sensor. The cuffless blood pressure sensor may be incorporated into the eye mask 7100. Alternatively, the cuffless blood pressure sensor may be separate from the eye mask 7100 and may be configured to transmit a signal indicative of the user's blood pressure to the eye mask 7100. In other examples the blood pressure sensor 7114 comprises a blood pressure measuring system including a blood pressure measuring cuff and a pump unit for inflating the cuff. In some examples the pump unit is configured to transmit the user's blood pressure or a signal indicative thereof to the eye mask 7100.

In some examples the eye mask system 7000 comprises a sensor element or assembly that provides both the heart rate sensor 7112 and the blood pressure sensor 7114.

5.9.1.3.6 Accelerometer

In some examples of the present technology the eye mask system 7000 comprises an accelerometer 7115. The accelerometer 7115 may be configured to detect and/or capture movement and/or an orientation of the user (e.g. by detecting acceleration and determining movement). The accelerometer 7115 may, for example, be a 3-axis, 4-axis, 5-axis or 6-axis accelerometer. In some examples the accelerometer 7115 is provided to the eye mask 7100. In other examples the accelerometer 7115 is located within another component of the eye mask system.

5.9.1.3.7 Temperature

In some examples of the present technology the eye mask system 7000 comprises a body temperature sensor 7116. The body temperature sensor 7116 may comprise a contact thermometer or a non-contact thermometer. In some examples the body temperature sensor 7116 may comprise an infrared thermometer. The body temperature sensor 7116 may be provided to the eye mask 7100. In some examples the body temperature sensor 7116 may comprise an infrared thermometer provided to the eye mask 7100 and may be configured to measure the user's temperature via the user's forehead. Alternatively, the body temperature sensor 7116 may be provided to another component of the eye mask system 7000, such as a wrist band worn by the user. The body temperature sensor 7116 may measure the user's skin temperature.

In some examples of the present technology the eye mask system 7000 comprises an ambient temperature sensor 7117. The ambient temperature sensor 7117 may be provided to the eye mask 7100. Alternatively, the ambient temperature sensor 7117 may be provided to another component of the eye mask system 7000. In one form the ambient temperature sensor 7117 may be provided to a respiratory pressure therapy device 4000 configured to transmit ambient temperature measurements (e.g. a signal indicative thereof) to the eye mask 7100.

5.9.1.3.8 Humidity

In some examples of the present technology the eye mask system 7000 comprises an ambient humidity sensor. The ambient humidity sensor may be provided to the eye mask 7100. Alternatively, the ambient humidity sensor may be provided to another component of the eye mask system 7000. In one form the ambient humidity sensor may be provided to a respiratory pressure therapy device 4000 configured to transmit ambient humidity measurements or a signal indicative thereof to the eye mask 7100.

5.9.1.3.9 Microphone

In some examples of the present technology the eye mask system 7000 comprises a microphone 7118. The microphone 7118 may be provided to the eye mask 7100. Alternatively, another device, which may form part of the eye mask system 7000 or may communicate with the eye mask system 7000, such as the user's phone or a respiratory pressure therapy device 4000, may comprise a microphone 7118. The output of the microphone 7118 may be used by the eye mask system 7000 to detect breathing, snoring, apneas and/or ambient noise. In some examples the microphone 7118 may be used for voice input by the user.

5.9.1.3.10 Camera

In some examples of the present technology the eye mask system 7000 comprises a camera. The camera may be provided to the eye mask 7100. Alternatively, another device, which may form part of the eye mask system 7000 or may communicate with the eye mask system 7000, such as the user's phone or a respiratory pressure therapy device 4000, may comprise a camera.

The camera may be operable to capture individual images or video (which may be considered to be a plurality of images captured at intervals of sufficiently short time frame that the images, when played back in sequence, appear as video).

The output of the camera may be presented to the user of the eye mask system 7000 on display 7131, as explained further below.

In some examples the eye mask system 7000 comprises a plurality of cameras.

5.9.1.4 Examples of Analysis

In some forms of the present technology the eye mask system 7000 (e.g. the processor 7900) is configured to analyse the output of one or more sensors, such as one or more of the sensors described above. The eye mask system 7000 may be configured to analyse the output of a sensor and take an action based on the analysis. the eye mask system 7000 may be configured to identify sleep characteristics, identify a problem, predict an outcome and/or provide a recommendation to the user or a health service provider.

In some forms, the eye mask system 7000 may comprise an artificial intelligence (AI) module configured to perform these functions. In some forms, the eye mask system 7000 may comprise a machine learning (ML) module configured to perform these functions. The ML module may be partially trained or may be considered fully trained. In other forms these functions may be performed remotely, for example via one or more servers, for example servers operated by a developer of the eye mask system 7000. In such examples the eye mask system 7000 may communicate with said server to send data for analysis and receive the results.

5.9.1.4.1 Detection and Diagnosis

In some examples, the eye mask system 7000 may be configured to detect and/or diagnose a disorder. For example, the eye mask system 7000 may be configured to detect an apnea experienced by the user, or other respiratory events such as hypopnea or hypernea or gasping. The eye mask system 7000 may be configured to detect snoring by the user. In some forms the eye mask system 7000 may be configured to detect apneas, snoring or gasping from a bed partner of the user. In some examples, the eye mask system 7000 may monitor the user's breathing using the microphone 7118. The eye mask system 7000 may analyse the output of the microphone 7118 to detect an apnea or snoring. The eye mask system 7000 may be configured to detect low levels of oxygen, e.g. using the oxygen saturation sensor 7113 or other anomalies associated with sleep apnea e.g. high pulse, blood pressure or heart rate variability. In some examples the eye mask system 7000 may receive data representing apneas and/or snoring that has been detected by an RPT device 4000 also in use by the user, and may process that data, for example by keeping a log, presenting that data to the user, and/or recommending changes to the user. The eye mask system 7000 may be configured to perform a method or steps thereof described with reference to FIGS. 4D and 4E to detect sleep disordered breathing and/or diagnose a disorder.

In some examples the eye mask system 7000 may be configured to diagnose sleep disordered breathing (SDB), such as OSA, or provide sufficient information for a clinician to make a diagnosis. The eye mask system 7000 may diagnose SDB based on a severity or frequency of detected events such as apneas, hypopnea or hyperpnea, excessive snoring or the like. In some examples the eye mask system 7000 may be configured to detect bruxism, for example using the microphone 7118.

5.9.1.4.2 Sleep Detection and/or Awake Detection

In one example, the eye mask system 7000 is configured to identify that the user is sleeping. Alternatively or additionally, the eye mask system 7000 may be configured to identify that the user is awake.

The eye mask system 7000 may be configured to determine whether the user is asleep or awake based on signal(s) received from any one or more of the sensors of the eye mask system 7000, including but not limited to the EEG sensor 7110, HR sensor 7112, BP sensor 7114, body temperature sensor 7116 and microphone 7118.

The eye mask system 7000 (e.g. with processor 7900 and memory 7910) may be configured to determine that the user is awake or asleep and may keep a log of sleep times/durations, awake times/durations and may be configured to present that information to the user or a clinician.

5.9.1.4.3 Sleep Staging

In some examples the eye mask system 7000 may be configured to identify sleep stages. That is, the eye mask system 7000 may be configured to detect a user's stage of sleep. In some examples the eye mask system 7000 may be configured to identify REM sleep and non-REM sleep. In further examples, the eye mask system 7000 may be configured to identify awake time, light sleep, deep sleep and/or REM sleep. The eye mask system 7000 may be configured to record times and durations of sleep and/or sleep stages. The eye mask system 7000 may be configured to display a record of sleep stages to the user or a clinician.

The eye mask system 7000 may be configured to determine a sleep state or stage based on signal(s) received from any one or more of the sensors of the eye mask system 7000, including but not limited to the EEG sensor 7110, HR sensor 7112, BP sensor 7114, body temperature sensor 7116 and microphone 7118.

5.9.1.5 Output Transducers

In some examples of the present technology, the eye mask system 7000 comprises one or more transducers comprising, or in the form of, one or more output transducers. The output transducers may provide outputs of the eye mask system 7000. An output transducer may be understood to be a transducer that receives input in the form of electrical energy and produces energy in another form, for example a physical form (such as light, sound, temperature, motion, etc).

The eye mask system 7000 may operate the one or more output transducers to interact with the user. In some examples, the eye mask system 7000 may be configured to operate one or more output transducers to help the user fall asleep and/or help the user achieve better quality sleep. For example, the eye mask system 7000 may operate an output transducer to achieve one or more of longer sleep, deeper sleep, longer deep sleep, longer REM sleep, a good experience of waking up after sleep, and a good experience while awake. In further examples, the eye mask system 7000 may operate the one or more output transducers to interact with the user, for example for entertainment, education, relaxation and the like or to help the user fit or set up the eye mask system 7000.

5.9.1.5.1 Sound Transducer

In some examples of the present technology, the eye mask system 7000 comprises a sound transducer 7130. The sound transducer 7130 may be configured to produce sounds.

Sound may be provided through the user's ear canal or through the bones in the patient's skull. In particular examples, the sound transducer 7130 may comprise bone conduction transducers, earbuds, over-ear headphones or speakers. In some examples the sound transducer 7130 is connected to or formed as part of the eye mask 7100. In some examples the sound transducer 7130 may be connected to or formed as part of the positioning and stabilising structure 3300, for example connected to a backstrap 3310 of a positioning and stabilising structure 3300 of the eye mask system 7000.

In some examples, sound may not be provided directly to the user's ears or ear canal. Some users may prefer to have their ears uncovered/unblocked. In the example shown in FIG. 17, the eye mask 7100 comprises sound transducers 7130 in the form of two speakers, one on each lateral side of the eye mask 7100 and configured to direct sound in a substantially posterior direction towards the user's ears. The speakers may be contained within or connect to the housing 7120. The housing 7120, or separate speaker housings, as the case may be, may comprise two groups of holes formed in the housing 7120 proximate the speakers to facilitate and/or direct sound posteriorly.

In some forms of the technology, the sound transducer 7130 comprises an active noise control mechanism (which may alternatively be referred to as a noise cancellation or active noise reduction mechanism) configured to reduce certain sounds in the sound output to the user. For example, unwanted ambient sounds may be reduced by generating a sound wave in antiphase to a received sound wave and outputting the antiphase sound wave to the user.

5.9.1.5.2 Display

The eye mask 7100 of the eye mask system 7000 may block out substantially all the ambient light. This may assist the user in relaxing or falling asleep and may help the user maintain sleep, if desired by the user.

In some examples of the present technology, the eye mask system 7000 includes a display 7131. The display 7131 may be incorporated into the eye mask 7100, and may comprise a VR or AR display. In some examples the display may fill the user's full field of view. In other examples the display 7131 may comprise one or more light sources or display elements or screens within the user's field of view but not filling the entire field of view. The display 7131 may comprise a single display screen filling the user's full field of view, or may comprise two display components, such as two display screens, each corresponding to a respective one of the user's eyes.

5.9.1.5.2.1 Lenses and Display Screen

In some examples, the display 7131 comprises at least one lens 7134. The user may view an image provided by a display screen through the lens 7134. The at least one lens

7134 may assist in spacing the display screen away from the user's face to limit eye strain. The at least one lens 7134 may also assist in better observing the image being displayed by the display.

FIG. 17 shows one example of a display 7131 provided to an eye mask 7100. The display 7131, or any one or more features thereof, as shown in and described with reference to FIG. 17, may be applied to any of the other eye masks 7100 described herein. In the example shown in FIG. 17, the display 7131 comprises two lenses 7134. In general, where a feature of a single lens is described, the feature is to be understood to be applicable to each lens of a pair of lenses in examples in which the display 7131 comprises two lenses. Likewise, where reference is made to a feature of a single display screen, the feature is to be understood to be applicable to each of a pair of display screens. It is also to be understood that in some examples the display 7131 may comprise one display screen and two lenses.

In some forms, the lenses 7134 are Fresnel lenses.

In some forms, each lens 7134 may have a substantially frustoconical shape. A wider end of the lens 7134 may be disposed proximate to the display screen 3104, and a narrower end of the lens 7134 may be disposed proximate to the user's eyes, in use.

In some forms, the lens 7134 may have a substantially cylindrical shape, and may have substantially the same width proximate to the display screen, and proximate to the user's eyes, in use.

In some forms, the at least one lens 7134 may also magnify the image of the display screen, in order to assist the user in viewing the image.

In some forms, the head-mounted display system 7000 includes two lenses 7134 (e.g., binocular display), one for each of the user's eyes. In other words, each of the user's eyes may look through a separate lens positioned anterior to the respective pupil. Each of the lenses 7134 may be identical, although in some examples, one lens 7134 may be different than the other lens 7134 (e.g., may have a different magnification or may have a different shape such as a mirrored shape to provide a left side lens and a right side lens).

In certain forms, the display screen may output two images simultaneously. Each of the user's eyes may be able to see only one of the two images. The images may be displayed side-by-side on the display screen. Each lens 7134 permits each eye to observe only the image proximate to the respective eye. The user may observe these two images together as a single image.

In some forms, the posterior perimeter of each lens 7134 may be approximately the size of the user's orbit. The posterior perimeter may be slightly larger than the size of the user's orbit in order to ensure that the user's entire eye can see into the respective lens 7134. For example, the outer edge of the each lens 7134 may be aligned with the user's frontal bone in the superior direction (e.g., proximate the user's eyebrow), and may be aligned with the user's maxilla in the inferior direction (e.g., proximate the outer cheek region).

The positioning and/or sizing of the lenses 7134 may allow the user to have approximately 360° of peripheral vision in the virtual environment, in order to closely simulate the physical environment.

In some forms, the eye mask system 7000 includes a single lens 7134 (e.g., monocular display). The lens 7134 may be positioned anterior to both eyes (e.g., so that both eyes view the image from the display screen through the lens 7134), or may be positioned anterior to only one eye (e.g., when the image from the display screen is viewable by only one eye).

5.9.1.5.2.2 Lens Mounting

The lenses 7134 may be coupled to a spacer positioned proximate to the display screen (e.g., between the display screen and the interfacing structure 7140), so that the lenses 7134 are not in direct contact with the display screen (e.g., in order to limit the lenses 7134 from scratching the display screen).

The lenses 7134 may be recessed relative to the interfacing structure 7140 so that the lenses 7134 are disposed within the viewing opening. In use, each of the user's eyes are aligned with the respective lens 7134 while the user's face is received within the viewing opening (e.g., an operational position).

In some forms, the anterior perimeter of each lens 7134 may encompass approximately half of the display screen. A substantially small gap may exist between the two lenses 7134 along a centre line of the display screen. This may allow a user looking through both lenses 7134 to be able to view substantially the entire display screen and all displayed image/video/light output to the user.

In certain forms, the centre of the display screen (e.g., along the centre line between the two lenses 7134) may not output an image. For example, in a binocular display (e.g., where each side of the display screen outputs substantially the same image), each image may be spaced apart on the display screen. This may allow two lenses 7134 to be positioned in close proximity to the display screen, while allowing the user to view the entirety of the image displayed on the display screen.

In some forms, a protective layer 7135 may be formed around at least a portion of the lenses 7134, as shown in FIG. 17 for example. In use, the protective layer 7135 may be positioned between the user's face and the display screen.

In some forms, a portion of each lens 7134 may project through the protective layer 7135 in the posterior direction. For example, the narrow end of each lens 7134 may project more posterior than the protective layer 7135 in use.

In some forms, the protective layer 7135 may be opaque so that light from the display screen is unable to pass through. Additionally, the user may be unable to view the display screen without looking through the lenses 7134.

In some forms, the protective layer 7135 may be non-planar, and may include contours that substantially match contours of the user's face. For example, a portion of the protective layer 7135 may be recessed in the anterior direction in order to accommodate the user's nose.

In certain forms, the user may not contact the protective layer 7135 while wearing the eye mask system 7000. This may assist in reducing irritation from additional contact with the user's face (e.g., against the sensitive nasal ridge region).

5.9.1.5.3 Temperature Transducer

In some examples of the present technology, the eye mask system 7000 may comprise a temperature transducer 7132. The temperature transducer 7132 may be configured to adjust an actual or perceived temperature by the user.

In one form, the eye mask system 7000 may be configured to provide heating to the user with the temperature transducer 7132. In some examples, the temperature transducer 7132 may comprise a heating element. The heating element may be provided to the eye mask 7100, to the positioning and stabilising structure 3300 or to another component such as a cap, neck warmer or heated clothing.

In another form, the eye mask system 7000 may be configured to provide cooling to the user with the tempera-ture transducer 7132. In some examples, the temperature transducer 7132 may comprise a thermoelectric (Peltier) cooler. The thermoelectric cooler may be provided to the eye mask 7100, positioning and stabilising structure 3300 or another component. In one example the eye mask system 7000 may comprise a temperature transducer 7132 in the form of thermoelectric cooler provided to the eye mask 7100 and configured to cool the patient's forehead.

In another example, the temperature transducer 7132 may comprise a fan or air supply configured to cool the user via convective cooling.

The temperature transducer 7132 may comprise an assembly or system having both a heating and cooling device. For example, the temperature transducer 7132 may comprise both a heating element and a thermoelectric cooler. The temperature transducer 7132 may be operated heat or cool the user as required. In other examples the eye mask system 7000 may comprise multiple temperature transducers 7132, such as a first temperature transducer 7132 configured to provide heating and a second temperature transducer 7132 configured to provide cooling.

5.9.1.5.4 Scent Transducer

In some examples of the present technology the eye mask system 7000 may comprise a scent transducer 7133 configured to provide a scent to the user.

The scent transducer 7133 may comprise a material infused with a scent and an emitter, such as a valve openable to expose the material to the surrounding air, or a source of air be passed through or over the material. The scent transducer 7133 may comprise a material scented with a scent that is conducive to relaxation/sleeping. In some examples the scent transducer 7133 may be configured to release a lavender or chamomile scent. In some examples the scent transducer 7133 may comprise a removable and replaceable material, allowing the user to replace the material if the scent has been depleted or if a different scent is desired. The scent transducer 7133 may be provided to the eye mask 7100. The scent transducer 7133 may comprise a diffuser-type element, which may be a porous material, infused with a scent, through which air can flow in a torturous path to pick up the scent.

5.9.1.6 Examples of Operation of the Eye Mask System

The eye mask system 7000 in some examples may comprise a sleep mode or sleep-assist mode. The eye mask system 7000 may comprise one or more features or functions suitable for use when the user is asleep. In some forms, the eye mask system 7000 is configured to assist the user in sleeping and, in some examples, optimising sleep. The eye mask system 7000 may assist the user to fall asleep, stay asleep for longer, achieve a deeper sleep, maintain deep sleep for longer, wake up, wake up at an optimal time and/or wake up gently.

The eye mask system 7000 may determine a change which, if made, could improve the user's sleep. The eye mask system 7000 may receive an input from a sensor, determine an output, and operate an output transducer.

In some forms of the present technology, the eye mask system 7000 comprises an awake mode. The eye mask system 7000 may comprise one or more features or functions suitable for use when the user is awake. The eye mask system 7000 may operate in the awake mode when the user is awake and not intending to sleep. In some examples may detect that the user is awake and change to the awake mode from another mode (e.g. from a sleep mode or sleep-assist mode).

While in some examples of the present technology, the eye mask system 7000 may have one or more modes, such as an awake mode, a sleep mode and/or a sleep-assist mode, in some forms, the eye mask system 7000 may not have distinct operating modes. For example, the eye mask system 7000 may comprise various features, some of which may be intended for use during wakefulness and some of which may be intended for use during sleep or transitioning between wakefulness and sleep, but which are not associated with a particular operating mode. Any feature described herein as being a feature of a sleep mode or an awake mode or another mode is to be understood to be applicable to an eye mask system 7000 which does not operate in distinct modes.

5.9.1.6.1 Sound

In some examples the eye mask system 7000 is configured to play sound to the user via the sound transducer 7130 to encourage sleepiness or maintain sleep. In particular examples, the eye mask system 7000 is configured to play, with the sound transducer 7130, one or more of white noise, pink noise, calming noises such as ocean noise, fireplace noise, fan noise or the like, and/or music such as songs, lullabies or the like.

In some examples the eye mask system 7000 may be configured to play music. In some particular examples the eye mask system 7000 may be configured to play sound to accompany visual content provided by the display 7131.

In some examples the eye mask system 7000 may produce sounds, music or the like to facilitate sleep. In other examples the eye mask system 7000 may produce sounds, music or the like as part of entertainment for the user or to encourage relaxation.

5.9.1.6.1.1 Noise Cancellation

In some examples the eye mask system 7000 is configured to cancel noise. The eye mask system 7000 may be configured to operate the sound transducer 7130 to provide a noise cancellation effect to reduce or eliminate ambient noise, which may help the user relax, concentrate or sleep. For example, the eye mask system 7000 may operate the microphone 7118 to generate a signal representative of ambient noise and may operate the sound transducer 7130 to generate an audible sound antiphase to the ambient noise to cancel the ambient noise.

5.9.1.6.1.2 Wake-Up

In some examples the eye mask system 7000 is configured to play sound to the user via the sound transducer 7130 to wake the user up, preferably gently. The eye mask system 7000 may be configured to wake the user up at the end of a sleep cycle, for example before or around a particular time at which the user intends to wake up. In one example the eye mask system 7000 may be configured to play, with the sound transducer 7130, soft sounds of birds chirping, gentle music or other sounds to gently wake the user. The eye mask system 7000 may operate the sound transducer 7130 to gently ramp up the volume of the sounds to gently wake the user.

5.9.1.6.2 Display

The eye mask system 7000 may be configured to operate the display 7131 to provide visual content to the user, for example to help the user to fall asleep, to stay asleep, to achieve high quality sleep and/or to wake up. In some examples the eye mask system may be configured to provide visual content via the display 7131 for entertainment, relaxation, education, training or the like. The display 7131 may be configured to display images and/or video.

In some examples the display 7131 may be configured to provide visual content in the form of virtual reality (VR) and/or augmented reality (AR). Visual content displayed as AR may involve one or more images, or video, captured by the camera that is comprised as part of the eye mask system

7000 being displayed on display 7131. In one form, a real-time video of images captured by the camera is presented on display 7131.

In some examples the eye mask system 7000 may be configured to provide communication services for the user via the display 7131, such as a video call or video conferencing.

The eye mask system 7000 may be configured to provide visual content via the display 7131 together with audio content via the sound transducer 7130. That is, the eye mask system 7000 may be configured so that the user is able to watch audio-visual content, such as movies, television or other videos with sound, or engage in other activities involving audio and/or visual content, for example games.

5.9.1.6.2.1 Dusk-Mode

In some examples the eye mask system 7000 may be configured to help the user fall asleep using the display 7131. In some examples the eye mask system 7000 may be configured to simulate dusk with the display 7131. The eye mask system 7000 may be configured to display light visible to the user with the display 7131, the light having a predominantly red component, for a period of time to assist the user in falling asleep. That is, the light may be towards the red end of the visible light spectrum. The light may have substantially no blue component. Alternatively, the light may be white light with a greater red component than blue component.

In some forms, the eye mask system 7000 may change the spectrum of light displayed to the user on display 7131. For example, the spectrum change may be controlled to occur gradually. In some forms, the red component of the light spectrum may be gradually increased in comparison to other parts of the spectrum. This may simulate the change in spectrum of the setting sun as nightfall approaches and therefore create a natural environment for sleep. The change in the light spectrum may be controlled to occur over a time period similar to that for the setting sun.

Additionally or alternatively, the eye mask system 7000 may gradually dim the light over a period of time to assist the user to fall asleep (for example over a period of 15, 20, 30, 45, 60 minutes or the like). In some forms, the eye mask In some examples the eye mask system 7000 may display a video of a sunset on the display 7131.

5.9.1.6.2.2 Dawn-Mode

In some examples the eye mask system 7000 may be configured to wake the user up using the display 7131. In some examples the eye mask system 7000 may be configured to simulate dawn with the display 7131. The eye mask system 7000 may be configured to display light visible to the user with the display 7131, the light having a predominantly blue component, for a period of time to assist the user in waking up. That is, the light may be towards the blue end of the visual light spectrum. The light may have substantially no red component. Alternatively, the light may be white light with a greater blue component than red component.

A change in the spectrum of light displayed to the user on display 7131 may also occur in dawn-mode, and the spectrum change may be controlled to occur gradually. In some forms, the blue component of the light spectrum may be gradually increased in comparison to other parts of the spectrum. This may simulate the change in spectrum of the rising sun as dawn approaches and therefore create a natural environment for a user to arouse from sleep. The change in the light spectrum may be controlled to occur over a time period similar to that for the rising sun.

Additionally or alternatively, the eye mask system 7000 may increase the light intensity over a period of time to assist the user to wake up (for example over a period of 15, 20, 30, 45, 60 minutes or the like). In some examples the eye mask system 7000 may display a video of a sunset on the display 7131.

5.9.1.6.3 Heating and Cooling

The eye mask system 7000 may be configured to measure a temperature of the user and/or of the surroundings, for example with the body temperature sensor 7116 and/or the ambient temperature sensor 7117. The eye mask system 7000 may determine that heating is required and may operate the temperature transducer 7132 to provide heating. Alternatively, the eye mask system 7000 may determine that cooling is required and may operate the temperature transducer 7132 to provide cooling.

In some examples the user may provide an input to the eye mask system 7000, after which the eye mask system 7000 may operate the temperature transducer 7132 to provide heating or cooling based on the input.

In some examples the eye mask system 7000 may be configured to provide heating but not cooling, and vice versa. Where heating features and cooling features are described herein together, it is to be understood that the heating features may be applied in an eye mask system 7000 which does not have an ability to provide cooling. Likewise, it is to be understood that the cooling features may be applied to an eye mask system 7000 that does not have the ability to provide heating. Unless the context clearly requires otherwise, heating features and cooling features disclosed herein are to be understood to be independent features that are not inextricably linked.

In one example the eye mask system 7000 may determine that the room temperature is not ideal. The eye mask system 7000 may measure the ambient temperature with the ambient temperature sensor 7117. The eye mask system 7000 may determine that the ambient temperature is outside of a predetermined range (which may be defined by the user or other party, for example a physician) and prompt the user to adjust the room temperature. Alternatively, the eye mask system 7000 may operate the temperature transducer 7132 to heat or cool the user.

In another example, the eye mask system 7000 may determine that the user's body temperature is outside a predetermined range (which may be set by the user or other party, for example a physician). The eye mask system 7000 may measure the user's body temperature with the body temperature sensor 7116. The eye mask system 7000 may determine that the body temperature is outside of an ideal range and prompt the user to either adjust the room temperature or otherwise take steps to warm or cool themselves. In some examples the eye mask system 7000 may measure a rate of change of body temperature or ambient temperature and prompt the user to take steps based on the rate of change. In some examples the eye mask system 7000 may communicate with an air conditioning unit and may operate the air conditioning unit to heat or cool the room as required to maintain the ambient temperature or the user's body temperature within a predetermined range. The eye mask system 7000 may operate the temperature transducer 7132 to heat or cool the user, as required. In some forms, the temperature transducer 7132 is controlled to operate in combination with content presented to the user on display 7131. For example, the temperature transducer 7132 may be controlled to provide cooling if the display 7131 displays content associated with cold (e.g. a snowy landscape) and/or may be controlled to provide heating if the display 7131 displays content associated with heat (e.g. a desert landscape). Metadata may be included in the image data used to generate the display content that represents heating/cooling and is used to trigger a suitable change in operation of temperature transducer 7132.

In other examples, one or more algorithms and/or an AI module or a machine learning module, may be used to determine a desired temperature for the user. The desired temperature may be determined at one or more stages of the user's sleep cycles, for example: while falling asleep; during sleep; during REM sleep; and while waking up. The algorithm(s) and/or machine learning system may receive one or more parameters as inputs to the desired temperature determination process from sensors, for example ambient temperature, ambient humidity, time of day, medical condition information relating to the user, and sleep data. These parameters may be provided by sensors comprised as part of the eye mask system 7000 or may be provided by other sensors or systems. The desired temperature determined by the algorithms or machine learning system may be used by processor 7900 of eye mask system 7000 to control the temperature transducer 7132 as necessary.

5.9.1.6.4 Sleep Optimisation

In some examples of the present technology, the eye mask system 7000 may monitor or record sleep length or quality along with one or more other variables. The eye mask system 7000 may be configured to compare sleep length or quality with the one or more other variables and determine an effect on sleep length or quality of the one or more other variables. For example, the eye mask system 7000 may be configured to optimise the one or more other variables or recommend changes to the one or more other variables to the user. The other variables may be background noise, sleep position, sleep time, CPAP therapy pressure, PAP therapy type, activity before sleeping and the like. In some examples, the eye mask system 7000 may determine an optimum therapy pressure for a patient undergoing respiratory pressure therapy based on the effect of therapy pressure on outcomes such as sleep length, depth of sleep, time within particular sleep stages, AHI, user-reported sleep quality and the like.

5.9.1.6.4.1 Noise

In some forms, the eye mask system 7000 may determine that a particular background noise level or type of noise is ideal for a particular user to sleep well. The eye mask system 7000 may measure background noise levels and/or type of noise during sleep with the microphone 7118, monitor sleep quality and/or length and may provide feedback to the user regarding an optimal sleep noise level and type of noise. The eye mask system 7000 may prompt the user to play one or more of certain noise types, such as white noise, pink noise, ocean sounds, fireplace sounds or the like. The eye mask system 7000 may monitor sleep length and quality during each type of noise and may determine an optimal noise for good sleep for the user. The eye mask system 7000 may operate the sound transducer 7130 to cancel noise or provide a particular noise (e.g. white noise) which results in optimal sleep for the user.

5.9.1.6.4.2 Position

In another example, eye mask system 7000 may determine that a particular sleeping position is optimal for a particular user. In some examples, the eye mask system 7000 may determine that a user is at risk of having positional sleep apnea. The eye mask system 7000 may determine the user's sleeping position with the accelerometer 7115 (or another sensor) and may monitor sleep quality and length and determine an optimal position for good sleep for the user. While the user is awake, the eye mask system 7000 may provide feedback to the user regarding the optimal sleeping position based on the amount and/or quality of sleep determined by the eye mask system 7000 and the positions corresponding to that amount and/or quality of sleep. In some examples the eye mask system 7000 may be configured to compare frequencies of sleep disordered breathing events (e.g. apneas, hyperpneas, hypopneas, snoring, gasping or the like) in a plurality of different sleeping positions as determined using the accelerometer 7115 (for example by determining orientation of the eye mask 7100) and may determine a risk of positional sleep apnea based on the frequencies.

5.9.1.6.4.3 Wake Up Between Sleep Cycles

In some examples, the eye mask system 7000 may be configured to wake the user up during light sleep or between sleep cycles. Doing so may result in the user feeling more rested after waking. The eye mask system 7000 may be configured to identify that the user is in light sleep and wake the user. Alternatively, if the eye mask system 7000 determines that the user is not in light sleep, the eye mask system 7000 may be configured to gently rouse the user into a light sleep before then waking the user up completely. More generally, the eye mask system 7000 may be configured to change a sleep state of the user, e.g. without waking the user.

5.9.1.6.5 Sleep Data Reporting

In some examples of the present technology, the eye mask system 7000 may monitor or record properties of the user's sleep and save sleep data representative of the user's sleep in memory 7910. The eye mask system 7000 may be further configured to output the sleep data. The sleep data may be output in its raw form, or it may be output in a summary form, for example measures (e.g. averages, maxima/minima, etc) of sleep variables/characteristics over a period of time. The sleep data may be output on one or more external devices such as a remote external device 4286 and local external device 4288. The sleep data may be provided to the user, to a physician, clinician or other body (e.g. healthcare system, insurer).

Additionally, or alternatively, the sleep data may be analysed and used to generate other forms of feedback to the user. For example, the sleep data may be analysed to obtain a summary of a user's sleep behaviour over a period of time, for example a qualitative or quantitative expression of a user's sleep habits. In another example, analysis of the sleep data may be used to generate suggestions on how the user may improve their sleep, and the suggestions may be output via one or more external devices to any one or more of the parties described above.

5.9.1.6.6 Breath Training

In some examples of the present technology, the eye mask system 7000 may be configured to operate in a breath training mode. In some examples the eye mask system 7000 is configured to assist the user to breathe in a manner conducive to relaxation, meditation, sleeping or the like. In one form, the eye mask system 7000 may operate an output transducer, such as the display 7131, to provide a cue to prompt the user to breathe. The output transducer may provide the cue periodically and at a frequency which, when followed by the user, may result in the user achieving a relaxed or mediative state. Such a state may prepare the user for sleep and/or help the user fall asleep. The eye mask system 7000 may alternatively (or additionally) provide breathing cues via the sound transducer 7130, or via vibration in a manner conducive to relaxation and or sleep.

In some forms, the eye mask system 7000 may be configured to monitor the user's breathing during breath training. The eye mask system 7000 may receive a signal from any one of the sensors described above from which breathing can be detected and analyse and/or record the breathing.

In some examples the eye mask system 7000 may adjust the breathing cues based on the inputs from the sensors. In one example, the eye mask system 7000 may monitor the user's heart rate with the heat rate sensor 7112 and adjust the breathing cues based on the user's heart rate. For example, as the user's heart rate 7112 slows while the user relaxes, the eye mask system 7000 may reduce the frequency of the cues, encouraging further relaxation as the user becomes ready to relax to a greater extent.

In some examples the eye mask system 7000 may provide feedback to the user, for example regarding compliance with the breathing cues. In one example, the eye mask system 7000 may operate the display to advise the user to slow down or soften their breathing if the user is not breathing slowly or softly enough. The eye mask system 7000 may monitor the user's breathing using the microphone 7118 for compliance with the breathing cues. Alternatively, if the eye mask system 7000 is configured for respiratory pressure therapy (e.g. in an example described below) the eye mask system may monitor the user's breathing based on patterns in flow rate of air flowing from a flow generator (e.g. a blower) to a plenum chamber 3200 of the eye mask system 7000.

In some examples the eye mask system 7000 is configured to be used to assist/encourage sleep in the breath training mode. In some examples, in the breath training mode the eye mask system 7000 is configured to be used for relaxation or meditation while the user is awake. In some examples the breath training mode may be used for anti-anxiety purposes or to provide a calming effect.

5.9.2 Positioning and Stabilising Structure of the Eye Mask System

As described above, the eye mask system 7000 comprises a positioning and stabilising structure 3300. The positioning and stabilising structure 3300 may hold the eye mask 7100 in an in-use position.

The positioning and stabilizing structure 3300 may be configured to be comfortable against the user's head and may be configured to accommodate the weight of the eye mask 7100 in a manner that minimises facial markings and/or pain from prolonged use. In some examples the positioning and stabilising structure 3300 may provide for a universal (or at least near-universal) fit while providing for comfort, usability and cost of manufacture. The positioning and stabilising structure 3300 may be configured to be adjustable through a predetermined range, and may be adjustable with low-touch simple set up solutions that have a low dexterity threshold. Further considerations include catering for the dynamic environment in which the eye mask system 7000 may be used. As part of the immersive experience of a virtual environment, users may communicate, i.e. speak, while using the eye mask system 7000. In this way, the jaw or mandible of the user may move relative to other bones of the skull. Additionally, the whole head may move during the course of a period of use of the eye mask system 7000. For example, movement of a user's upper body, and in some cases lower body, and in particular, movement of the head relative to the upper and lower body.

In some examples the positioning and stabilizing structure 3300 provides a retention force to overcome the effect of the gravitational force on the eye mask 7100.

In some examples of the present technology, a positioning and stabilising structure 3300 is provided that is configured in a manner consistent with being comfortably worn by a user. In some example the positioning and stabilizing structure 3300 has a low profile, or cross-sectional thickness, to reduce the perceived or actual bulk of the apparatus. For example, the positioning and stabilizing structure 1300 may comprise at least one strap having a rectangular cross-section. In particular, positioning and stabilizing structure 3300 may comprise at least one flat strap.

In one form of the present technology, a positioning and stabilizing structure 3300 is provided that is configured so as not to be too large and bulky to prevent the user from comfortably moving their head from side to side.

In one form of the present technology, a positioning and stabilizing structure 3300 comprises a strap constructed from a laminate of a textile user-contacting layer, a foam inner layer and a textile outer layer. In one form, the foam is porous to allow moisture, (e.g., sweat), to pass through the strap. In one form, a skin contacting layer of the strap is formed from a material that helps wick moisture away from the user's face. In one form, the textile outer layer comprises loop material to engage with a hook material portion.

In certain forms of the present technology, a positioning and stabilizing structure 3300 comprises a strap that is extensible, e.g. resiliently extensible. For example the strap may be configured in use to be in tension, and to direct a force to draw the eye mask 7100 toward a portion of a user's face, particularly proximate to the user's eyes and in line with their field of vision.

In some examples, the positioning and stabilising structure 3300 comprises a tie, the tie being constructed and arranged so that at least a portion overlies a region of the user's head superior to an otobasion superior of the patient's head in use.

In the example shown in FIG. 7, the positioning and stabilising structure 3300 comprises a backstrap 3310. The backstrap 3310 forms a tie. The backstrap 3310 passes around the posterior side of the user's head. Each end of the backstrap 3310 is connected to a respective lateral side of the eye mask 7100. The backstrap 3310 in this example is a wide band. A wide backstrap 3310 may spread the force it applies to the user's head over a large surface area, resulting in a low pressure applied to the user's head. The user may find a lower pressure more comfortable than a higher pressure. The backstrap 3310 may be adjustable in length and/or angle. In some examples the backstrap is detachable from the eye mask 7100.

The backstrap 3310 may overlie the parietal bones of the user's skull, or the parietal bones and a superior portion of the occipital bone. The backstrap 3310 overlies a region of the user's head superior to an otobasion superior of the user's head in use.

FIG. 14 shows a positioning and stabilising structure 3300 comprising a backstrap and a face support portion 3320. The face support portion 3320 is configured to overlie the patient's cheeks and forehead in use without blocking the user's vision (or with only minor blockage). The face support portion 3320 may provide a large surface area over which the tension in the backstrap is able to be distributed, in order to exert a low force on the user's face. The eye mask 7100 may be attached to the face support portion 3320 and/or the backstrap 3310.

In some examples, the positioning and stabilising structure 3300 pulls the eye mask 7100 towards and on to the user's face. By pulling the eye mask 7100 onto the user's face, some of the weight of the eye mask 7100 can be supported by the user's cheeks and forehead, along with friction between the eye mask 7100 and the user's face.

FIG. 18 shows another example of a positioning and stabilising structure 3300, which may form part of an eye mask system 7000 together with any of the eye masks 7100 shown in FIG. 7, 9-13, 15 or 17, for example. In the FIG. 18 example the positioning and stabilising structure 3300 comprises a parietal strap portion 3311 configured to overlie the parietal bones of the user's head. The positioning and stabilising structure 3300 also comprises an occipital strap portion 3312 configured to overlie or lie inferior to the occipital bone of the user's head. Furthermore, in this particular example, the positioning and stabilising structure 3300 comprises a pair of lateral strap portions 3313 each configured to be located on a respective lateral side of the user's head in use and configured to connect the eye mask 7100 to the parietal strap portion 3311 and occipital strap portion 3312.

The parietal strap portion 3311 and the occipital strap portion 3312 may anchor against posterior surfaces of the user's head. The lateral strap portions 3313 may be configured to be in tension in use to pull the eye mask 7100 in a posterior direction causing it to engage the user's face.

In some examples, the lateral strap portions 3313 may be configured to attach to the eye mask 7100 by passing through openings in the eye mask 7100, for example in the housing 7120 or in arms extending from the housing 7120, and looping back and securing to themselves, for example with a hook-and-loop connection, mechanical fastener, magnetic connection, press studs or another suitable connection. By pulling a sufficient amount of each lateral strap portion 3313 through the opening in the housing 7120 or arm before securing each lateral strap portion 3313 to itself, the user can tighten the lateral strap portions 3313 and generate tension to hold the eye mask 7100 on their head.

For example, the eye mask 7100 shown in FIG. 17 comprises a pair of arms 3330 extending from the housing 7120. Each arm 3330 is located on a respective lateral side of the housing 7120 and is configured to attach to a respective lateral strap portion 3313. Each arm 3330 comprises an opening at a posterior end thereof through which a lateral strap portion 3313 can pass through and secure back onto itself after being tightened by the user. As shown in FIG. 18, the positioning and stabilising structure 3300 may comprise a pair of lateral strap portions 3313 having respective end portions 3314 each able to be passed through the opening in a respective arm 3330 and then secured back onto the respective lateral strap portion 3313. In this example the end portions 3314 comprise a hook material configured to attach to a loop material provided to the lateral strap portions 3313.

The positioning and stabilising structure 3300 may be flexible and/or elastic to enable donning of the eye mask system 7000 without adjustment of the lateral strap portions 3313. That is, once the user has adjusted the lateral strap portions 3313, the eye mask system 7000 may be configured (e.g. with sufficient flexibility and/or elasticity in the positioning and stabilising structure 3300 and overall system) to enable doffing and donning of the eye mask system 7000 with further adjustment of strap portions. In this way the positioning and stabilising structure 3300 may provide for set-and-forget adjustment.

The positioning and stabilising structure 3300 may also be as described in any of the examples in International Patent Application No. PCT/AU2021/050277, the entire contents of which are incorporated herein for reference.

5.9.2.1 Arms

The arms 3330 may be any rigid or semi-rigid (e.g. stiff enough to support its own shape) connectors extending from the eye mask 7100 (for example from the housing 7120 thereof) for connection to the positioning and stabilising structure 3300. In some examples the arms 3330 are formed from a thermoplastic material. In some examples, the arms 3330 are formed from a thermoplastic elastomer, such as Hytrel. The arms 3330 may be substantially inextensible.

The arms 3330 may be aligned generally with the anterior-posterior directions. In some examples the arms 3330 are configured aligned substantially parallel to the sagittal plane of the user's head in use. In some examples the arms 3330 are configured to be angled with respect to the sagittal plane so as to extend posteriorly and laterally.

The arms 3330 and/or lateral strap portions 3313 may be configured to be aligned parallel to the Frankfort horizontal plane of the user's head in use and superior to the zygomatic bones (e.g. above the user's cheek bones). In some examples the arms 3330 may extend from the housing 7120 in a posterior and superior direction. In some forms, the arms 3330 and/or lateral strap portions 3313 may be configured to be located superior to the anti-helix of each of the user's ears in use. In some examples the arms 3330 are configured to rotate with respect to the housing 7120. The arms 3330 may be pivotally connected to the housing 7120.

The arms 3330 may be elongate. The cross section of each arm 3330 may be substantially flat. For example, each arm 3330 in cross section may be greater in size in an axis aligned with the superior-inferior directions in use than in an axis aligned with the medial-lateral directions in use. The cross-sectional shape of each arm may be multiple times larger in the superior-inferior axis than in the medial-lateral axis, for example at least 3 times larger, at least 5 times larger, at least 8 times larger or at least 10 times larger.

In some forms, the arms 3330 may each have a three-dimensional shape which has curvature in all three axes (X, Y and Z). Although the thickness of each arm 3330 may be substantially uniform, its height may vary throughout its length. The purpose of the shape and dimension of each arm 3330 is to conform closely to the head of the user in order to remain unobtrusive and maintain a low profile (e.g., not appear overly bulky).

In certain forms, a flexible and/or resilient material may be provided around the rigid or semi-rigid material of the arms 3330. The flexible material may be more comfortable against the user's head than the material forming the arm 3330, in order to improve wearability and provide soft contact with the user's face. In one form, the flexible material is a textile sleeve at is permanently or removably coupled to each arm 3330.

In one form, a textile may be over-moulded onto at least one side of the arm 3330. In one form, the arm 3330 may be formed separately to the resilient component and then a sock of user contacting material (e.g., Breath-O-Prene™) may be wrapped or slid over the arm 3330. In alternative forms, the user contacting material may be provided to the arm 3330 by adhesive, ultrasonic welding, sewing, hook and loop material, and/or stud connectors.

In some forms, the user contacting material may be on both sides of the arm 3330, or alternatively may only be on the user contacting side (e.g., the user-contacting or user-facing side) of the arm 3330 which may advantageously reduce bulk and cost of materials.

The arms 3330 may also be as described in any of the examples in International Patent Application No. PCT/AU2021/050277, the entire contents of which are incorporated herein for reference.

5.9.3 Eye Mask System for Respiratory Pressure Therapy

FIG. 9 shows an eye mask system 7000 according to another form of the present technology. In this form, the eye mask system 7000 is configured to provide respiratory pressure therapy to a patient, such as CPAP. The eye mask system 7000 in this form is a patient interface. In the context of an eye mask system 7000 for providing respiratory pressure therapy, the user of the eye mask system 7000 may be a patient. More generally, a person using the eye mask system 7000 is a user, and may or may not be a patient. Where reference is made to a patient in description herein of a feature or function of an eye mask system 7000, it is to be understood that the feature or function may be used by any user. Likewise if reference is made to a user, the feature or function being described may be used by, or during treatment of, a patient.

The eye mask system 7000 shown in FIG. 9 may comprise any one or more the components and features described with reference to FIGS. 7 and 8. In addition, the eye mask system 7000 comprises a plenum chamber 3200, for example as described above. The plenum chamber 3200 may be pressurisable to a therapeutic pressure of at least 6 cmH$_2$O above ambient air pressure (and in other examples at least 2, 4, 10, 20 or 30 cmH$_2$O). The eye mask system 7000 may include a plenum chamber inlet port sized and structured to receive a flow of air into the plenum chamber 3200 at the therapeutic pressure for breathing by a patient.

In the FIG. 9 example, the eye mask system 7000 is configured to leave the patient's mouth uncovered. In examples in which the eye mask system 7000 comprises a seal-forming structure 3100 which covers the mouth of the patient, the eye mask system 7000 may be configured to allow the patient to breath from ambient through their mouth in the absence of a flow of pressurised air into the plenum chamber 3200, for example through an anti-asphyxia valve (AAV).

5.9.3.1 Seal-Forming Structure

The eye mask system 7000 shown in FIG. 9 also comprises a seal-forming structure 3100. The seal-forming structure 3100 is constructed and arranged to form a seal with a region of the patient's face surrounding an entrance to the patient's airways. The seal-forming structure 3100 has a hole therein such that the flow of air at said therapeutic pressure is delivered to at least an entrance to the patient's nares. The seal-forming structure 3100 is constructed and arranged to maintain said therapeutic pressure in the plenum chamber 3200 throughout the patient's respiratory cycle in use.

In this example, the seal-forming structure 3100 is attached to the eye mask 7100. The seal-forming structure 3100 may be removable from the eye mask 7100 for cleaning and replacement. In some examples of the present technology the eye mask 7100 may be able to be used as an eye mask (e.g. a smart eye mask as described above) without a seal-forming structure 3100 attached.

In the FIG. 9 example a portion of the seal-forming structure 3100 is visible. The seal-forming structure 3100 at least partially defines the plenum chamber 3200. The seal-forming structure 3100 seals to inferior surfaces of the patient's nose in use. The seal-forming structure 3100 may seal to an inferior periphery of the patient's nose in use. The seal-forming structure 3100 may be identified as a "cradle" cushion and may form a seal around the nares of the patient. The seal-forming structure 3100 may not enter the nares of the patient, although in other examples of the present technology may comprise nasal pillows which enter the nares to form a seal around the edges of the nares. The seal-forming structure 3100 may seal to an inferior and/or anterior surfaces of the patient's nose tip and may comprise a recessed portion configured to receive the patient's nose tip. The seal-forming structure 3100 may seal below a bridge of the nose.

In some examples the of the present technology the seal-forming structure 3100 may comprise a pair of posterior corners each configured to seal to the patient's face at a location lateral to and/or inferior to a respective one of the patient's nasal ala. The posterior corners may each seal to the patient's face at a location proximate a respective one of the patient's nasolabial sulci, at a location between a respective one of the nasolabial sulci and a respective nasal ala and/or at a location where a respective nasal ala joins to an anterior-facing surface of the patient's face.

In other examples the seal-forming structure 3100 may comprise a nasal cushion configured to seal around the patient's nose including on the nose above the patient's nose tip, a full-face cushion configured to seal around the patient's nose and mouth including on the nose above the patient's nose tip, an ultra-compact full face cushion configured to seal around the patient's nose and mouth and to an inferior and/or anterior surface of the patient's nose, and/or a nasal pillows cushion.

5.9.3.2 Positioning and Stabilising Structure

As described above with reference to FIG. 7, the eye mask system 7000 may comprise a positioning and stabilising structure 3300 to hold the eye mask 7100 in an in-use position on the patient's face. An eye mask system 7000 configured for providing respiratory pressure therapy may include any of the features of the positioning and stabilising structure 3300 described above with reference to FIGS. 7 and 8.

In the FIG. 9 example, the positioning and stabilising structure 3300 of the eye mask system 7000 also provides a force to hold the seal-forming structure 3100 in a therapeutically effective position on the patient's head. The positioning and stabilising structure 3300 may provide a force large enough to hold the eye mask 7100 and seal-forming structure 3100 in position while compensating for pressure within the plenum chamber 3200 exerting a force on the patient's face which tends to separate the seal-forming structure 3100 from the patient's face.

5.9.3.3 Vent

The FIG. 9 example of the eye mask system 7000 may also comprise a vent 3400 (not shown). The vent 3400 may allow a flow of gases exhaled by the patient from an interior of the plenum chamber 3200 to ambient. The vent flow of gases may be a continuous flow of gases. The vent 3400 may be sized and shaped to maintain the therapeutic pressure in the plenum chamber 3200. The vent 3400 may comprise a plurality of holes through which gas can flow from the plenum chamber 3200 to ambient.

5.9.3.4 Supply of Pressurised Flow of Gas

The FIG. 9 example of the eye mask system 7000 may comprise a flow generator (not shown) configured to generate a pressurised flow of gas. The eye mask 7100 in this example comprises the flow generator. The flow generator is internal to the eye mask 7100. The flow generator is fluidly connected to the plenum chamber 3200. Accordingly, the pressurised flow of gas is provided by the flow generator to the plenum chamber 3200 for breathing by the patient. The seal-forming structure 3100 seals around the patient's airways to maintain a therapeutic pressure within the plenum chamber 3200 in use.

In other examples of the present technology, the eye mask system 7000 is configured to receive a pressurised flow of gas from an air circuit 4170. The air circuit 4170 may convey the flow of gas from an RPT device 4000 to the eye mask system 7000 for breathing by the patient. The eye mask system 7000 may comprise a connection port 3600 configured to fluidly connect to an air circuit 4170. The air circuit 4170 may comprise a tube that is configured to connect to the eye mask system 7000.

FIG. 10 shows an eye mask system 7000 in which the eye mask 7100 comprises a connection port 3600. In this example, the connection port 3600 is located centrally at an anterior and inferior portion of the eye mask 7100. The connection port 3600 is proximate the plenum chamber 3200. The connection port 3600 may swivel around a central axis of the connection port 3600. In another example the connection port 3600 may be provided to an elbow provided to the eye mask 7100, the elbow being configured to connect to the air circuit 4170. The elbow may have a bend in it (such as a 90-degree or 135-degree bend) to enable the tube to extend in a substantially inferior direction which respect to the eye mask 7100. In the example shown in FIG. 10 the tube extends in a partially inferior and partially anterior direction. The elbow may swivel. The elbow may comprise a ball and socket joint or a joint configured to allow rotation of the elbow with respect to the eye mask 7100 about a plurality of axes. The eye mask 7100 may comprise a "tube down" configuration or a "tube up" configuration.

FIG. 11 shows an eye mask system 7000 in which the connection port 3600 is located atop the patient's head. In this example the eye mask system 7000 comprises headgear tubes 3350 configured to connect between the eye mask 7100 and a connection port 3600 at a superior location on the patient's head. In this example the headgear tubes 3350 form conduit headgear, forming part of the positioning and stabilising structure 3300. The headgear tubes 3350 may provide a force, along with a backstrap 3310, to hold the seal-forming structure 3100 in sealing position in use. In other examples the headgear tubes 3350 may not provide a force to the seal-forming structure 3100 but may enable the connection port 3600 to be located at a superior surface of the patient's head so that the air circuit 4170 is not located in front of the patient's face or body in use.

FIG. 12 shows another eye mask system 7000 comprising a connection port 3600. In this example the eye mask system 7000 comprises a short tube 4175. The connection port 3600 is provided at a distal end of the short tube 4175. The short tube 4175 is a tubing portion of the eye mask system 7000 in fluid connection with the plenum chamber 3200. An air circuit 4170 is able to be connected to the connection port 3600. The short tube 4175 is configured to convey a pressurised flow of breathable gas to the plenum chamber 3200. The short tube 4175 may at least partially decouple the eye mask system 7000 from the air circuit 4170. The connection of the air circuit 4170 to the eye mask system 7000 via a flexible short tube 4175 may advantageously reduce tube drag. In the example shown in FIG. 12 the short tube 4175 extends from a lateral portion of the eye mask 7100. In other examples the short tube 4175 may connect to the eye mask 7100 at an anterior location, for example extending inferiorly from a central and anterior location on the eye mask 7100 (e.g. in a tube-down configuration).

5.9.3.5 Cushion Module

The eye mask systems 7000 shown in FIGS. 9-11 each comprise a cushion module 3150. The cushion module 3150 comprises the seal-forming structure 3100 and may define some or all of the plenum chamber 3200. In some examples the cushion module comprises a seal-forming structure 3100 connected to a chassis portion, the seal-forming structure 3100 and chassis portion together forming some or all of the plenum chamber.

The cushion module 3150 may be removable and replaceable, allowing the user to remove the cushion module 3150 for cleaning and to replace it with a new cushion module 3150 at the end of its working life. Cushion modules 3150 may be provided in multiple shapes and/or sizes that fit a particular eye mask 7100, allowing an eye mask system 7000 to fit a wide range of patients.

FIG. 19 shows a schematic view of an anterior and medial portion of an eye mask 7100 having a removable cushion module 3150. The eye mask 7100 is configured to cover the user's eyes in use and may have any one or more of the features of an eye mask 7100 described elsewhere herein, such as one or more transducers configured to influence the user's sleep and/or detect characteristics of the user's sleep and/or detect characteristics of the user during sleep.

In the FIG. 19 example the cushion module 3150 is formed from a flexible material, for example an elastomeric material such as silicone or TPE. The cushion module 3150 is removably attachable to the eye mask 7100. The cushion module 3150 in this example has an anterior hole which can be stretch fitted to a corresponding portion of the eye mask 7100 to removably attach it to the eye mask 7100. In other examples the cushion module 3150 may comprise a substantially rigid clip configured to snap fit to the eye mask 7100 to removably attach the cushion module 3150 to the eye mask 7100. The user may use the eye mask system 7000 without a cushion module 3150 by manually removing the cushion module 3150 prior to use. The user may use the eye mask system 7000 with the cushion module 3150 fitted by attaching the cushion module 3150 prior to use.

As illustrated, the cushion module 3150 comprises a seal-forming structure 3100 and partially defines a plenum chamber 3200 fluidly connected to the connection port 3600. In use, the plenum chamber 3200 is filled with air at the therapeutic pressure for breathing by the user. The plenum chamber 3200 is attached to a housing 7120 of the eye mask 7100.

As shown in FIG. 19, the eye mask system 7000 comprises a connection port 3600 configured to fluidly connect to and receive a pressurised flow of air from an air circuit 4170 at a therapeutic pressure for breathing by the user. In other examples, the eye mask system 7000 comprises a flow generator 7400 (for example integrated into the eye mask 7100, e.g. attached to the housing 7120) configured to generate the pressurised flow of air at said therapeutic pressure. The eye mask system 7000 may also comprise a vent (not shown in FIG. 19) to allow a continuous flow of gases exhaled by the patient from an interior of the plenum chamber to ambient, said vent structure being sized and shaped to maintain the therapeutic pressure in the plenum chamber in use. The vent may be formed by a plurality of holes in the housing 7120 and/or a wall of the plenum chamber 3200.

The eye mask 7100 may be configured to receive a plurality of different sized cushion modules 3150. This may accommodate a wider range of users. An eye mask system 7000 may comprise an eye mask 7100 and a plurality of cushion modules 3150 each having a different size to the others. The eye mask 7100 shown in FIG. 19 forms part of an eye mask system 7000 that may be configured to operate whether or not a cushion module 3150 is fitted. As will be described, the eye mask system 7000 may be operable in a non-treatment mode in which no respiratory pressure therapy is provided to the user. The eye mask system 7000 may be operable in the non-treatment mode independently of whether or not the cushion module 3150 is attached to the eye mask 7100. The eye mask system 7000 may be operable in the non-treatment mode in the absence of a cushion module 3150, e.g. when no cushion module 3150 is fitted to the eye mask 7100.

As will be described below, in some examples, the seal-forming structure 3100 may be movable between a non-contact position in which the seal-forming structure 3100 does not contact the user and a sealing position in which the seal-forming structure 3100 is able to form a seal to the user's face. In some examples the cushion module 3150 is able to move relative to the eye mask 7100. The cushion module 3150 may be movable between a non-contact position in which the seal-forming structure 3100 does not contact the user and a sealing position in which the seal-forming structure 3100 is able to form a seal to the user's face.

Also shown in FIG. 19 is the interfacing structure 7140 connected to a portion of the eye mask 7100 superior to the cushion module 3150. The portion of the interfacing structure 7140 shown in FIG. 19 is configured to engage the bridge of the user's nose to create a light seal.

5.9.3.6 Decoupled Cushion Module

FIG. 13 shows a schematic illustration of an eye mask system 7000. The eye mask system 7000 in this example comprises an eye mask 7100 and positioning and stabilising structure 3300, which may have any of the features described above with reference to FIGS. 7-11. The eye mask 7100 comprises a cushion module 3150 having a seal-forming structure 3100. The cushion module 3150 at least partly defines the plenum chamber 3200 in the example. As described above the cushion module 3150 may be removably attachable to the eye mask 7100.

5.9.3.6.1 Movement of Position and Orientation

The cushion module 3150 in this example of the present technology is able to move relative to the eye mask 7100. FIG. 13 indicates with arrows a number of ways in which the cushion module 3150 may move with respect to the eye mask 7100.

The cushion module 3150 is able to change position with respect to the eye mask 7100. Additionally, the cushion module 3150 is able to change orientation with respect to the eye mask. In other examples of the present technology, the cushion module 3150 is able to change position, but not orientation, with respect to the eye mask 7100, or vice versa. In further examples, the cushion module 3150 may be fixed in place with respect to the eye mask 7100.

To change position with respect to the eye mask 7100, the cushion module 3150 may be able to translate. The cushion module 3150 may be able to translate with respect to the eye mask 7100 along an anterior-posterior axis, as shown by arrows B in FIG. 13. Additionally, or alternatively, the cushion module 3150 may be able to translate with respect to the eye mask 7100 along a left-right axis, as shown by arrows A in FIG. 13. In some examples, the cushion module 3150 may be able to translate with respect to the eye mask 7100 along a superior-inferior axis.

To change orientation with respect to the eye mask 7100, the cushion module 3150 may be able to rotate. The cushion module 3150 may be able to rotate with respect to the eye mask 7100 in the left-right direction about an axis oriented in the superior-inferior direction, as shown by arrows C in FIG. 13. Additionally, or alternatively, the cushion module 3150 may be able to rotate with respect to the eye mask 7100 in the superior-inferior direction about an axis oriented in the left-right direction, as shown by arrows D in FIG. 13. In some examples, the cushion module 3150 may be able to rotate with respect to the eye mask 7100 in the anterior-posterior direction about an axis.

5.9.3.6.2 Adjustability

One way in which the cushion module 3150 may be able to move with respect to the eye mask 7100 (e.g. move in the ways described above) is that it may be able to be moved, for example by the patient or a clinician, to adjust the cushion module 3150. The cushion module 3150 may be able to be moved into a position and/or orientation consistent with a good fit on a particular user or patient.

In some examples, the position and/or orientation of the cushion module 3150 with respect to the eye mask 7100 may be able to be adjusted. In some examples the cushion module 3150 may be secured to the eye mask 7100 and held in position by static friction sufficiently strong that the cushion module 3150 does not move when not intended to be moved, for example during use of the eye mask system 7000. However, the static friction may be weak enough that the patient or clinician is able to push, pull or rotate (as the case may be) the cushion module 3150 into a desired position and/or orientation. In another example the cushion module 3150 may be attached to the eye mask 7100 with a locking mechanism configured to lock the position and/or orientation of the cushion module 3150, but allow the user or clinician to unlock the locking mechanism to move the cushion module 3150 to change its position and/or orientation.

An eye mask system 7000 with a cushion module 3150 that is able to be moved for adjustment may advantageously enable the eye mask system 7000 to be used by a wider range of users. Alternatively, or additionally, a cushion module 3150 movable for adjustment may advantageously enable individual users to achieve a good fit.

5.9.3.6.3 Decoupling

Another way in which the cushion module 3150 may move with respect to the eye mask 7100 (in the ways described above), is that it may be at least partially decoupled from the eye mask 7100. Decoupling the cushion module 3150 from the eye mask 7100 may provide for a comfortable fit of the eye mask system 7000 to the patient. An at least partially decoupled cushion module 3150 may enable the cushion module 3150 to move to accommodate the facial geometry of a particular patient, resulting in a comfortable and stable fit.

The cushion module 3150 may be attached to the eye mask 7100 by a flexible connection to enable some movement (e.g. in any one or more of the directions described above) of the cushion module 3150 with respect to the eye mask 7100. For example, the cushion module 3150 may attach to a portion of the eye mask 7100 formed from a resilient material such as silicone. Alternatively, or additionally, the cushion module 3150 may be attached to the eye mask 7100 by one or more hinges configured to allow the cushion module 3150 to move in position and/or orientation with respect to the eye mask 7100.

A cushion module 3150 decoupled from the eye mask 7100 to allow at least some movement with respect to the eye mask 7100 may also allow the eye mask system 7000 to tolerate forces applied to the eye mask 7100 that may otherwise disrupt the seal formed by the seal-forming structure 3100 to the patient's face. Forces applied to the eye mask 7100 in use, such as from the patient's pillow when the patient turns their head to the side, may advantageously not be passed on to the seal-forming structure 3100 in examples in which the cushion module 3150 is at least partially decoupled from the eye mask 7100.

While the cushion module 3150 illustrated in FIG. 13 is a cradle cushion, in other examples the cushion module 3150 may be another type, for example nasal pillows cushion, full face cushion, nasal cushion or oro-nasal cushion. In the case of an oro-nasal cushion, the cushion module 3150 may comprise a nasal portion and an oral portion. The nasal portion and oral portion may be decoupled from each other. In other examples the eye mask system 7000 may comprise a nasal cushion module and an oral cushion module, which may be partially or fully decoupled from each other.

5.9.3.6.4 Actuated Cushion Module

Another way in which the cushion module 3150 may be able to move with respect to the eye mask 7100 is that it may be actuated by the eye mask 7100. The eye mask 7100 may comprise one or more actuators configured to move the cushion module 3150 in position and/or orientation. The actuators may be rotary or linear and may be electronically powered, e.g. small electric motors, servomotors or stepper motors, small linear actuators, electromagnets paired with magnets or ferromagnetic components, among other suitable options. Alternatively, one or more of the actuators may be pneumatically powered, for example powered by breathable gas under pressure passing through the plenum chamber 3200 during use of the eye mask system 7000 for respiratory pressure therapy, controlled either by the magnitude of therapy pressure and/or by opening/closing of valves.

5.9.3.6.4.1 Actuation Based on Patient Input

In some examples the cushion module 3150 may be moved in position and/or orientation by actuators by way of adjustment of the cushion module 3150, for example to achieve a better fit. The patient may provide input to the eye mask system 7000 through a user control interface to activate one or more actuators to change a position and/or orientation of the cushion module 3150 during fitting.

5.9.3.6.4.2 Actuation Based on Therapy Pressure

In some examples, actuation of the cushion module 3150 may be controlled by the eye mask system 7000 (for example the processor 7900 thereof) without input from the patient. In some examples eye mask system 7000 may actuate the cushion module 3150 to urge it to move towards the patient's face to increase a sealing force. In this example, there may be only a little movement of the cushion module 3150 but the force with which the seal-forming structure 3100 is held against the patient's face may increase. In some examples, the eye mask system 7000 may actuate the cushion module 3150 to provide a sealing force corresponding to a particular therapy pressure. That is, the cushion module 3150 may be actuated with a force substantially equal to or corresponding to a minimum force required to maintain a seal at a particular therapy pressure.

The eye mask system 7000 may also be configured to actuate movement of the cushion module 3150 in response to events during use of the eye mask system 7000. For example, on detection of a leak in seal-forming structure 3100 the actuators may be actuated to move the seal-forming structure 3100 closer to the user's face in order to try to reduce or prevent the leak. In another example, the cushion module 3150 may be slowly moved towards the user's face during a ramp-up stage of the supply of pressurised gas so that the force exerted by the cushion module 3150 on the user's face corresponds to the therapy pressure. At higher therapy pressures the seal-forming structure 3100 is required to be held against the patient's face with a higher force than at lower therapy pressures, in order to counter the higher force acting to move the plenum chamber 3200 away from the patient's face which results from a higher therapy pressure. An eye mask system 7000 which actuates the cushion module 3150 to provide a sealing force corresponding to therapy pressure may advantageously be able to minimise the force with which the cushion module 3150 is held against the patient's face, since only the minimum required force is used.

5.9.3.6.4.3 Actuation Between Non-Contact and Sealing Positions

In further examples, the cushion module 3150 may be actuated between a non-contact position and a sealing position. The non-contact position may be a position in which the cushion module 3150 is not in contact with the patient's face. The sealing position may be a position in which the cushion module 3150 is able to provide respiratory pressure therapy to the patient. The eye mask system 7000 (or the processor 7900 thereof) may be configured to move the cushion module 3150 to a non-contact position for when therapy is not being provided and move the cushion module 3150 to a sealing position for when therapy is being provided to the patient. This may advantageously allow the patient to wear the eye mask system 7000 without the feel of the cushion module 3150 on their face when not receiving treatment.

In some examples, the eye mask system 7000 (e.g. with the processor 7900) may be configured to detect whether the user is awake or asleep and move the cushion module 3150 to the sealing position only once the user has fallen asleep. This may allow the user to fall asleep without the feel of the cushion module 3150 on their face while still enabling the user to receive respiratory pressure therapy once they have fallen asleep.

5.9.3.6.4.4 Actuation Based on Orientation

In some examples, the eye mask system 7000 may be configured to detect an orientation of the eye mask 7100, for example with the accelerometer 7115 or other orientation sensor. The eye mask system 7000 may be configured to actuate the cushion module 3150 to apply a force to it based on the orientation of the eye mask 7100.

In some examples the eye mask system 7000 may actuate the cushion module 3150 to compensate for movement or weight of the eye mask 7100. For example, if the patient moves their head to its side while sleeping, the eye mask 7100 may move laterally with respect to the patient's face (e.g. downwards with respect to gravity), under its own weight. In response to this orientation, the eye mask system 7000 may actuate the cushion module 3150 to move towards the opposite lateral direction with respect to the patient's face (e.g. upwards with respect to gravity) to compensate for the lateral pull on the eye mask 7100. In some examples the eye mask system 7000 may actuate the cushion module 3150 to rotate towards the patients nose when the eye mask 7100 is pulled downwards by gravity.

5.9.3.7 Setup and Troubleshooting Mode

The eye mask system 7000 may comprise or be configured to operate in a setup and troubleshooting mode (a "setup mode"). In the setup mode the eye mask system 7000 may be configured to assist the user to setup and/or begin using the eye mask system 7000 shown in any one of FIGS. 7, 9-12, 15 and 18. In the setup mode the eye mask system 7000 may be configured to assist the user in setting up the eye mask system 7000 for use as a patient interface, for example for treatment of sleep disordered breathing, where the eye mask system 7000 is so configured.

The eye mask system 7000 may be configured to present a tutorial to the user to assist the user with fitting and/or setup. The eye mask system 7000 may operate the display 7131 and/or sound transducer 7130 to provide information and/or instructions regarding setup of the eye mask system 7000, such as how to fit the eye mask system 7000. The eye mask system 7000 may be configured to provide a video tutorial to the user with instructions regarding setup. The eye mask system 7000 may be configured to assist the user to fit the eye mask system 7000 correctly for use as a patient interface for respiratory pressure treatment of sleep disordered breathing.

In some examples, in the setup mode, the eye mask system 7000 may provide troubleshooting. For example, the if the user has begun using the eye mask system 7000 but is experiencing a problem. The eye mask system 7000 may be operable in the setup mode to repeat a setup procedure to troubleshoot specific problems. For example, the eye mask system 7000 may be configured to provide a series of instructions (e.g. with the display 7131 or sound transducer 7130) to setup the eye mask system 7000 from scratch. Alternatively, the eye mask system 7000 may identify that a problem exists, or may receive an input from the user identifying a problem. The eye mask system 7000 may be configured to provide instructions regarding troubleshooting and/or solving the problem.

In certain forms, the user may be able to communicate with, or receive communications from, another party through communication module 7920 in a "remote assistance" mode. In remote assistance mode the user may be in communication with human assistance, for example a person who can provide technical assistance in the use of the eye mask system (e.g. a representative of the manufacturer of the eye mask system 7000) and/or a person who can provide medical assistance (e.g. a physician or clinician). Alternatively, or additionally, the user may be in communication with artificial assistance, for example an algorithmic or machine learning-based assistance module. Remote assistance mode may be triggered based on certain events detected by processor 7900, for example if set up takes more than a predetermined amount of time, or if a threshold number of operation errors are detected during setup.

5.9.3.7.1 Setup Sensors

In some examples, the eye mask system 7000 may be configured to monitor one or more signals received from one or more sensors of the eye mask system 7000 during setup. The eye mask system 7000 may provide feedback to the user regarding setup based on the one or more signals.

In one form of the present technology, the eye mask system 7000 may comprise a strap tension sensor. The strap tension sensor may be configured to generate a signal indicative of tension in the backstrap 3310 or one or more other straps of the positioning and stabilising structure 3300, such as lateral strap portions 3313. The eye mask system 7000 may be configured to measure tension of the backstrap 3310 with the strap tension sensor and provide feedback to the user based on the tension. For example, the eye mask system 7000 may advise the user, for example by operating the display 7131 or sound transducer 7130, that the backstrap 3310 is too loose, too tight or tightened correctly. In some examples the strap tension sensor comprises a strain gauge provided to the strap. In some examples the strap tension sensor comprises a stretch sensor having a capacitance which varies with extension of the sensor (or a portion thereof) from an unstretched length. In other examples the sensor may have a resistance which varies with extension.

In some examples of the present technology, the eye mask system 7000 may comprise a strap angle sensor. The strap angle sensor may be configured to generate a signal indicative of an angle of the backstrap 3310, lateral strap portions 3313 or other strap(s) of the positioning and stabilising structure 3300. The angle may be with respect to a feature of the eye mask 7100, for example a backstrap connection portion at which the backstrap 3310 connects to the eye mask 7100. The eye mask system 7000 may be configured to measure an angle of the backstrap 3310 with the strap angle sensor and provide feedback to the user. For example, the eye mask system 7000 may advise the user, for example by operating the display 7131 or sound transducer 7130, that the backstrap 3310 is too high, too low or angled correctly. In some examples the strap angle sensor comprises a strain gauge. In one form the eye mask system 7000 may comprise a stretch sensor provided between the backstrap 3310 and a strap connection portion of the eye mask 7100 such that angular adjustment of the strap changes an amount of stretch of the sensor. The strap angle sensor may be offset from an axis about which the strap is able to pivot during angular adjustment of the strap such that changes in strap angle result in changes in extension of the stretch sensor. The sensor may have a resistance and/or capacitance that varies with extension of the sensor (or a portion thereof) from an unstretched length.

Where the positioning and stabilising structure 3300 comprises multiple strap portions, such as shown in FIG. 17, a stretch sensor may be provided between any one strap portion and any other strap portion, to determine an angle between the two strap portions. Alternatively or additionally, any one or more of the strap portions may comprise stretch sensors each configured to measure elongation of the respective strap portions. In some examples the positioning and stabilising structure 3300 comprises multiple stretch sensors to detect tension or elongation in strap portions and multiple stretch sensors to detect angles between strap portions and/or angles between strap portions and the eye mask 7000, such that complete information on the geometry and forces in the headgear in use is acquirable.

In some forms, the eye mask system 7000 comprises an eye mask compression sensor configured to generate a signal indicative of the force with which the eye mask 7100 is pulled towards the patient's face. The eye mask compression sensor may be provided between the eye mask 7100 and the patient's face or may be provided between a portion of the eye mask 7100 configured to be in contact with the patient's face in use, such as a foam layer, and another portion of the eye mask 7100 such as a frame or housing. The eye mask system 7000 may be configured to measure a force with which the eye mask 7100 is pulled against the patient's face and provide feedback to the user regarding tension of the backstrap 3310. The eye mask compression sensor may comprise a load cell. In one example the eye mask compression sensor may have a resistance and/or capacitance that varies in relationship with a compression force applied to the eye mask compression sensor.

5.9.3.7.2 Leak Detection

In some examples, in the setup mode the eye mask system 7000 (e.g. the processor 7900 thereof) may be configured to detect a leak during use of the eye mask system 7000 for respiratory pressure therapy. A leak may occur between a seal-forming structure 3100 of the eye mask system 7000 and a surface of the patient's face. In other examples, a leak may occur between components of the eye mask system 7000, such as between a cushion module 3150 and portion of the eye mask 7100 to which cushion module 3150 is fluidly connected. In some examples the eye mask system 7000 may be configured to detect leaks even when the eye mask system 7000 is not operating in a setup mode, for example when the eye mask system 7000 is operating in a therapy mode.

In some examples, the eye mask system 7000 may detect a leak and alert the user to the existence of the leak, for example using one or more transducers. For example, the eye mask system 7000 may detect a leak and operate the display 7131 and/or sound transducer 7130 to alert the user or prompt the user to reconfigure the eye mask system 7000 or take another step, such as changing a position.

In some examples the eye mask system 7000 may determine a magnitude of one or more leaks, such as a leak flow rate. The eye mask system 7000 may operate a transducer such as the display 7131 or sound transducer 7130 to inform the user of the magnitude of the leak.

In some examples, the eye mask system 7000 may operate a transducer to provide feedback regarding the existence and/or magnitude of leaks during fitting of the eye mask system 7000. The eye mask system 7000 may be configured to identify leaks and provide feedback in real time during fitting of the eye mask system 7000 to enable the user to adjust the eye mask system 7000 to minimise or substantially eliminate leaks during setup.

In some examples, the eye mask system 7000 may be configured to determine a location of a leak. Unless the context clearly requires otherwise, any reference to determining a location of a leak is not to be understood as determining a location within absolute precision. In one example, the location of a leak may be determined in the sense that the leak has been determined to be on a particular side of the seal-forming structure, even if the precise location of the leak on that particular side of the seal-forming structure has not been determined. In some examples, the eye mask system 7000 may be configured to detect a leak and provide an indication of the location of the leak to the patient.

In one example the eye mask system 7000 may be configured to distinguish between leaks on the left side of a seal-forming structure 3100 and leaks on the right side of the seal-forming structure 3100. The eye mask system 7000 may comprise a pair of microphones 7118 provided to each lateral side of the eye mask 7100. The eye mask system 7000 may operate the pair of microphones 7118 to determine the side of the seal-forming structure 3100 with the leak, for example by comparing sound levels.

In other examples the eye mask system 7000 may be configured to distinguish between leaks on a superior side of the seal-forming structure 3100 and the inferior side of the seal-forming structure 3100. In further examples the eye mask system 7000 may be configured to distinguish between leaks occurring at three, four or more locations on the seal-forming structure.

The eye mask system 7000 may be configured to provide feedback to the user to indicate the location of a leak. The user may then reconfigure the eye mask system 7000 to eliminate or reduce the leak. In some examples the eye mask system 7000 may be configured to provide instructions regarding reducing or eliminating a leak, based on a location of the leak. For example, the eye mask system 7000 may be configured to detect that a leak is occurring on a left side of the seal-forming structure 3100 and prompt the user to rotate the seal-forming structure towards the left side (in the case of a seal-forming structure 3100 being rotatable for adjustment). Alternatively, the eye mask system 7000 may be configured to detect that a leak is occurring and prompt the user to tighten the backstrap 3310.

As discussed above, in some examples of the present technology, the eye mask system 7000 may be configured to actuate a cushion module 3150 to move the cushion module in position and/or orientation. In some examples, the eye mask system 7000 may be configured to detect a leak and determine at least an approximate location with respect to the seal-forming structure 3100 of the leak. The eye mask system 7000 may be further configured to actuate the cushion module 3150 based on the detection of the leak to at least reduce a magnitude of the leak. In some examples, the eye mask system 7000 may be move the cushion module 3150 as required to eliminate the leak. In some circumstances further adjustment of the eye mask system 7000 or its the positioning and stabilising structure 3300 may be required. However, if only a small adjustment to the cushion module 3150 is required, an eye mask system 7000 configured to automatically detect and resolve a leak may advantageously require minimal adjustment by the user, resulting in an eye mask system 7000/patient interface that may be user-friendly and may be easy to use.

5.9.3.7.3 Onboarding

In some examples of the present technology, the eye mask system 7000 may be configured to ease new patients into respiratory pressure therapy. During operation in the setup mode, or in a separate onboarding mode, the eye mask system 7000 may be configured to execute an onboarding process.

In the onboarding process, after the patient has donned and otherwise fitted and set up the eye mask system 7000, the eye mask system 7000 may be configured to operate one or more transducers, such as the display 7131 and sound transducer 7130 to provide breathing cues to encourage the patient to breathe normally and thereby relax, which may prevent claustrophobia. The eye mask system 7000 may be configured to monitor the patient's adherence to the breathing cues using one or more sensors, such as the microphone 7118 and may monitor the patient's relaxation level, for example with the heart rate sensor 7112, blood pressure sensor 7114, oxygen saturation sensor 7113 and/or body temperature sensor 7116.

In a further step of the onboarding process, the eye mask system 7000 may be configured to begin providing positive airway pressure, for example by activation and control of a separate RPT device 4000 or by control of an integrated flow generator 7400 of the eye mask system 7000. In some examples, the eye mask system 7000 may be configured to initially provide a low airway pressure (e.g. 4 cmH$_2$O or 2 cmH$_2$O-6 cmH$_2$O, for example) for a predetermined period of time. The eye mask system 7000 may also provide breathing cues while providing positive airway pressure, for example to encourage normal breathing and help prevent the patient feeling claustrophobic. The eye mask system 7000 may be configured to increase positive airway pressure to a therapy pressure from a lower pressure than the therapy pressure. In some examples the eye mask system 7000 may be configured to gradually increase positive airway pressure to a therapy pressure (e.g. by increasing pressure in steps or by continuously ramping up pressure). In some examples the eye mask system 7000 may increase airway pressure based on adherence to breathing cues and/or a level of patient relaxation as determined by sensor outputs.

5.9.3.8 Integrated Flow Generator

FIG. 15 shows an eye mask system 7000 according to another example of the present technology. In this form, the eye mask system 7000 comprises a flow generator 7400. As illustrated, the flow generator 7400 is attached to the eye mask 7100. The flow generator 7400 is provided to an anterior side of the eye mask 7100 and in a medial location. In this example, the eye mask system 7000 forms a head-worn PAP system.

The flow generator 7400 is configured to provide a pressurised flow of breathable gas to a plenum chamber 3200 for breathing by the patient, for example for treatment of sleep disordered breathing. In this example the flow generator 7400 is fluidly connected to the plenum chamber 3200 through the eye mask 7100. The eye mask system 7000 comprises a cushion module 3150 having a seal-forming structure 3100. In this example the cushion module 3150 at least partially defines the plenum chamber 3200.

FIG. 16 shows a block diagram of components of the eye mask system 7000 shown in FIG. 15. In this example the eye mask system 7000 comprises all of the sensors and transducers described with reference to FIGS. 7 and 8, along with a processor 7900, memory 7910 and communication module 7920. In addition, the eye mask system 7000 comprises a flow generator 7400 controllable by the processor 7900. In some examples the flow generator 7400 may comprise its own processor or controller, in addition to the processor 7900.

In other examples, the eye mask system 7000 may comprise a flow generator 7400 supported at a superior location on the patient's head and fluidly connected to the plenum chamber 3200. The flow generator 7400 may be supported on the patient's head by the positioning and stabilising structure 3300 of the eye mask system 7000.

The flow generator 7400 may be as described, or have any one or more of the features described in WO2012/113027 or WO2018/018074, the entire contents of each of which are hereby incorporated by reference.

5.9.3.8.1 Non-Therapeutic Features

In some examples, the eye mask system 7000 may comprise a flow generator 7400 (e.g. examples described above with reference to FIGS. 15 and 16), but may not be configured for respiratory pressure therapy, or may be configured for another use in addition to providing respiratory pressure therapy. Furthermore, eye mask systems according to examples of the present technology may be configured to provide non-therapeutic features at the same time as therapeutic features such as respiratory pressure therapy.

5.9.3.8.2 Flow Generator for Sensory Effect

The eye mask system 7000 may not include a seal-forming structure or a plenum chamber from which the user can breathe a pressurised flow of air. Instead the user may breathe air from ambient and the flow generator 7400 may be used for other purposes. In such an embodiment, the eye mask system 7000 may comprise an eye mask 7100 comprising a flow generator 7400 in the manner shown in FIG. 15, but not comprising a seal-forming structure 3100 as shown in FIG. 15.

The operation of the flow generator 7400 may be controlled by the processor 7900. In some examples, eye mask system 7000 is configured to operate the flow generator 7400 based on input from the user. In other examples the eye mask system 7000 may be configured to operate the flow generator 7400 based on input from one or more sensors of the eye mask system 7000.

In some examples, the eye mask system 7000 may be configured to provide a sensory effect to the user with the flow generator 7400.

In one example the eye mask system 7000 may be configured to simulate wind or a breeze on the user's head or face. The eye mask system 7000 may be configured to generate a flow of air with the flow generator 7400. The eye mask system 7000 may be configured so that the flow of air passes over and in contact with the user's head and/or the user's face. The simulation of wind may increase the realism of a simulation provided to the user by the eye mask system 7000, for example the flow generator 7400 may be configured to operate in co-ordination with content displayed on display 7131. In one example the eye mask system 7000 may be configured to simulate a relaxing outdoor environment, using the display 7131 and the sound transducer 7130 (and optionally other transducers. The eye mask system 7000 may be configured to simulate a light breeze across the patient's head, face and/or body. This may further immerse the user in the simulated environment. In another example the eye mask system may be configured to simulate an active outdoor environment, such as a cycling, racing, skiing or the like. The eye mask system 7000 may be configured to simulate the high-speed environment with a high flow of air across the user's face and/or head. Flow generator control data may be incorporated into media data, for example as meta-data, that is processed by processor 7900 to present media to the user and also to control operation of the flow generator 7400.

5.9.3.8.3 Heating and/or Cooling with the Flow Generator

In one form the flow generator 7400 may be used as a fan. The eye mask system 7000 may be configured to provide heating and/or cooling to the user with the flow generator 7400. As described above, the eye mask system 7000 may comprise a temperature transducer 7132. The eye mask system 7000 may be configured to operate both the temperature transducer 7132 and the flow generator 7400 to provide heating and/or cooling. For example, the eye mask system 7000 may be configured to generate a flow of air with the flow generator 7400 and heat and/or cool the flow of air with the temperature transducer 7132.

In some examples, the temperature transducer 7132 or a portion thereof is provided in the flow of air generated by the flow generator 7400, for example in a conduit or otherwise in the flow path.

5.9.3.9 Providing Respiratory Pressure Therapy

As described above, in some forms the eye mask system 7000 is configured to connect to an RPT device 4000 via an air circuit 4170 connected to a connection port 3600 of the eye mask system. In other forms the eye mask system 7000 may comprise a flow generator 7400, for example attached to the eye mask 7100 or positioning and stabilising structure 3300.

Whether the source of a pressurised flow of breathable gas is an RPT device 4000 to which the eye mask system 7000 is connected via an air circuit 4170 or a flow generator 7400 forming part of the eye mask system 7000, the eye mask system 7000 may be configured to control respiratory pressure therapy provided to the patient. The eye mask system 7000 may control a separate RPT device 4000 with the processor 7900 via the communication module 7920. Alternatively, the processor 7900 of an eye mask system 7000 may control a head mounted flow generator 7400 more directly. Unless the context clearly requires otherwise, any features or functions relating to the provision, operation, control or the like of respiratory pressure therapy by an eye mask system 7000 described herein are to be understood to be applicable to either of these forms of the present technology.

In some examples, eye mask system 7000 is configured to provide respiratory pressure therapy (e.g. by operating an integrated flow generator 7400 or a separate RPT device 4000) based on parameters set by the patient (e.g. therapy pressure, therapy type and the like). In other examples the eye mask system 7000 may be configured to provide respiratory pressure therapy based on input from one or more sensors of the eye mask system 7000.

5.9.3.9.1 Sleep Stages and Therapy

In some examples, the eye mask system 7000 is configured to determine whether the user is awake or asleep. For example, the eye mask system 7000 may be configured to detect that the user is awake, asleep, waking and/or falling asleep. The eye mask system 7000 may be configured to provide respiratory pressure therapy only if the user/patient is asleep. For example, the eye mask system 7000 may be configured to switch from a non-treatment mode to a treatment mode upon detection that the user is asleep. In some examples the eye mask system 7000 may be configured to provide respiratory pressure therapy only after a predetermined length of sleep duration or in response to an apnea. As described above, the respiratory pressure therapy may comprise providing a flow of air at a therapeutic pressure for breathing by a user/patient.

In some examples, the eye mask system 7000 may be configured to ramp up or otherwise gradually increase the therapeutic pressure once the patient is detected to be asleep. The eye mask system 7000 may be configured to adjust the rate at which therapeutic pressure is ramped up based on the patient's sleep state or stage. For example, if the patient is detected to be sleeping deeply but the therapeutic pressure is not yet at a predetermined (e.g. target) therapy pressure the eye mask system 7000 may increase the rate at which the therapeutic pressure is ramped up.

In some examples the eye mask system 7000 may operate in a sleep-assist mode or a sleep mode depending on whether the user is attempting to sleep (sleep-assist mode) or is asleep (sleep mode). For example, the eye mask system 7000 may be configured to detect that the user is awake and operate in a sleep-assist mode. The eye mask system 7000 may be configured to detect that the user is asleep and operate in a sleep mode. In some examples, the eye mask system 7000 is configured to begin respiratory pressure therapy upon a change from the sleep-assist mode to the sleep mode. In some examples, airway pressure is ramped up slowly during the sleep-assist mode and then ramped up more quickly in the sleep mode. In some examples the eye mask system 7000 may operate in a REM mode and an NREM mode, depending on whether the user is in REM sleep or NREM sleep.

The eye mask system 7000 may be configured to assist the user to fall asleep and/or remain asleep during respiratory pressure therapy. The eye mask system 7000 may operate one or more of the transducers described herein to do so. Such transducers may comprise one or more sensors configured to detect characteristics of the ambient environment, or the user's sleep and/or of the user. The eye mask system 7000 may be configured to analyse an output of one or more of the sensors and take an action based on the analysis. For example, the eye mask system 7000 may be configured to optimise user's sleep and may be configured to determine a change which, if made, could assist the user to fall asleep and/or remain asleep.

In some examples, the eye mask system 7000 may be configured to adjust the therapeutic pressure of the flow of air based on an output of one or more of the sensors. In some examples, the eye mask system 7000 is configured to detect that the user is waking up (for example with the EEG sensor 7110, microphone 7118, accelerometer 7115 or another sensor) and reduce the therapeutic pressure in response. This may assist the user to remain asleep. In some examples, the eye mask system 7000 may be configured to reduce the therapeutic pressure upon detection of ambient noise (for example above a predetermined threshold), which may also assist the user remain asleep.

In some examples, the eye mask system 7000 may comprise a microphone 7118 and a sound transducer 7130 (for example earbuds or headphones, which may be attached to the eye mask 7100 or positioning and stabilising structure 3300). The eye mask system 7000 may be configured to provide a noise cancelling effect using the sound transducer 7130 upon detection of ambient noise, for example ambient noise above a predetermined threshold. This may make it easier for the user to remain asleep. The production of a noise cancelling effect is described elsewhere herein and may comprise producing sound in antiphase to the ambient sound as detected with the microphone 7118. In some examples the eye mask system 7000 may be configured to provide the noise cancelling effect using the sound transducer 7130 upon detection that the user is waking up.

As discussed above, in some examples the eye mask system 7000 may be configured to move the cushion module 3150 (e.g. via actuation) from a non-contact position to a sealing position upon a change from a sleep-assist mode to the sleep mode (e.g. once the patient has fallen asleep). In some examples, the eye mask system 7000 may move the cushion module 3150 into the sealing position once the eye mask system 7000 has changed to sleep mode (e.g. upon detection of the patient being asleep).

5.9.3.9.2 Non-Treatment Mode and Treatment Mode

In some examples the eye mask system 7000 may be configured to operate in at least two modes: a non-treatment mode in which respiratory pressure therapy is not provided to the user, and a treatment mode in which respiratory pressure therapy is provided to the user for treatment of sleep disordered breathing. In some examples the eye mask system 7000 may comprise a removable cushion module 3150, for example as shown in and described herein with reference to FIG. 19. The eye mask system 7000 may be operable in the non-treatment mode in the absence of a cushion module 3150 attached to the eye mask 7100. The eye mask system 7000 may also be operable in the non-treatment mode when a cushion module 3150 is attached to the eye mask 7100. The user may remove the cushion module 3150 prior to use of the eye mask system 7000 in the non-treatment mode, and then attach the cushion module 3150 prior to use of the eye mask system 7000 in the treatment mode.

As described elsewhere herein, the eye mask system 7000 may comprise one or more transducers configured to influence the user's sleep and/or detect characteristics of the user's sleep and/or detect characteristics of the user during sleep. The one or more transducers may be as described elsewhere herein and, for example, may comprise one or more sensors configured to detect characteristics of the user's sleep and/or of the user during sleep.

In some examples, the user may wear and operate the eye mask system 7000 in a non-treatment mode without a cushion module 3150 attached to the eye mask 7100. In some examples the eye mask system 7000 may conduct analysis in the non-treatment mode. For example, the eye mask system 7000 may be configured to analyse an output of one or more sensors, and may identify sleep characteristics, identify a problem, predict an outcome and/or provide a recommendation based on the analysis. In some examples the eye mask system 7000 may be configured to detect and/or diagnose a disorder, or analyse data to check for a disorder, in the non-treatment mode. In some examples the eye mask system 7000 may be configured to detect sleep disordered breathing in at least the non-treatment mode. For example, the eye mask system 7000 may be configured to detect one or more of an apnea, hypopnea, hyperpnea, snoring and gasping in at least the non-treatment mode. The eye mask system 7000 may be configured to analyse output (s) of any one or more of the sensors to detect sleep disordered breathing, such as the ECG sensor 7111, HR sensor 7112, oxygen saturation sensor 7113, accelerometer 7115 and microphone 7118, as examples.

The eye mask system 7000 may be configured to detect sleep disordered breathing in the non-treatment mode, and may be configured to switch from the non-treatment mode to the treatment mode upon detection of sleep disordered breathing.

In some examples the eye mask system 7000 comprises a seal-forming structure 3100 movable between a non-contact position in which the seal-forming structure 3100 does not contact the user and sealing position in which the seal-forming structure 3100 is able to form a seal to the user's face. The eye mask system 7000 may be configured to move the seal-forming structure 3100 from a non-contact position to a sealing position upon switching from the non-treatment mode to the treatment mode. In some examples in which the eye masks system 7000 comprises a cushion module 3150, the eye mask system 7000 is configured to move the cushion module from a non-contact position to a contact position to move the seal-forming structure 3100 in the above described manner.

In some examples, the eye mask system 7000 is configured to identify that the user is asleep (for example using a method described elsewhere herein). The eye mask system 7000 may be configured to switch from the non-treatment mode to the treatment mode upon identifying that the user is asleep or falling asleep. The eye mask system 7000 may also be configured to switch from the treatment mode to the non-treatment mode upon detecting that the user is awake or waking.

5.9.3.9.3 Humidification

In some examples, the eye mask system 7000 configured for providing respiratory pressure therapy to a patient may comprise, may be in communication with, and/or may be fluidly connected to, a humidifier 5000. The humidifier 5000 may be configured to humidify (e.g. increase absolute humidity) a flow of air or breathable gas delivered to the patient.

The eye mask 7100 may be configured to connect to an air circuit 4170 configured to supply a flow of air at a therapeutic pressure from an RPT device 4000 to the eye mask 7100 and plenum chamber 3200 for breathing by a patient (such as in any of the examples shown in FIGS. 10-12). The air circuit 4170 may be connected to an outlet of a humidifier 5000, which itself receives the flow of air from the RPT device 4000.

In some forms, humidifier 5000 and eye mask 7100 may not communicate. The patient may turn the humidifier 5000 on and off and may adjust a power level of the humidifier 5000 to adjust the humidification of the supply of air. In some examples the eye mask 7100 comprises a humidity sensor (either an ambient humidity sensor or a humidity sensor configured to measure humidity of the supply of air at the therapeutic pressure) or may receive humidity readings from another device such as the RPT device 4000 or a standalone ambient humidity sensor. The eye mask system 7000 may provide a recommendation to user regarding humidification based on the detected humidity. In some examples, if the humidity detected by the eye mask system 7000 or other device is below a predetermined threshold, the eye mask system 7000 may prompt the user to user humidification. The user can then turn on the humidifier 5000.

In some examples the eye mask system 7000 may be configured to communicate with a humidifier 5000 via the communication module 7920. Alternatively or additionally the eye mask system 7000 may be configured to communicate with an RPT device 4000 which is in control of the humidifier 5000. In such examples the eye mask system 7000 may comprise a humidity sensor (again, either an ambient humidity sensor or a humidity sensor configured to measure humidity of the supply of air at the therapeutic pressure) or may receive humidity readings from another device such as the RPT device 4000 or a standalone ambient humidity sensor. In these examples the eye mask system 7000 may be configured to automatically enable humidification by controlling the humidifier 5000 via the communication module 7920. The eye mask system 7000 may control the humidifier 5000 directly or, if the humidifier is controlled only by the RPT device 4000 then the eye mask system 7000 may communicate with the RPT device 4000 to modify operation of the humidifier 5000.

In the above examples, where reference is made to enabling humidification based on ambient humidity, it is to be understood that the eye mask system 7000 may also be configured to control the humidifier 5000 or prompt the patient to increase an amount of already enabled humidification, for example by increasing a power level of the humidifier. The eye mask system 7000 may also disable humidification (or prompt the patient to disable humidification), or control the humidifier 5000 or prompt the patient to reduce an amount of humidification, for example by lowering a power level of the humidifier.

In other forms of the present technology in which an eye mask system 7000 comprises an integrated flow generator 7400, such as in the example shown in FIGS. 15 and 16, the eye masks system 7000 may also comprise a humidity sensor. The eye mask system 7000 may be configured to report the humidity to the user, for example so that the user can take steps to increase (or decrease, if desired) the ambient humidity, for example by operating a room humidifier.

It is to be understood that in some examples the humidity sensor may provide absolute or relative humidity readings and in some examples the eye mask system 7000 may convert from one type of humidity reading to the other using a corresponding temperature reading.

In some examples, such as any of the examples shown in FIGS. 10-12 or FIG. 15, the eye mask system 7000 may comprise a heat and moisture exchange (HMX). The patient may generate a level of humidified air upon exhalation, which comes from the mucosa of the airways. The eye mask system 7000 may comprise an HMX exposed to both the supply of air at the therapeutic pressure and the patient's exhaled air. The HMX can be used to recycle the exhaled moisture by capturing humidity from humidified air upon exhalation then reintroducing the moisture to the incoming supply of air to humidify it.

In some examples, eye mask system 7000 may be configured to analyse the output of a humidity sensor, for example an ambient humidity sensor or a humidity sensor measuring humidity of the incoming supply of air, and may be configured to prompt the patient to make a change in relation to the HMX. For example, the eye mask system 7000 may be configured to determine that the measured humidity (ambient or of the supply of air) is below a predetermined threshold and prompt the user to fit an HMX. Alternatively the eye mask system 7000 may be configured to prompt the user to remove an HMX. In some examples the eye mask system 7000 may be configured to prompt the user to change from one model of HMX to another model of HMX that provides for a different amount of humidification.

5.10 Glossary

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 milli-bar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.10.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.10.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.10.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.10.3 Anatomy 5.10.3.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

5.10.3.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.10.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.10.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.10.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.10.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.10.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.10.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S

With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.10.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.11 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.12 Reference Signs List

1000 Patient
1100 Bed partner
3000 Patient interface
3100 Sealing or seal-forming structure
3150 Cushion module
3200 Plenum chamber
3300 Positioning and stabilising structure/headgear
3310 Backstrap
3311 Parietal strap portion
3312 Occipital strap portion
3313 Lateral strap portion
3314 End portion
3320 Face support portion
3330 Arm
3400 Vent
3600 Connection port
4000 RPT device
4010 External housing
4012 Upper portion
4014 Lower Portion
4015 Panel
4016 Chassis
4018 Handle
4020 Pneumatic block
4100 Blower housing
4110 Air filter
4112 Inlet air filter
4114 Outlet air filter
4120 Muffler
4122 Inlet muffler
4124 Outlet muffler
4140 Pressure generator
4142 Blower
4144 Motor
4160 Anti spillback valve
4170 Air circuit
4175 Short tube
4202 Printed Circuit Board Assembly (PCBA)
4210 Electrical power supply
4220 Input devices
4230 Central controller
4232 Clock
4240 Therapy device controller
4250 Protection circuit
4260 Memory
4270 Transducers
4272 Pressure sensors
4274 Flow rate sensors
4276 Motor speed sensors
4280 Data communication interface
4282 Remote external communication network
4284 Local external communication network
4286 Remote external device
4288 Local external device
4290 Output devices
4292 Display driver
4294 Display
5000 Humidifier
5002 Humidifier inlet
5004 Humidifier outlet
5006 Humidifier base
5110 Humidifier reservoir
5120 Conductive portion
5130 Humidifier reservoir dock
5135 Locking lever
5150 Water level indicator
5240 Heating element
7000 Eye mask system
7100 Eye mask
7110 EEG sensor
7111 ECG sensor
7112 Heart rate sensor
7113 Oxygen saturation sensor
7114 Blood pressure sensor
7115 Accelerometer
7116 Body temperature sensor
7117 Ambient temperature sensor
7118 Microphone
7120 Housing
7130 Sound transducer
7131 Display
7132 Temperature transducer
7133 Scent transducer
7134 Lens
7140 Interfacing structure
7400 Flow generator
7900 Processor
7910 Memory
7920 Communication module

The invention claimed is:

1. An eye mask system for providing respiratory pressure therapy to a user for treatment of sleep disordered breathing, the eye mask system comprising:

an eye mask configured to cover the user's eyes in use, the eye mask comprising one or more transducers configured to influence the user's sleep and/or detect characteristics of the user's sleep and/or detect characteristics of the user during sleep;

wherein the eye mask system is configured to pressurised flow of air for delivery to at least an entrance to the user's nares at a therapeutic pressure for breathing by the user during use, wherein the eye mask further comprises:

a plenum chamber at least partially forming an interior space pressurisable to said therapeutic pressure, said plenum chamber sized and structured to receive the flow of air at said therapeutic pressure, a seal-forming structure constructed and arranged to form a seal with a region of the user's face surrounding an entrance to the user's airways, said seal-forming structure having a hole therein such that the flow of air at said therapeutic pressure is delivered to at least the entrance to the user's nares, the seal-forming structure constructed and arranged to maintain said therapeutic pressure in the interior space throughout the user's respiratory cycle in use; and a vent to allow a continuous flow of gases exhaled by the user from the interior space to ambient, said vent being sized and shaped to maintain said therapeutic pressure in the interior space in use.

2. The eye mask system of claim 1, wherein the one or more transducers comprise one or more sensors configured to detect characteristics of the user's sleep and/or of the user during sleep, wherein the eye mask system is configured to analyse an output of one or more of the sensors.

3. The eye mask system of claim 2, wherein the one or more sensors include one or more of: an EEG sensor, an ECG sensor, a heart rate sensor, an oxygen saturation sensor, a blood pressure sensor, an accelerometer, a microphone, an ambient temperature sensor and/or a body temperature sensor.

4. The eye mask system of claim 2, wherein the eye mask system is configured to identify sleep characteristics, identify a problem, predict an outcome and/or provide a recommendation based on the analysis.

5. The eye mask system of claim 2, wherein the eye mask system is configured to adjust said therapeutic pressure of the flow of air based on an output of one or more of the sensors.

6. The eye mask system of claim 5, wherein the eye mask system is configured to detect that the user is waking up and reduce said therapeutic pressure.

7. The eye mask system of claim 5, wherein the eye mask system is configured to reduce said therapeutic pressure upon detection of ambient noise above a predetermined threshold.

8. The eye mask system of claim 7, wherein the eye mask system is configured to detect and/or diagnose a disorder.

9. The eye mask system of claim 8, wherein the eye mask system is configured to detect sleep disordered breathing.

10. The eye mask system of claim 1, said eye mask system further comprising a connection port configured to fluidly connect to and receive the pressurized flow of air from an air circuit.

11. The eye mask system of claim 10, wherein the connection port is configured to engage and physically removably connect to the air circuit to receive the pressurized flow of air.

12. The eye mask system of claim 1, said eye mask system further comprising a flow generator configured to generate the pressurised flow of air at said therapeutic pressure for breathing by the user during use.

13. The eye mask system of claim 12, wherein the flow generator is attached to the eye mask or a positioning and stabilising structure of the eye mask system such that the flow generator is configured to be supported on the user's head during use.

14. An eye mask system for providing respiratory pressure therapy to a user for treatment of sleep disordered breathing, the eye mask system comprising:

an eye mask configured to cover the user's eyes in use and comprising:

a connection port configured to fluidly connect to and receive a positive pressurised flow of air from an air circuit at a therapeutic pressure for breathing by the user during use, the connection port provided to or fluidly connected to the eye mask; or a flow generator configured to generate a positive pressurised flow of air at a therapeutic pressure for breathing by the user during use, wherein the eye mask further comprises:

a plenum chamber at least partially forming an interior space pressurisable to said therapeutic pressure, said plenum chamber sized and structured to receive the flow of air at said therapeutic pressure, a seal-forming structure constructed and arranged to form a seal with a region of the user's face surrounding an entrance to the user's airways, said seal-forming structure having a hole therein such that the flow of air at said therapeutic pressure is delivered to at least an entrance to the user's nares, the seal-forming structure constructed and arranged to maintain said therapeutic pressure in the interior space throughout the user's respiratory cycle in use; and a vent to allow a continuous flow of gases exhaled by the user from the interior space to ambient, said vent being sized and shaped to maintain said therapeutic pressure in the interior space in use, wherein the eye mask system is configured to operate in at least two modes when worn by the user, the at least two modes including:

a non-treatment mode in which respiratory pressure therapy is not provided to the user, and a treatment mode in which respiratory pressure therapy is provided to the user for treatment of sleep disordered breathing.

15. The eye mask system of claim 14, wherein the eye mask system is configured to detect one or more of an apnea, hypopnea, hyperpnea and gasping in at least the non-treatment mode.

16. The eye mask system of claim 14, wherein the eye mask system is configured to detect sleep disordered breathing in the non-treatment mode and switch from the non-treatment mode to the treatment mode upon detection of sleep disordered breathing.

17. The eye mask system of claim 14, wherein when worn by the user, the seal-forming structure is movable between a non-contact position in which the seal-forming structure does not contact the user and a sealing position in which the seal-forming structure is able to form a seal to the user's face, the eye mask system configured to move the seal-forming structure from the non-contact position to the sealing position during a change from the non-treatment mode to the treatment mode.

18. The eye mask system of claim 14, wherein the eye mask system comprises a cushion module comprising the seal-forming structure and at least partially forming the plenum chamber.

19. The eye mask system of claim 18, wherein the cushion module is removably attachable to the eye mask.

20. The eye mask system of claim 19, wherein the eye mask system is operable in the non-treatment mode independently of whether or not the cushion module is attached to the eye mask.

21. The eye mask system of claim 19, wherein the cushion module is able to move relative to the eye mask.

22. The eye mask system of claim 21, wherein the cushion module is movable between a non-contact position in which the seal-forming structure does not contact the user and a sealing position in which the seal-forming structure is able to form a seal to the user's face.

23. The eye mask system of claim 22, wherein the eye mask system is configured to identify that the user is asleep.

24. The eye mask system of claim 23, wherein the eye mask system is configured to switch from the non-treatment mode to the treatment mode upon identifying that the user is asleep.

\* \* \* \* \*